(12) United States Patent
Bueche et al.

(10) Patent No.: US 9,023,095 B2
(45) Date of Patent: May 5, 2015

(54) STENT DELIVERY SYSTEM WITH PUSHER ASSEMBLY

(75) Inventors: Kenneth M. Bueche, Friendswood, TX (US); Michael P. Igoe, Seabrook, TX (US); Derek Blakeney, Houston, TX (US); Ronald G. Earles, Houston, TX (US)

(73) Assignee: IDev Technologies, Inc., Webster, TX (US)

( * ) Notice: Subject to any disclaimer, the term of this patent is extended or adjusted under 35 U.S.C. 154(b) by 626 days.

(21) Appl. No.: 13/118,325

(22) Filed: May 27, 2011

(65) Prior Publication Data
US 2011/0295354 A1 Dec. 1, 2011

Related U.S. Application Data

(60) Provisional application No. 61/349,104, filed on May 27, 2010, provisional application No. 61/433,184, filed on Jan. 14, 2011.

(51) Int. Cl.
*A61F 2/06* (2013.01)
*A61F 2/966* (2013.01)
*A61F 2/95* (2013.01)

(52) U.S. Cl.
CPC ......... *A61F 2/966* (2013.01); *A61F 2002/9517* (2013.01); *A61F 2250/0015* (2013.01); *Y10S 285/908* (2013.01)

(58) Field of Classification Search
CPC ... A61F 2/82; A61F 2/966; A61F 2002/9665; A61F 2/95; A61M 25/00
USPC .................. 606/108; 623/1.11–1.12, 1.23
See application file for complete search history.

(56) References Cited

U.S. PATENT DOCUMENTS 2,836,181 A 5/1958 Tapp
2,936,257 A 5/1960 Nailler et al.
(Continued)

FOREIGN PATENT DOCUMENTS

AU 2007309087 10/2012
CA 2083157 11/1991
(Continued)

OTHER PUBLICATIONS

Murayama et al., "Nonadhesive liquid embolic agent for cerebral arteriovenous malformations: Preliminary histopathological studies in swine rete mirabile," Neurosurgery, 43:1164-1172, 1998.
(Continued)

*Primary Examiner* — Katherine Dowe
*Assistant Examiner* — Sidharth Kapoor
(74) *Attorney, Agent, or Firm* — Jonathan D. Feuchtwang; Knobbe Martens Olson & Bear LLP

(57) ABSTRACT

A pusher assembly for a stent delivery device includes a distal end of an elongate member and a stent-engaging member having proximal and distal ends. The proximal end of the stent-engaging member is mechanically coupled to the distal end of the inner member by a connector, or the proximal end of the stent-engaging member is at least partially inside the distal end of the elongate inner member. The stent-engaging member includes a portion that radially outwardly extends towards the distal end of the stent-engaging member, or the stent-engaging member includes a portion that radially outwardly extends towards the distal end of the stent-engaging member. The stent-engaging member is configured to move a stent when distally advanced and configured to not move a stent when proximally retracted. A stent delivery device includes an elongate outer member, an elongate inner member coaxially positioned within the outer member, and the pusher assembly.

29 Claims, 35 Drawing Sheets

(56) References Cited

U.S. PATENT DOCUMENTS

| | | |
|---|---|---|
| 3,463,197 A | 8/1969 | Slade |
| 3,479,670 A | 11/1969 | Medell |
| 3,620,218 A | 11/1971 | Schmitt |
| 3,868,956 A | 3/1975 | Alfidi et al. |
| 4,503,569 A | 3/1985 | Dotter |
| 4,580,568 A | 4/1986 | Gianturco |
| 4,619,246 A | 10/1986 | Molgaard-Nielsen et al. |
| 4,665,906 A | 5/1987 | Jervis |
| 4,733,665 A | 3/1988 | Palmaz |
| 4,739,762 A | 4/1988 | Palmaz |
| 4,768,507 A | 9/1988 | Fischell et al. |
| 4,771,773 A | 9/1988 | Kropf |
| 4,776,337 A | 10/1988 | Palmaz |
| 4,850,999 A | 7/1989 | Planck |
| 4,877,030 A | 10/1989 | Beck et al. |
| 4,922,905 A | 5/1990 | Strecker |
| 4,950,227 A | 8/1990 | Savin et al. |
| 4,954,126 A | 9/1990 | Wallsten |
| 4,960,410 A | 10/1990 | Pinchuk |
| 4,969,458 A | 11/1990 | Wiktor |
| 4,990,151 A | 2/1991 | Wallsten |
| 4,994,071 A | 2/1991 | MacGregor |
| 4,997,440 A | 3/1991 | Dumican |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,059,211 A | 10/1991 | Stack et al. |
| 5,064,435 A | 11/1991 | Porter |
| 5,067,957 A | 11/1991 | Jervis |
| 5,102,417 A | 4/1992 | Palmaz |
| 5,104,404 A | 4/1992 | Wolff |
| 5,107,852 A | 4/1992 | Davidson et al. |
| 5,116,365 A | 5/1992 | Hillstead |
| 5,133,732 A | 7/1992 | Wiktor |
| 5,135,536 A | 8/1992 | Hillstead |
| 5,159,920 A | 11/1992 | Condon et al. |
| 5,171,262 A | 12/1992 | MacGregor |
| 5,180,376 A | 1/1993 | Fischell |
| 5,190,546 A | 3/1993 | Jervis |
| 5,201,757 A | 4/1993 | Heyn et al. |
| 5,201,901 A | 4/1993 | Harada et al. |
| 5,211,658 A | 5/1993 | Clouse |
| 5,219,355 A | 6/1993 | Parodi et al. |
| 5,246,445 A | 9/1993 | Yachia et al. |
| 5,256,158 A | 10/1993 | Tolkoff et al. |
| 5,261,916 A | 11/1993 | Engelson |
| 5,282,823 A | 2/1994 | Schwartz et al. |
| 5,304,220 A | 4/1994 | Maginot |
| 5,306,286 A | 4/1994 | Stack et al. |
| 5,342,387 A | 8/1994 | Summers |
| 5,344,402 A * | 9/1994 | Crocker ............... 604/103.01 |
| 5,350,398 A | 9/1994 | Pavcnik et al. |
| 5,360,443 A | 11/1994 | Barone et al. |
| 5,366,504 A | 11/1994 | Andersen et al. |
| 5,372,600 A | 12/1994 | Beyar et al. |
| 5,376,077 A | 12/1994 | Gomringer |
| 5,382,259 A | 1/1995 | Phelps et al. |
| 5,389,106 A | 2/1995 | Tower |
| 5,391,172 A | 2/1995 | Williams et al. |
| 5,395,390 A | 3/1995 | Simon et al. |
| 5,405,377 A | 4/1995 | Cragg |
| 5,405,378 A | 4/1995 | Strecker |
| 5,411,507 A | 5/1995 | Heckele |
| 5,411,549 A | 5/1995 | Peters |
| 5,415,664 A | 5/1995 | Pinchuk |
| 5,419,231 A | 5/1995 | Earle, III et al. |
| D359,802 S | 6/1995 | Fontaine |
| 5,425,739 A | 6/1995 | Jessen |
| 5,425,984 A | 6/1995 | Kennedy et al. |
| 5,433,723 A | 7/1995 | Lindenberg et al. |
| 5,433,729 A | 7/1995 | Adams et al. |
| 5,443,458 A | 8/1995 | Eury |
| 5,454,795 A | 10/1995 | Samson |
| 5,458,615 A | 10/1995 | Klemm et al. |
| 5,464,408 A | 11/1995 | Duc |
| 5,474,563 A | 12/1995 | Myler et al. |
| 5,476,508 A | 12/1995 | Amstrup |
| 5,478,355 A | 12/1995 | Muth et al. |
| 5,480,423 A | 1/1996 | Ravenscroft et al. |
| 5,484,425 A | 1/1996 | Fischell et al. |
| 5,484,444 A | 1/1996 | Braunschweiler et al. |
| 5,496,277 A | 3/1996 | Termin et al. |
| 5,507,769 A | 4/1996 | Marin et al. |
| 5,527,282 A | 6/1996 | Segal |
| 5,527,324 A | 6/1996 | Krantz et al. |
| 5,527,337 A | 6/1996 | Stack et al. |
| 5,534,007 A | 7/1996 | St. Germain et al. |
| 5,534,287 A | 7/1996 | Lukic |
| 5,536,274 A | 7/1996 | Neuss |
| 5,551,954 A | 9/1996 | Dinh et al. |
| 5,554,181 A | 9/1996 | Das |
| 5,571,167 A | 11/1996 | Maginot |
| 5,571,168 A | 11/1996 | Toro |
| 5,573,520 A | 11/1996 | Schwartz |
| 5,575,817 A | 11/1996 | Martin |
| 5,575,818 A | 11/1996 | Pinchuk |
| 5,591,172 A | 1/1997 | Bachmann et al. |
| 5,591,195 A | 1/1997 | Taheri et al. |
| 5,591,199 A | 1/1997 | Porter et al. |
| 5,591,222 A | 1/1997 | Susawa et al. |
| 5,597,378 A | 1/1997 | Jervis |
| 5,603,698 A | 2/1997 | Roberts et al. |
| 5,607,445 A | 3/1997 | Summers |
| 5,607,466 A | 3/1997 | Imbert et al. |
| 5,609,627 A | 3/1997 | Goicoechea et al. |
| 5,628,754 A | 5/1997 | Shevlin et al. |
| 5,628,787 A | 5/1997 | Mayer |
| 5,629,077 A | 5/1997 | Turnlund et al. |
| 5,630,840 A | 5/1997 | Mayer |
| 5,632,771 A | 5/1997 | Boatman et al. |
| 5,643,339 A | 7/1997 | Kavteladze et al. |
| 5,645,558 A | 7/1997 | Horton |
| 5,645,559 A | 7/1997 | Hachtman et al. |
| 5,653,684 A | 8/1997 | Laptewicz et al. |
| 5,653,727 A | 8/1997 | Wiktor |
| 5,662,703 A | 9/1997 | Yurek et al. |
| 5,662,713 A | 9/1997 | Andersen et al. |
| 5,667,523 A | 9/1997 | Bynon et al. |
| 5,669,880 A | 9/1997 | Solar |
| 5,669,924 A | 9/1997 | Shaknovich |
| 5,669,936 A | 9/1997 | Lazarus |
| 5,670,161 A | 9/1997 | Helay et al. |
| 5,674,276 A | 10/1997 | Andersen et al. |
| 5,674,277 A | 10/1997 | Freitag |
| 5,679,400 A | 10/1997 | Tuch |
| 5,679,470 A | 10/1997 | Mayer |
| 5,683,411 A | 11/1997 | Kavteladze et al. |
| 5,683,450 A | 11/1997 | Goicoechea et al. |
| 5,683,451 A | 11/1997 | Lenker et al. |
| 5,693,086 A | 12/1997 | Goicoechea et al. |
| 5,695,469 A | 12/1997 | Segal |
| 5,695,483 A | 12/1997 | Samson |
| 5,699,880 A | 12/1997 | Hockley |
| 5,700,269 A | 12/1997 | Pinchuk et al. |
| 5,702,373 A | 12/1997 | Samson |
| 5,702,418 A | 12/1997 | Ravenscroft |
| 5,707,376 A | 1/1998 | Kavteladze et al. |
| 5,709,701 A | 1/1998 | Parodi |
| 5,709,703 A | 1/1998 | Lukic et al. |
| 5,713,917 A | 2/1998 | Leonhardt et al. |
| 5,713,948 A | 2/1998 | Uflacker |
| 5,716,365 A | 2/1998 | Goicoechea et al. |
| 5,716,396 A | 2/1998 | Williams, Jr. |
| 5,718,159 A | 2/1998 | Thompson |
| 5,718,724 A | 2/1998 | Goicoechea et al. |
| 5,720,735 A | 2/1998 | Dorros |
| 5,725,571 A | 3/1998 | Imbert et al. |
| 5,725,572 A | 3/1998 | Lam et al. |
| 5,728,150 A | 3/1998 | McDonald et al. |
| 5,728,158 A | 3/1998 | Lau et al. |
| 5,733,267 A | 3/1998 | Del Toro |
| 5,733,327 A | 3/1998 | Igaki et al. |
| 5,741,325 A | 4/1998 | Chaikof et al. |

(56) References Cited

U.S. PATENT DOCUMENTS

| | | |
|---|---|---|
| 5,741,333 A | 4/1998 | Frid |
| 5,749,880 A | 5/1998 | Banas et al. |
| 5,749,921 A | 5/1998 | Lenker et al. |
| 5,755,708 A | 5/1998 | Segal |
| 5,758,562 A | 6/1998 | Thompson |
| 5,759,186 A | 6/1998 | Bachmann et al. |
| 5,766,204 A | 6/1998 | Porter et al. |
| 5,766,219 A | 6/1998 | Horton |
| 5,766,237 A | 6/1998 | Cragg |
| 5,766,710 A | 6/1998 | Turnlund et al. |
| 5,769,882 A | 6/1998 | Fogarty et al. |
| 5,772,668 A | 6/1998 | Summers et al. |
| 5,776,142 A | 7/1998 | Gunderson |
| 5,776,180 A | 7/1998 | Goicoechea et al. |
| 5,792,156 A | 8/1998 | Perouse |
| 5,797,952 A | 8/1998 | Klein |
| 5,800,508 A | 9/1998 | Goicoechea et al. |
| 5,800,511 A | 9/1998 | Mayer |
| 5,807,398 A | 9/1998 | Shaknovich |
| 5,824,041 A | 10/1998 | Lenker et al. |
| 5,824,053 A | 10/1998 | Khosravi et al. |
| 5,824,058 A | 10/1998 | Ravenscroft et al. |
| 5,824,077 A | 10/1998 | Mayer |
| 5,830,229 A | 11/1998 | Kónya et al. |
| 5,836,966 A | 11/1998 | St. Germain |
| RE35,988 E | 12/1998 | Winston et al. |
| 5,843,069 A * | 12/1998 | Butler et al. ............... 604/891.1 |
| 5,843,168 A | 12/1998 | Dang |
| 5,849,037 A | 12/1998 | Frid |
| 5,851,217 A | 12/1998 | Wolff et al. |
| 5,860,998 A | 1/1999 | Robinson et al. |
| 5,876,386 A | 3/1999 | Samson |
| 5,876,432 A | 3/1999 | Lau et al. |
| 5,888,201 A | 3/1999 | Stinson et al. |
| 5,891,130 A * | 4/1999 | Palermo et al. .................... 606/1 |
| 5,891,191 A | 4/1999 | Stinson |
| 5,902,332 A | 5/1999 | Schatz |
| 5,911,731 A | 6/1999 | Pham et al. |
| 5,913,896 A | 6/1999 | Boyle et al. |
| 5,916,196 A | 6/1999 | Andrea et al. |
| 5,916,263 A | 6/1999 | Goicoceha et al. |
| 5,922,003 A * | 7/1999 | Anctil et al. ................... 606/170 |
| 5,928,279 A | 7/1999 | Shannon et al. |
| 5,928,280 A | 7/1999 | Hansen et al. |
| 5,931,842 A | 8/1999 | Goldsteen et al. |
| 5,938,696 A | 8/1999 | Goicoechea et al. |
| 5,941,908 A | 8/1999 | Goldsteen et al. |
| 5,944,738 A | 8/1999 | Amplatz et al. |
| 5,954,729 A | 9/1999 | Bachmann et al. |
| 5,954,764 A | 9/1999 | Parodi |
| 5,964,771 A | 10/1999 | Beyar et al. |
| 5,968,052 A | 10/1999 | Sullivan, III et al. |
| 5,968,088 A | 10/1999 | Hansen et al. |
| 5,972,017 A | 10/1999 | Berg et al. |
| 5,976,155 A | 11/1999 | Foreman et al. |
| 5,976,178 A | 11/1999 | Goldsteen et al. |
| 5,989,276 A | 11/1999 | Houser et al. |
| 6,004,348 A | 12/1999 | Banas et al. |
| 6,007,574 A | 12/1999 | Pulnev et al. |
| 6,015,424 A | 1/2000 | Rosenbluth et al. |
| 6,017,319 A | 1/2000 | Jacobsen et al. |
| 6,019,778 A | 2/2000 | Wilson et al. |
| 6,019,785 A | 2/2000 | Strecker |
| 6,019,786 A | 2/2000 | Thompson |
| 6,024,763 A | 2/2000 | Lenker et al. |
| 6,027,529 A | 2/2000 | Roychowdhury et al. |
| 6,036,702 A | 3/2000 | Bachinski et al. |
| 6,039,755 A | 3/2000 | Edwin et al. |
| 6,042,588 A | 3/2000 | Munsinger et al. |
| 6,042,589 A | 3/2000 | Marianne |
| 6,042,605 A | 3/2000 | Martin et al. |
| 6,048,338 A | 4/2000 | Larson et al. |
| 6,051,020 A | 4/2000 | Goicoechea et al. |
| 6,053,943 A | 4/2000 | Edwin et al. |
| 6,059,752 A | 5/2000 | Segal |
| 6,063,113 A | 5/2000 | Kavteladze et al. |
| 6,077,295 A | 6/2000 | Limon et al. |
| 6,080,191 A | 6/2000 | Summers |
| 6,090,115 A | 7/2000 | Beyar et al. |
| 6,090,125 A | 7/2000 | Horton |
| 6,102,890 A | 8/2000 | Stivland et al. |
| 6,102,932 A | 8/2000 | Kurz |
| 6,117,167 A | 9/2000 | Goicoechea et al. |
| 6,120,432 A | 9/2000 | Sullivan et al. |
| 6,120,522 A | 9/2000 | Vrba et al. |
| 6,123,115 A | 9/2000 | Greenhalgh |
| 6,123,723 A | 9/2000 | Konya et al. |
| 6,124,523 A | 9/2000 | Banas et al. |
| 6,126,685 A | 10/2000 | Lenker et al. |
| 6,136,007 A | 10/2000 | Goldsteen et al. |
| 6,146,415 A | 11/2000 | Fitz |
| 6,149,681 A | 11/2000 | Houser et al. |
| 6,152,945 A | 11/2000 | Bachinski et al. |
| 6,156,062 A | 12/2000 | McGuinness |
| 6,159,239 A | 12/2000 | Greenhalgh |
| 6,164,339 A | 12/2000 | Greenhalgh |
| 6,165,213 A | 12/2000 | Goicoechea et al. |
| 6,168,622 B1 | 1/2001 | Mazzocchi |
| 6,171,326 B1 | 1/2001 | Ferrera et al. |
| 6,172,617 B1 | 1/2001 | Bullock |
| 6,183,508 B1 | 2/2001 | Stinson et al. |
| 6,186,942 B1 | 2/2001 | Sullivan et al. |
| 6,192,944 B1 | 2/2001 | Greenhalgh |
| 6,206,912 B1 | 3/2001 | Goldsteen et al. |
| 6,237,460 B1 | 5/2001 | Frid |
| 6,238,402 B1 | 5/2001 | Sullivan, III et al. |
| 6,238,430 B1 | 5/2001 | Klumb et al. |
| 6,241,757 B1 | 6/2001 | An et al. |
| 6,245,103 B1 | 6/2001 | Stinson |
| 6,248,112 B1 | 6/2001 | Gambale et al. |
| 6,248,122 B1 | 6/2001 | Klumb et al. |
| 6,251,132 B1 | 6/2001 | Ravenscroft et al. |
| 6,258,080 B1 | 7/2001 | Samson |
| 6,261,315 B1 | 7/2001 | St. Germain et al. |
| 6,264,684 B1 | 7/2001 | Banas et al. |
| 6,264,689 B1 | 7/2001 | Colgan et al. |
| 6,270,521 B1 | 8/2001 | Fischell et al. |
| 6,280,467 B1 | 8/2001 | Leonhardt |
| 6,293,955 B1 | 9/2001 | Houser et al. |
| 6,293,965 B1 | 9/2001 | Berg et al. |
| 6,295,714 B1 | 10/2001 | Roychowdhury et al. |
| 6,296,622 B1 | 10/2001 | Kurz et al. |
| 6,302,893 B1 | 10/2001 | Limon et al. |
| 6,302,905 B1 | 10/2001 | Goldsteen et al. |
| 6,302,906 B1 | 10/2001 | Goicoechea et al. |
| 6,306,105 B1 | 10/2001 | Rooney et al. |
| 6,306,141 B1 | 10/2001 | Jervis |
| 6,309,415 B1 | 10/2001 | Pulnev et al. |
| 6,312,454 B1 | 11/2001 | Stockel et al. |
| 6,319,267 B1 | 11/2001 | Kurz |
| 6,325,822 B1 | 12/2001 | Chouinard et al. |
| 6,331,184 B1 | 12/2001 | Abrams |
| 6,336,938 B1 | 1/2002 | Kavteladze et al. |
| 6,342,068 B1 | 1/2002 | Thompson |
| 6,346,118 B1 | 2/2002 | Baker et al. |
| 6,348,048 B1 | 2/2002 | Andrea et al. |
| 6,350,278 B1 | 2/2002 | Lenker et al. |
| 6,352,531 B1 * | 3/2002 | O'Connor et al. ............... 606/15 |
| 6,355,060 B1 | 3/2002 | Lenker et al. |
| 6,361,637 B2 | 3/2002 | Martin et al. |
| 6,371,953 B1 | 4/2002 | Beyar et al. |
| 6,371,979 B1 | 4/2002 | Beyar et al. |
| 6,379,365 B1 | 4/2002 | Diaz |
| 6,383,214 B1 | 5/2002 | Banas et al. |
| 6,383,216 B1 | 5/2002 | Kavteladze et al. |
| 6,391,051 B2 | 5/2002 | Sullivan, III et al. |
| 6,398,802 B1 | 6/2002 | Yee |
| 6,398,803 B1 | 6/2002 | Layne et al. |
| 6,409,750 B1 | 6/2002 | Hyodoh et al. |
| 6,419,694 B1 | 7/2002 | Sandock |
| 6,423,085 B1 | 7/2002 | Murayama et al. |
| 6,425,898 B1 | 7/2002 | Wilson et al. |
| 6,440,161 B1 | 8/2002 | Madrid et al. |
| 6,447,522 B2 | 9/2002 | Gambale et al. |

(56) References Cited

U.S. PATENT DOCUMENTS

| | | |
|---|---|---|
| 6,451,025 B1 | 9/2002 | Jervis |
| 6,451,033 B1 | 9/2002 | Berg et al. |
| 6,451,047 B2 | 9/2002 | McCrea et al. |
| 6,451,052 B1 | 9/2002 | Burmeister et al. |
| 6,468,301 B1 | 10/2002 | Amplatz et al. |
| 6,475,184 B1 | 11/2002 | Wang et al. |
| 6,475,209 B1 | 11/2002 | Larson et al. |
| 6,488,700 B2 | 12/2002 | Klumb et al. |
| 6,506,204 B2 | 1/2003 | Mazzocchi |
| 6,514,196 B1 | 2/2003 | Sullivan et al. |
| 6,514,261 B1 | 2/2003 | Randall et al. |
| 6,520,983 B1 | 2/2003 | Colgan et al. |
| 6,520,986 B2 | 2/2003 | Martin et al. |
| 6,527,802 B1 | 3/2003 | Mayer |
| 6,533,805 B1 | 3/2003 | Jervis |
| 6,554,798 B1 | 4/2003 | Mann et al. |
| 6,558,414 B2 | 5/2003 | Layne |
| 6,559,312 B2 | 5/2003 | Krauss et al. |
| 6,562,064 B1 | 5/2003 | deBeer |
| 6,572,645 B2 | 6/2003 | Leonhardt |
| 6,576,006 B2 | 6/2003 | Limon et al. |
| 6,579,314 B1 | 6/2003 | Lombardi et al. |
| 6,582,461 B1 | 6/2003 | Barmeister et al. |
| 6,585,695 B1 | 7/2003 | Adair et al. |
| 6,592,617 B2 | 7/2003 | Thompson |
| 6,599,296 B1 | 7/2003 | Gillick et al. |
| 6,605,102 B1 | 8/2003 | Mazzocchi et al. |
| 6,607,551 B1 | 8/2003 | Sullivan et al. |
| 6,613,075 B1 | 9/2003 | Healy et al. |
| 6,629,981 B2 | 10/2003 | Bui et al. |
| 6,638,291 B1 | 10/2003 | Ferrera et al. |
| 6,641,608 B1 | 11/2003 | Pulnev et al. |
| 6,645,237 B2 | 11/2003 | Klumb et al. |
| 6,652,544 B2 | 11/2003 | Houser et al. |
| 6,656,212 B2 | 12/2003 | Ravenscroft et al. |
| 6,660,030 B2 | 12/2003 | Shaolian et al. |
| 6,673,883 B1 | 1/2004 | Rowan |
| 6,679,903 B2 | 1/2004 | Kurz |
| 6,689,162 B1 | 2/2004 | Thompson |
| 6,695,862 B2 | 2/2004 | Cox et al. |
| 6,699,273 B2 | 3/2004 | Langan |
| 6,702,829 B2 | 3/2004 | Bachinski et al. |
| 6,709,379 B1 | 3/2004 | Brandau et al. |
| 6,712,835 B2 | 3/2004 | Mazzocchi et al. |
| 6,719,934 B2 | 4/2004 | Stinson |
| 6,726,712 B1 | 4/2004 | Raeder-Devens et al. |
| 6,730,117 B1 | 5/2004 | Tseng et al. |
| 6,733,519 B2 | 5/2004 | Lashinski et al. |
| 6,736,839 B2 | 5/2004 | Cummings |
| 6,736,840 B2 | 5/2004 | Fischell et al. |
| 6,740,077 B1 | 5/2004 | Brandau et al. |
| 6,740,115 B2 | 5/2004 | Lombardi et al. |
| 6,743,219 B1 | 6/2004 | Dwyer et al. |
| 6,749,627 B2 | 6/2004 | Thompson et al. |
| 6,755,854 B2 | 6/2004 | Gillick et al. |
| 6,758,858 B2 | 7/2004 | McCrea et al. |
| 6,770,087 B2 | 8/2004 | Layne et al. |
| 6,773,446 B1 | 8/2004 | Dwyer et al. |
| 6,776,791 B1 | 8/2004 | Stallings et al. |
| 6,790,226 B2 | 9/2004 | Edwin et al. |
| 6,792,979 B2 | 9/2004 | Konya et al. |
| 6,797,217 B2 | 9/2004 | McCrea et al. |
| RE38,653 E | 11/2004 | Igaki et al. |
| 6,814,750 B2 | 11/2004 | Kavteladze et al. |
| 6,846,316 B2 | 1/2005 | Abrams |
| RE38,711 E | 3/2005 | Igaki et al. |
| 6,859,986 B2 | 3/2005 | Jackson et al. |
| 6,860,898 B2 | 3/2005 | Stack et al. |
| 6,866,669 B2 | 3/2005 | Buzzard et al. |
| 6,866,679 B2 | 3/2005 | Kusleika |
| 6,913,618 B2 | 7/2005 | Denardo et al. |
| 6,926,732 B2 | 8/2005 | Derus et al. |
| 6,932,837 B2 | 8/2005 | Amplatz et al. |
| 6,939,352 B2 | 9/2005 | Buzzard et al. |
| 6,942,654 B1 | 9/2005 | Schaefer et al. |
| 6,942,688 B2 | 9/2005 | Bartholf et al. |
| 6,949,103 B2 | 9/2005 | Mazzocchi et al. |
| 6,962,597 B2 | 11/2005 | Goodin |
| 6,974,472 B2 | 12/2005 | Hong et al. |
| 6,989,019 B2 | 1/2006 | Mazzocchi et al. |
| 6,989,024 B2 | 1/2006 | Herbert et al. |
| 6,997,948 B2 | 2/2006 | Stinson |
| 7,001,420 B2 | 2/2006 | Speck et al. |
| 7,018,401 B1 | 3/2006 | Hyodoh et al. |
| 7,022,133 B2 | 4/2006 | Yee et al. |
| 7,033,375 B2 | 4/2006 | Mazzocchi et al. |
| 7,037,330 B1 | 5/2006 | Rivelli, Jr. et al. |
| 7,048,014 B2 | 5/2006 | Hyodoh et al. |
| 7,048,752 B2 | 5/2006 | Mazzocchi et al. |
| 7,052,511 B2 | 5/2006 | Weldon et al. |
| 7,052,513 B2 | 5/2006 | Thompson |
| 7,060,150 B2 | 6/2006 | Banas et al. |
| 7,070,607 B2 | 7/2006 | Murayama et al. |
| 7,083,631 B2 | 8/2006 | Houser et al. |
| 7,083,640 B2 | 8/2006 | Lombardi et al. |
| 7,094,248 B2 | 8/2006 | Bachinski et al. |
| 7,105,016 B2 | 9/2006 | Shiu et al. |
| 7,115,141 B2 | 10/2006 | Menz et al. |
| 7,122,050 B2 | 10/2006 | Randall et al. |
| 7,137,993 B2 | 11/2006 | Acosta et al. |
| 7,147,618 B2 | 12/2006 | Kurz |
| 7,147,655 B2 | 12/2006 | Chermoni |
| 7,156,860 B2 | 1/2007 | Wallsten |
| 7,160,323 B2 | 1/2007 | Pulnev et al. |
| 7,172,617 B2 | 2/2007 | Colgan et al. |
| 7,175,650 B2 | 2/2007 | Ruetsch |
| 7,211,095 B2 | 5/2007 | Bachinski et al. |
| 7,211,109 B2 | 5/2007 | Thompson |
| 7,241,308 B2 | 7/2007 | Andreas et al. |
| 7,270,668 B2 | 9/2007 | Andreas et al. |
| 7,279,005 B2 | 10/2007 | Stinson |
| 7,306,756 B2 | 12/2007 | Edwin et al. |
| 7,309,349 B2 | 12/2007 | Jackson et al. |
| 7,314,481 B2 | 1/2008 | Karpiel |
| 7,316,701 B2 | 1/2008 | Ferrera et al. |
| 7,316,708 B2 | 1/2008 | Gordon et al. |
| 7,320,702 B2 | 1/2008 | Hammersmark et al. |
| 7,326,236 B2 | 2/2008 | Andreas et al. |
| 7,329,279 B2 | 2/2008 | Haug et al. |
| 7,344,514 B2 | 3/2008 | Shanley |
| 7,344,558 B2 | 3/2008 | Lorenzo et al. |
| 7,367,985 B2 | 5/2008 | Mazzocchi et al. |
| 7,367,986 B2 | 5/2008 | Mazzocchi et al. |
| 7,367,987 B2 | 5/2008 | Balgobin et al. |
| 7,371,250 B2 | 5/2008 | Mazzocchi et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,381,219 B2 | 6/2008 | Salahieh et al. |
| 7,387,640 B2 | 6/2008 | Cummings |
| 7,396,362 B2 | 7/2008 | Jervis |
| 7,402,170 B2 | 7/2008 | McCullagh et al. |
| 7,404,820 B2 | 7/2008 | Mazzocchi et al. |
| 7,410,492 B2 | 8/2008 | Mazzocchi et al. |
| 7,419,502 B2 | 9/2008 | Pulnev et al. |
| 7,419,503 B2 | 9/2008 | Pulnev et al. |
| 7,442,200 B2 | 10/2008 | Mazzocchi et al. |
| 7,445,631 B2 | 11/2008 | Salahieh et al. |
| 7,462,192 B2 | 12/2008 | Norton et al. |
| 7,468,071 B2 | 12/2008 | Edwin et al. |
| 7,491,224 B2 | 2/2009 | Cox et al. |
| 7,500,989 B2 | 3/2009 | Solem et al. |
| 7,510,570 B1 | 3/2009 | Goicoechea et al. |
| 7,517,361 B1 | 4/2009 | Ravenscroft |
| 7,520,893 B2 | 4/2009 | Rivelli, Jr. |
| 7,527,632 B2 | 5/2009 | Houghton et al. |
| 7,527,643 B2 | 5/2009 | Case et al. |
| 7,534,250 B2 | 5/2009 | Schaeffer et al. |
| RE40,816 E | 6/2009 | Taylor et al. |
| 7,550,001 B2 | 6/2009 | Dorn et al. |
| 7,550,002 B2 | 6/2009 | Goto et al. |
| 7,553,322 B2 | 6/2009 | Dorn et al. |
| 7,553,323 B1 | 6/2009 | Perez et al. |
| 7,556,635 B2 | 7/2009 | Mazzocchi et al. |

(56) References Cited

U.S. PATENT DOCUMENTS

| | | | |
|---|---|---|---|
| 7,556,636 B2 | 7/2009 | Mazzocchi et al. | |
| 7,566,338 B2 | 7/2009 | Mazzocchi et al. | |
| 7,566,342 B2 | 7/2009 | Parker et al. | |
| 7,572,273 B2 | 8/2009 | Mazzocchi et al. | |
| 7,578,829 B2 | 8/2009 | Goldsteen et al. | |
| 7,578,830 B2 | 8/2009 | Kusleika et al. | |
| 7,578,838 B2 | 8/2009 | Melsheimer | |
| 7,578,899 B2 | 8/2009 | Edwin et al. | |
| 7,582,101 B2 | 9/2009 | Jones et al. | |
| 7,604,661 B2 | 10/2009 | Pavcnik et al. | |
| 7,608,058 B2 | 10/2009 | Wilson et al. | |
| 7,608,099 B2 | 10/2009 | Johnson et al. | |
| 7,611,528 B2 | 11/2009 | Goodson, IV et al. | |
| 7,621,946 B2 | 11/2009 | Turner et al. | |
| 7,628,803 B2 | 12/2009 | Pavcnik et al. | |
| 7,637,934 B2 | 12/2009 | Mangiardi et al. | |
| 7,651,521 B2 | 1/2010 | Ton et al. | |
| 7,655,039 B2 | 2/2010 | Leanna et al. | |
| 7,666,218 B2 | 2/2010 | Klein et al. | |
| 7,670,355 B2 | 3/2010 | Mazzocchi et al. | |
| 7,670,356 B2 | 3/2010 | Mazzocchi | |
| 7,678,130 B2 | 3/2010 | Mazzocchi et al. | |
| 7,686,815 B2 | 3/2010 | Mazzocchi et al. | |
| 7,691,124 B2 * | 4/2010 | Balgobin | 606/200 |
| 7,695,507 B2 | 4/2010 | Rivelli, Jr. et al. | |
| 7,717,923 B2 | 5/2010 | Kennedy, II et al. | |
| 7,717,949 B2 | 5/2010 | Dorn | |
| 7,736,386 B2 | 6/2010 | Pulnev et al. | |
| 7,748,389 B2 | 7/2010 | Salahieh et al. | |
| 7,763,068 B2 | 7/2010 | Pulnev et al. | |
| 7,766,960 B2 | 8/2010 | Alexander et al. | |
| 7,780,720 B2 | 8/2010 | Goicoechea et al. | |
| 7,785,340 B2 | 8/2010 | Heidner et al. | |
| 7,794,489 B2 | 9/2010 | Shumer et al. | |
| 7,806,919 B2 | 10/2010 | Bloom et al. | |
| 7,824,442 B2 | 11/2010 | Salahieh et al. | |
| 7,824,443 B2 | 11/2010 | Salahieh et al. | |
| 7,828,815 B2 | 11/2010 | Mazzocchi et al. | |
| 7,828,816 B2 | 11/2010 | Mazzocchi et al. | |
| 7,850,705 B2 | 12/2010 | Bachinski et al. | |
| 7,850,724 B2 | 12/2010 | Ruetsch | |
| 7,867,268 B2 | 1/2011 | Shelso | |
| 7,867,271 B2 | 1/2011 | Geiser et al. | |
| 7,879,080 B2 | 2/2011 | Sato | |
| 7,887,574 B2 | 2/2011 | McFerran | |
| 7,901,449 B2 | 3/2011 | Goicoechea et al. | |
| 7,918,880 B2 | 4/2011 | Austin | |
| 7,922,732 B2 | 4/2011 | Mazzocchi et al. | |
| 7,935,140 B2 | 5/2011 | Griffin | |
| 7,939,000 B2 | 5/2011 | McCrea et al. | |
| 7,942,919 B2 | 5/2011 | Goicoechea et al. | |
| 7,947,060 B2 | 5/2011 | Mazzocchi et al. | |
| 7,959,666 B2 | 6/2011 | Salahieh et al. | |
| 7,959,672 B2 | 6/2011 | Salahieh et al. | |
| 7,963,987 B2 | 6/2011 | Melsheimer et al. | |
| 2001/0010007 A1 | 7/2001 | Bachinski et al. | |
| 2001/0025131 A1 | 9/2001 | Edwin et al. | |
| 2001/0032010 A1 | 10/2001 | Sandock | |
| 2001/0049547 A1 | 12/2001 | Moore | |
| 2001/0051809 A1 | 12/2001 | Houser et al. | |
| 2002/0019659 A1 | 2/2002 | Goicoechea et al. | |
| 2002/0022857 A1 | 2/2002 | Goldsteen et al. | |
| 2002/0087046 A1 | 7/2002 | Sullivan et al. | |
| 2002/0087181 A1 | 7/2002 | Goldsteen et al. | |
| 2002/0138095 A1 | 9/2002 | Mazzocchi et al. | |
| 2002/0151955 A1 | 10/2002 | Tran et al. | |
| 2002/0169474 A1 | 11/2002 | Kusleika | |
| 2002/0173810 A1 | 11/2002 | Bachinski et al. | |
| 2002/0183827 A1 * | 12/2002 | Derus et al. | 623/1.12 |
| 2003/0009215 A1 | 1/2003 | Mayer | |
| 2003/0014062 A1 | 1/2003 | Houser et al. | |
| 2003/0014063 A1 | 1/2003 | Houser et al. | |
| 2003/0040771 A1 | 2/2003 | Hyodoh et al. | |
| 2003/0040772 A1 | 2/2003 | Hyodoh et al. | |
| 2003/0050686 A1 | 3/2003 | Raeder-Devens et al. | |
| 2003/0083541 A1 | 5/2003 | Sullivan et al. | |
| 2003/0109886 A1 | 6/2003 | Keegan et al. | |
| 2003/0130721 A1 | 7/2003 | Martin et al. | |
| 2003/0208263 A1 | 11/2003 | Burmeister et al. | |
| 2003/0216803 A1 * | 11/2003 | Ledergerber | 623/1.13 |
| 2004/0073287 A1 | 4/2004 | Goicoechea et al. | |
| 2004/0093056 A1 | 5/2004 | Johnson et al. | |
| 2004/0098081 A1 | 5/2004 | Landreville et al. | |
| 2004/0098115 A1 | 5/2004 | Goicoechea et al. | |
| 2004/0106979 A1 | 6/2004 | Goicoechea et al. | |
| 2004/0117004 A1 | 6/2004 | Osborne et al. | |
| 2004/0133264 A1 | 7/2004 | Moore | |
| 2004/0181239 A1 | 9/2004 | Dorn et al. | |
| 2004/0193179 A1 | 9/2004 | Nikolchev | |
| 2004/0199240 A1 | 10/2004 | Dorn | |
| 2004/0230286 A1 | 11/2004 | Moore et al. | |
| 2004/0236402 A1 | 11/2004 | Layne et al. | |
| 2004/0267348 A1 | 12/2004 | Gunderson et al. | |
| 2005/0021123 A1 | 1/2005 | Dorn et al. | |
| 2005/0059889 A1 | 3/2005 | Mayer | |
| 2005/0080475 A1 | 4/2005 | Andreas et al. | |
| 2005/0085892 A1 | 4/2005 | Goto et al. | |
| 2005/0090893 A1 | 4/2005 | Kavteladze et al. | |
| 2005/0113902 A1 | 5/2005 | Geiser et al. | |
| 2005/0119690 A1 | 6/2005 | Mazzocchi et al. | |
| 2005/0137686 A1 | 6/2005 | Salahieh et al. | |
| 2005/0137687 A1 | 6/2005 | Salahieh et al. | |
| 2005/0137688 A1 | 6/2005 | Salahieh et al. | |
| 2005/0137689 A1 | 6/2005 | Salahieh et al. | |
| 2005/0137691 A1 | 6/2005 | Salahieh et al. | |
| 2005/0137692 A1 | 6/2005 | Haug et al. | |
| 2005/0137694 A1 | 6/2005 | Haug et al. | |
| 2005/0137696 A1 | 6/2005 | Salahieh et al. | |
| 2005/0137697 A1 | 6/2005 | Salahieh et al. | |
| 2005/0137699 A1 | 6/2005 | Salahieh et al. | |
| 2005/0137701 A1 | 6/2005 | Salahieh et al. | |
| 2005/0143809 A1 | 6/2005 | Salahieh et al. | |
| 2005/0149160 A1 | 7/2005 | McFerran | |
| 2005/0154439 A1 | 7/2005 | Gunderson | |
| 2005/0182475 A1 | 8/2005 | Jen et al. | |
| 2005/0209670 A1 | 9/2005 | George et al. | |
| 2005/0209671 A1 | 9/2005 | Ton et al. | |
| 2005/0209672 A1 | 9/2005 | George et al. | |
| 2005/0209675 A1 | 9/2005 | Ton et al. | |
| 2005/0209676 A1 | 9/2005 | Kusleika | |
| 2005/0216051 A1 | 9/2005 | Mazzocchi et al. | |
| 2005/0246010 A1 | 11/2005 | Alexander et al. | |
| 2005/0267568 A1 * | 12/2005 | Berez et al. | 623/1.35 |
| 2005/0288764 A1 | 12/2005 | Snow et al. | |
| 2006/0015168 A1 | 1/2006 | Gunderson | |
| 2006/0036309 A1 | 2/2006 | Herbert et al. | |
| 2006/0058835 A1 | 3/2006 | Murayama et al. | |
| 2006/0058865 A1 | 3/2006 | Case | |
| 2006/0058872 A1 | 3/2006 | Salahieh et al. | |
| 2006/0074478 A1 | 4/2006 | Feller, III | |
| 2006/0100687 A1 | 5/2006 | Fahey et al. | |
| 2006/0116750 A1 | 6/2006 | Herbert et al. | |
| 2006/0136034 A1 | 6/2006 | Modesitt et al. | |
| 2006/0161195 A1 | 7/2006 | Goldsteen et al. | |
| 2006/0184224 A1 | 8/2006 | Angel | |
| 2006/0184226 A1 | 8/2006 | Austin | |
| 2006/0212105 A1 | 9/2006 | Dorn et al. | |
| 2006/0229714 A1 | 10/2006 | Lombardi et al. | |
| 2006/0241686 A1 | 10/2006 | Ferrera et al. | |
| 2006/0247661 A1 * | 11/2006 | Richards et al. | 606/108 |
| 2006/0253191 A1 | 11/2006 | Salahieh et al. | |
| 2006/0276873 A1 | 12/2006 | Sato | |
| 2007/0010876 A1 | 1/2007 | Salaheih et al. | |
| 2007/0010877 A1 | 1/2007 | Salahieh et al. | |
| 2007/0021821 A1 | 1/2007 | Johnson et al. | |
| 2007/0043420 A1 | 2/2007 | Lostetter | |
| 2007/0083253 A1 | 4/2007 | Fischell et al. | |
| 2007/0093889 A1 | 4/2007 | Wu et al. | |
| 2007/0100421 A1 | 5/2007 | Griffin | |
| 2007/0106367 A1 | 5/2007 | Ruetsch | |
| 2007/0118206 A1 | 5/2007 | Colgan et al. | |
| 2007/0118207 A1 | 5/2007 | Amplatz et al. | |
| 2007/0118214 A1 | 5/2007 | Salahieh et al. | |
| 2007/0156223 A1 | 7/2007 | Vaughan | |

(56) References Cited

U.S. PATENT DOCUMENTS

| | | |
|---|---|---|
| 2007/0162103 A1 | 7/2007 | Case et al. |
| 2007/0162107 A1 | 7/2007 | Haug et al. |
| 2007/0173868 A1 | 7/2007 | Bachinski et al. |
| 2007/0198076 A1 | 8/2007 | Hebert et al. |
| 2007/0203503 A1 | 8/2007 | Salahieh et al. |
| 2007/0203563 A1 | 8/2007 | Hebert et al. |
| 2007/0208405 A1 | 9/2007 | Goodin et al. |
| 2007/0219612 A1 | 9/2007 | Andreas et al. |
| 2007/0219616 A1 | 9/2007 | Modesitt et al. |
| 2007/0219617 A1 | 9/2007 | Saint |
| 2007/0233224 A1 | 10/2007 | Leynov et al. |
| 2007/0244540 A1 | 10/2007 | Pryor |
| 2007/0244552 A1 | 10/2007 | Salahieh et al. |
| 2007/0250151 A1 | 10/2007 | Pereira |
| 2007/0255386 A1 | 11/2007 | Tenne |
| 2007/0270930 A1 | 11/2007 | Schenck |
| 2007/0270932 A1 | 11/2007 | Headley et al. |
| 2007/0270936 A1 | 11/2007 | Andreas et al. |
| 2007/0282420 A1 | 12/2007 | Gunderson |
| 2007/0293928 A1 | 12/2007 | Tomlin |
| 2007/0293929 A1 | 12/2007 | Aoba et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0004685 A1 | 1/2008 | Seemann et al. |
| 2008/0039863 A1 | 2/2008 | Keegan et al. |
| 2008/0065147 A1 | 3/2008 | Mazzocchi et al. |
| 2008/0071308 A1 | 3/2008 | Mazzocchi et al. |
| 2008/0091257 A1 | 4/2008 | Andreas et al. |
| 2008/0097572 A1 | 4/2008 | Sheldon et al. |
| 2008/0109059 A1 | 5/2008 | Gordon et al. |
| 2008/0125806 A1 | 5/2008 | Mazzocchi et al. |
| 2008/0125849 A1 | 5/2008 | Burpee et al. |
| 2008/0125859 A1 | 5/2008 | Salahieh et al. |
| 2008/0132989 A1 | 6/2008 | Snow et al. |
| 2008/0183272 A1 | 7/2008 | Wood et al. |
| 2008/0221654 A1 | 9/2008 | Buiser et al. |
| 2008/0234795 A1 | 9/2008 | Snow et al. |
| 2008/0234796 A1 | 9/2008 | Dorn |
| 2008/0234814 A1 | 9/2008 | Salahieh et al. |
| 2008/0262591 A1 | 10/2008 | Shin et al. |
| 2008/0288043 A1 | 11/2008 | Kaufmann et al. |
| 2008/0290076 A1 | 11/2008 | Sheldon et al. |
| 2008/0294231 A1 | 11/2008 | Aguilar et al. |
| 2008/0300667 A1 | 12/2008 | Hebert et al. |
| 2009/0030495 A1 | 1/2009 | Koch |
| 2009/0036967 A1 | 2/2009 | Cummings |
| 2009/0054969 A1 | 2/2009 | Salahieh et al. |
| 2009/0082841 A1 | 3/2009 | Zacharias et al. |
| 2009/0099637 A1 | 4/2009 | Barthold et al. |
| 2009/0099643 A1 | 4/2009 | Hyodoh et al. |
| 2009/0125092 A1 | 5/2009 | McCrea et al. |
| 2009/0143849 A1 | 6/2009 | Ozawa et al. |
| 2009/0149936 A1 | 6/2009 | Lentz |
| 2009/0157162 A1 | 6/2009 | Chow et al. |
| 2009/0171427 A1 | 7/2009 | Melsheimer et al. |
| 2009/0177260 A1 | 7/2009 | Aggerholm |
| 2009/0177264 A1 | 7/2009 | Ravenscroft |
| 2009/0182407 A1 | 7/2009 | Leanna et al. |
| 2009/0182410 A1 | 7/2009 | Case et al. |
| 2009/0192584 A1* | 7/2009 | Gerdts et al. ............. 623/1.11 |
| 2009/0228092 A1 | 9/2009 | Raeder-Devens et al. |
| 2009/0234428 A1 | 9/2009 | Snow et al. |
| 2009/0234443 A1 | 9/2009 | Ottma et al. |
| 2009/0254168 A1 | 10/2009 | Parker et al. |
| 2009/0276028 A1 | 11/2009 | Bailey et al. |
| 2009/0276030 A1 | 11/2009 | Kusleika |
| 2009/0276033 A1 | 11/2009 | Mayer |
| 2009/0299449 A1 | 12/2009 | Styrc |
| 2009/0299451 A1 | 12/2009 | Ellsworth et al. |
| 2009/0299461 A1 | 12/2009 | Chermoni |
| 2009/0311132 A1 | 12/2009 | Banas et al. |
| 2009/0312829 A1 | 12/2009 | Aoba et al. |
| 2010/0004729 A1 | 1/2010 | Chew et al. |
| 2010/0004732 A1 | 1/2010 | Johnson et al. |
| 2010/0010617 A1 | 1/2010 | Goodson IV et al. |
| 2010/0030320 A1 | 2/2010 | Feller, III |
| 2010/0042198 A1 | 2/2010 | Burton |
| 2010/0042199 A1 | 2/2010 | Burton |
| 2010/0057191 A1 | 3/2010 | Pavcnik et al. |
| 2010/0094399 A1 | 4/2010 | Dorn et al. |
| 2010/0204774 A1 | 8/2010 | Goodin et al. |
| 2010/0286756 A1 | 11/2010 | Dorn et al. |
| 2011/0295354 A1 | 12/2011 | Bueche et al. |

FOREIGN PATENT DOCUMENTS

| | | |
|---|---|---|
| CA | 2173664 | 10/1996 |
| CA | 2247891 | 9/1997 |
| CA | 2272947 | 6/1998 |
| CN | 102525700 A | 7/2012 |
| DE | 3618734 | 12/1986 |
| DE | 3902364 | 8/1989 |
| DE | 4104702 | 8/1992 |
| DE | 4235004 | 4/1993 |
| DE | 4420142 | 12/1995 |
| DE | 68927998 | 9/1997 |
| DE | 19703482 | 8/1998 |
| DE | 29919625 | 1/2000 |
| DE | 69131423 | 1/2000 |
| DE | 19910188 | 5/2000 |
| DE | 102005020785 | 11/2006 |
| DE | 102006053748 | 4/2008 |
| DE | 202010007592 | 10/2010 |
| EP | 0145166 | 6/1985 |
| EP | 0518839 | 12/1992 |
| EP | 0528039 | 2/1993 |
| EP | 0686379 | 12/1995 |
| EP | 0689807 | 1/1996 |
| EP | 0696447 | 2/1996 |
| EP | 0701800 | 3/1996 |
| EP | 0722700 | 7/1996 |
| EP | 0737452 | 10/1996 |
| EP | 0740928 | 11/1996 |
| EP | 0743047 | 11/1996 |
| EP | 0744163 | 11/1996 |
| EP | 0744164 | 11/1996 |
| EP | 0747021 | 12/1996 |
| EP | 0782841 | 7/1997 |
| EP | 0788012 | 8/1997 |
| EP | 0788802 | 8/1997 |
| EP | 0792627 | 9/1997 |
| EP | 0804909 | 11/1997 |
| EP | 0804934 | 11/1997 |
| EP | 0812579 | 12/1997 |
| EP | 0857471 | 8/1998 |
| EP | 0893108 | 1/1999 |
| EP | 0894505 | 2/1999 |
| EP | 0941716 | 9/1999 |
| EP | 0943302 | 9/1999 |
| EP | 0948946 | 10/1999 |
| EP | 1010406 | 6/2000 |
| EP | 1025813 | 8/2000 |
| EP | 1121911 | 8/2001 |
| EP | 1208816 | 5/2002 |
| EP | 1221307 | 7/2002 |
| EP | 1275352 | 1/2003 |
| EP | 1396239 | 3/2004 |
| EP | 1402847 | 3/2004 |
| EP | 1447058 | 8/2004 |
| EP | 1520557 | 4/2005 |
| EP | 1582178 | 10/2005 |
| EP | 1637092 | 3/2006 |
| EP | 1803423 | 7/2007 |
| EP | 1834610 | 9/2007 |
| EP | 1844739 | 10/2007 |
| EP | 1872742 | 1/2008 |
| EP | 1900382 | 3/2008 |
| EP | 1941845 | 7/2008 |
| FR | 2678508 | 1/1993 |
| FR | 2735967 | 1/1997 |
| GB | 1183497 | 3/1970 |
| GB | 1205743 | 9/1970 |
| GB | 1565828 | 4/1980 |

(56) References Cited

FOREIGN PATENT DOCUMENTS

| | | |
|---|---|---|
| GB | 2135585 | 9/1984 |
| HK | 1140405 | 10/2007 |
| HK | 1172815 | 5/2013 |
| IL | 198303 | 1/2012 |
| JP | 59-500652 | 4/1984 |
| JP | 07-508199 | 9/1995 |
| JP | 09-506540 | 6/1997 |
| JP | 09-173469 | 7/1997 |
| JP | 09-511160 | 11/1997 |
| JP | 09-512460 | 12/1997 |
| JP | 10-043313 | 2/1998 |
| JP | 10-272190 | 10/1998 |
| JP | 11-57021 | 3/1999 |
| JP | 2004-510490 | 4/2004 |
| JP | 2005-342539 | 12/2005 |
| JP | 2006-522649 | 5/2006 |
| JP | 2006-522649 | 10/2006 |
| RU | 2454974 | 10/2007 |
| SU | 1457921 | 2/1989 |
| WO | WO 83/03752 | 11/1983 |
| WO | WO 87/04935 | 8/1987 |
| WO | WO 89/03197 | 4/1989 |
| WO | WO 90/05554 | 5/1990 |
| WO | WO 91/17789 | 11/1991 |
| WO | WO 92/14408 | 9/1992 |
| WO | WO 94/00178 | 1/1994 |
| WO | WO 94/00179 | 1/1994 |
| WO | WO 94/03127 | 2/1994 |
| WO | WO 94/16646 | 8/1994 |
| WO | WO 94/22379 | 10/1994 |
| WO | WO 94/27667 | 12/1994 |
| WO | WO 95/17859 | 7/1995 |
| WO | WO 95/21592 | 8/1995 |
| WO | WO 95/27448 | 10/1995 |
| WO | WO 95/29646 | 11/1995 |
| WO | WO 95/31945 | 11/1995 |
| WO | WO 96/01591 | 1/1996 |
| WO | WO 96/17645 | 6/1996 |
| WO | WO 96/19953 | 7/1996 |
| WO | WO 96/28115 | 9/1996 |
| WO | WO 96/31174 | 10/1996 |
| WO | WO 96/32078 | 10/1996 |
| WO | WO 96/33677 | 10/1996 |
| WO | WO 96/40000 | 12/1996 |
| WO | WO 96/41589 | 12/1996 |
| WO | WO 97/09932 | 3/1997 |
| WO | WO 97/16133 | 5/1997 |
| WO | WO 97/21401 | 6/1997 |
| WO | WO 97/21403 | 6/1997 |
| WO | WO 97/26939 | 7/1997 |
| WO | WO 97/32546 | 9/1997 |
| WO | WO 97/48343 | 12/1997 |
| WO | WO 98/11847 | 3/1998 |
| WO | WO 98/19625 | 5/1998 |
| WO | WO 98/19629 | 5/1998 |
| WO | WO 98/19630 | 5/1998 |
| WO | WO 98/19636 | 5/1998 |
| WO | WO 98/23241 | 6/1998 |
| WO | WO 98/29043 | 7/1998 |
| WO | WO 98/33453 | 8/1998 |
| WO | WO 98/33454 | 8/1998 |
| WO | WO 98/46168 | 10/1998 |
| WO | WO 98/55027 | 12/1998 |
| WO | WO 99/04728 | 2/1999 |
| WO | WO 99/32051 | 7/1999 |
| WO | WO 99/43379 | 9/1999 |
| WO | WO 99/44538 | 9/1999 |
| WO | WO 00/09059 | 2/2000 |
| WO | WO 00/12016 | 3/2000 |
| WO | WO 00/18330 | 4/2000 |
| WO | WO 00/25841 | 5/2000 |
| WO | WO 00/44306 | 8/2000 |
| WO | WO 00/45741 | 8/2000 |
| WO | WO 00/45742 | 8/2000 |
| WO | WO 00/45743 | 8/2000 |
| WO | WO 00/48660 | 8/2000 |
| WO | WO 00/49973 | 8/2000 |
| WO | WO 00/71059 | 11/2000 |
| WO | WO 01/72240 | 10/2001 |
| WO | WO 02/066091 | 8/2002 |
| WO | WO 02/087470 | 11/2002 |
| WO | WO 02/102279 | 12/2002 |
| WO | WO 03/003944 | 1/2003 |
| WO | WO 03/073963 | 9/2003 |
| WO | WO 2004/016201 | 2/2004 |
| WO | WO 2004/080504 | 9/2004 |
| WO | WO 2004/091441 | 10/2004 |
| WO | WO 2005/062980 | 7/2005 |
| WO | WO 2006/088638 | 8/2006 |
| WO | WO 2008/027902 | 3/2008 |
| WO | WO 2008/051941 | 5/2008 |
| WO | WO 2008/051941 A2 | 5/2008 |
| WO | WO 2008/063496 | 5/2008 |
| WO | WO 2012/096687 | 7/2012 |

OTHER PUBLICATIONS

Punekar et al., "Post-surgical recurrent varicocele: efficacy of internal spermatic venography and steel-coil embolization," Br. J. Urol., 77:124:128, 1996.
White et al., "Pulmonary Arteriovenous Malformations: Techniques and Long-term Outcome of Embolotherapy," Radiology, 169:663-669, 1988.
JVIR Supplement, Scientific Program, SCVIR 22nd Annual Scientific Meeting, Mar. 8-13, 1997, Sheraton Washington Hotel, 8(1) Part 2, pp. 251-252, Jan.-Feb. 1997.
International Search Report and Written Opinion of the International Searching Authority for International Application No. PCT/US2007/082148, mailed on Mar. 6, 2008.
International Preliminary Report on Patentability and Written Opinion of the International Searching Authority for International Application No. PCT/US2007/082148, issued on Apr. 22, 2009.
International Search Report and Written Opinion of the International Searching Authority for International Application No. PCT/US2007/082165, mailed on Apr. 2, 2008.
International Preliminary Report on Patentability and Written Opinion of the International Searching Authority for International Application No. PCT/US2007/082165, issued on Apr. 22, 2009.
Office Action issued in German Patent Application No. 202010007592.0 on Mar. 31, 2011.
Notice of Allowance issued in Mexican Patent Application No. MX/a/2009/004292 on Feb. 12, 2013.
Notification on the Grant for Patent Right for Invention issued in Chinese Patent Application No. 200780046619.4 on Nov. 29, 2011.
Office Action issued in Japanese Patent Application No. 2009-534804 on May 23, 2012.
Office Action issued in Mexican Patent Application No. MX/a/2009/004292 on Oct. 26, 2011.
Office Action issued in Mexican Patent Application No. MX/a/2009/004292 on Jul. 3, 2012.
Office Action issued in Russian Patent Application No. 2009119252 on Oct. 6, 2011.
Office Action issued in U.S. Appl. No. 11/876,764 on Nov. 25, 2011.
Office Action issued in U.S. Appl. No. 11/876,764 on May 2, 2012.
Search Report and Written Opinion mailed Dec. 19, 2011 in International application No. PCT/US2011/038456.
Decision of Rejection issued in Japanese Patent Application No. 2009-534804 on Mar. 26, 2013.
Decision to Grant issued in Chinese Patent Application No. 200780046619.4 on Nov. 29, 2011.
Final Office Action issued in U.S. Appl. No. 11/876,666, dated Sep. 5, 2012.
Final Office Action issued in U.S. Appl. No. 12/125,811, dated Sep. 26, 2012.
Notice of Acceptance issued in Australian Patent Application No. 2007309087 on Jun. 19, 2012.
Notice of Allowance issued in U.S. Appl. No. 12/125,811, dated Dec. 12, 2012.

(56) References Cited

OTHER PUBLICATIONS

Notice of Reasons of Rejection issued in Japanese Patent Application No. 2012-209331 on Aug. 9, 2013.
Office Action issued in Australian Patent Application No. 2012202653 on May 3, 2013.
Office Action issued in Canadian Patent Application No. 2667322 on May 27, 2013.
Office Action issued in Chinese Patent Application No. 200780046619.4 on Jun. 24, 2011.
Office Action issued in U.S. Appl. No. 13/549,373 on Oct. 1, 2012.
Office Action in Australian Application No. 2011354703 dated Nov. 11, 2013 in 3 pages.
Office Action in European Application No. 07844525.1 dated Sep. 13, 2013 in 5 pages.
Office Action in U.S. Appl. No. 11/876,764 dated Dec. 4, 2013 in 63 pages.
Office Action issued in Chinese Application No. 201210014832.X mailed Dec. 27, 2013.

* cited by examiner

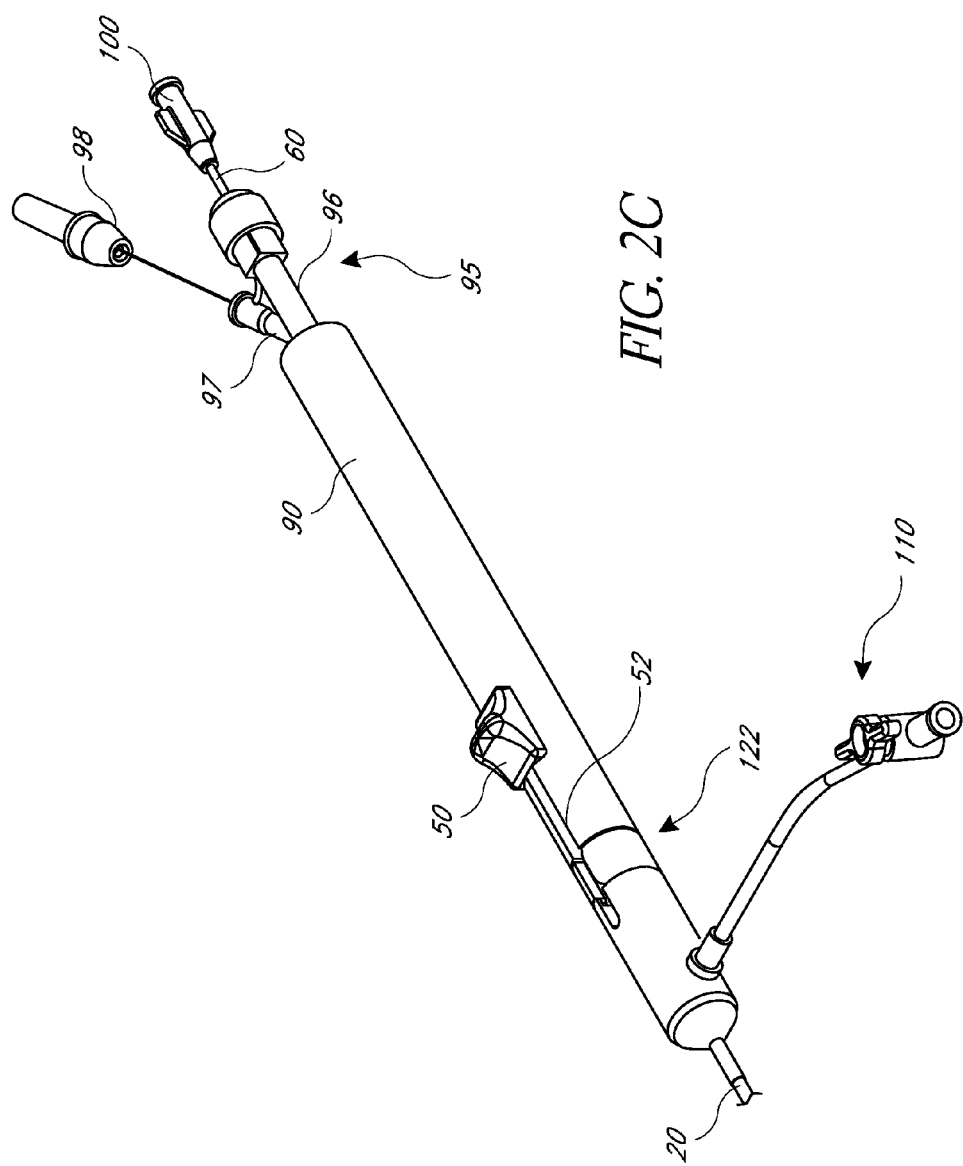

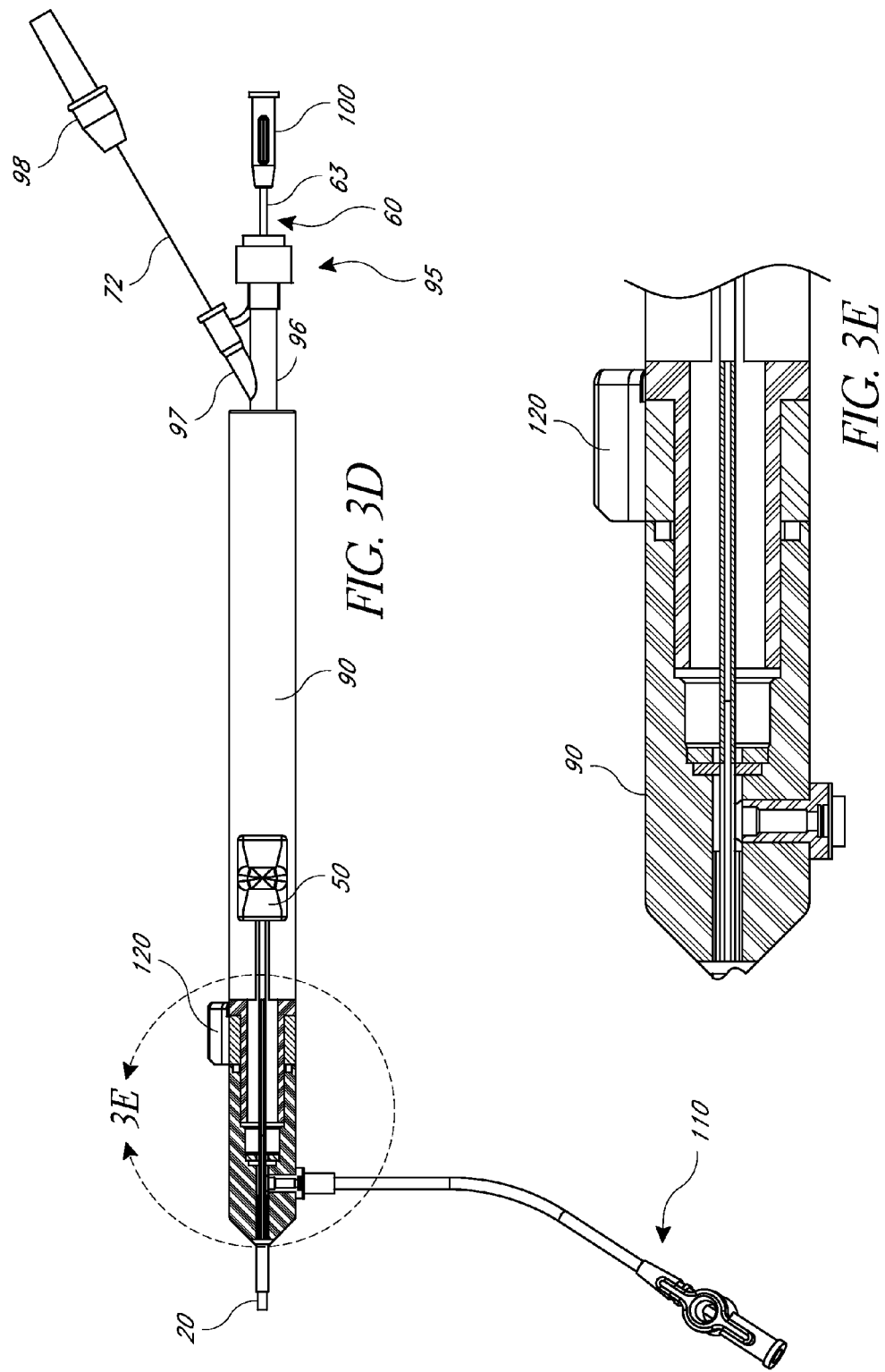

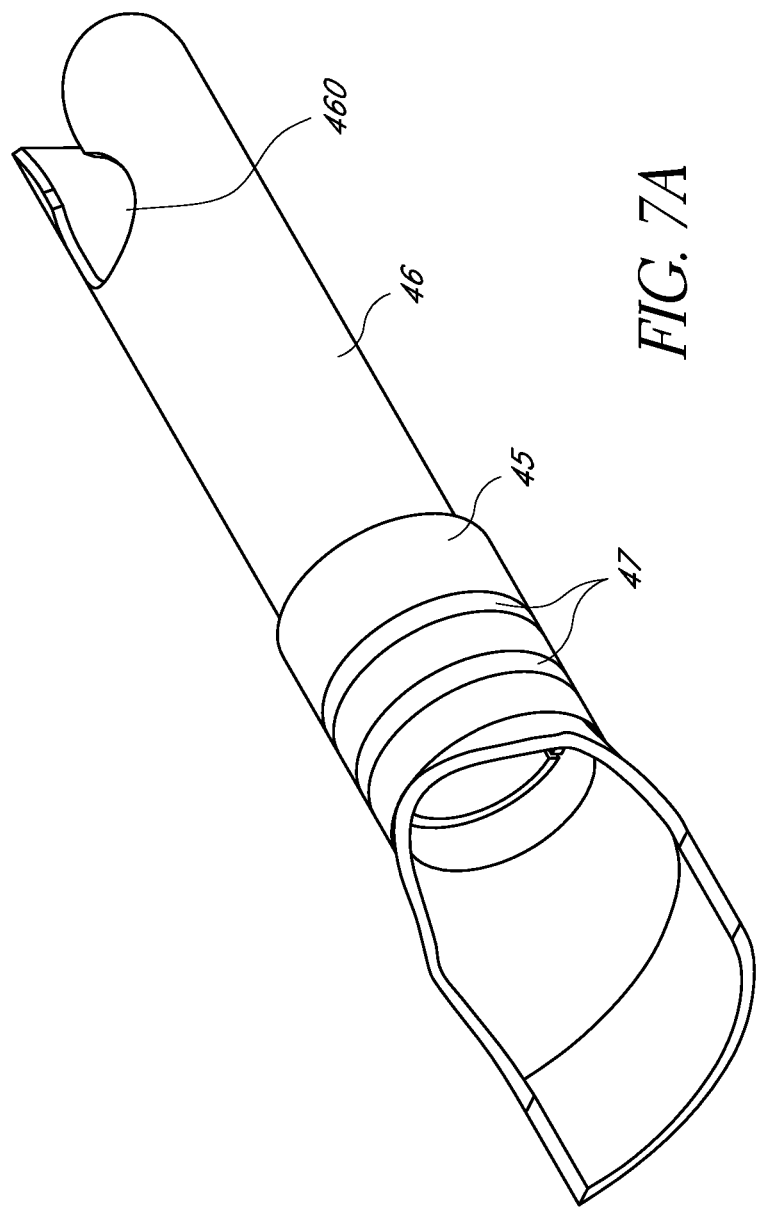

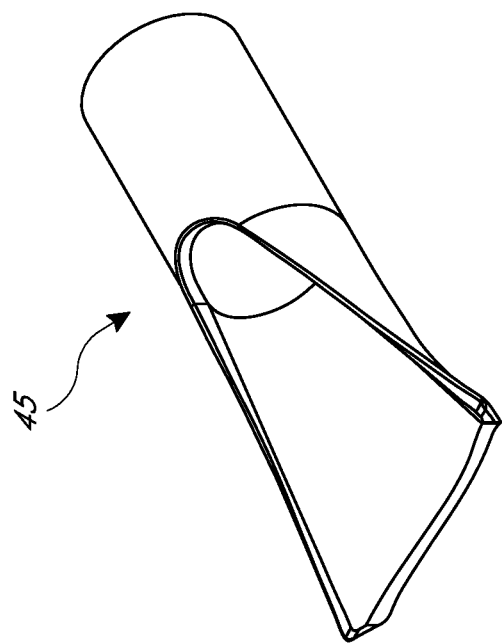
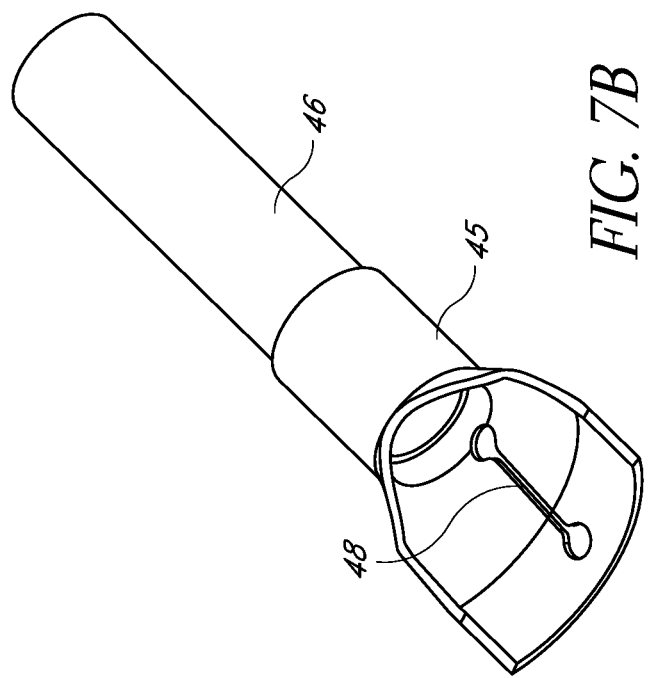
FIG. 7C
FIG. 7B

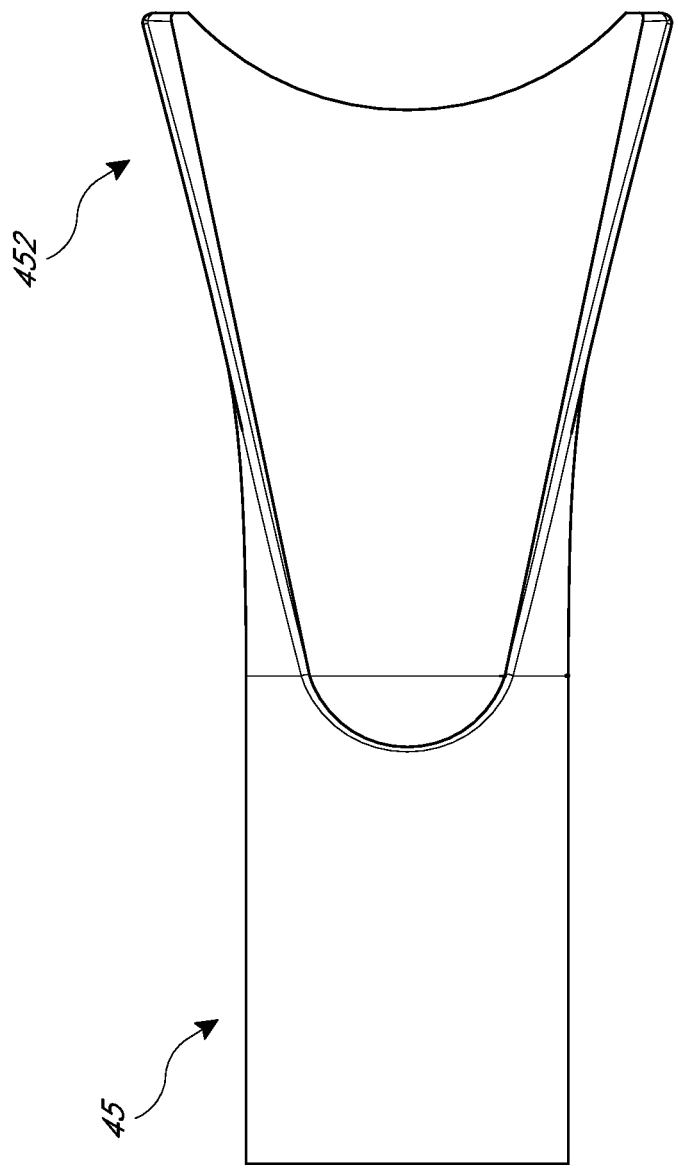

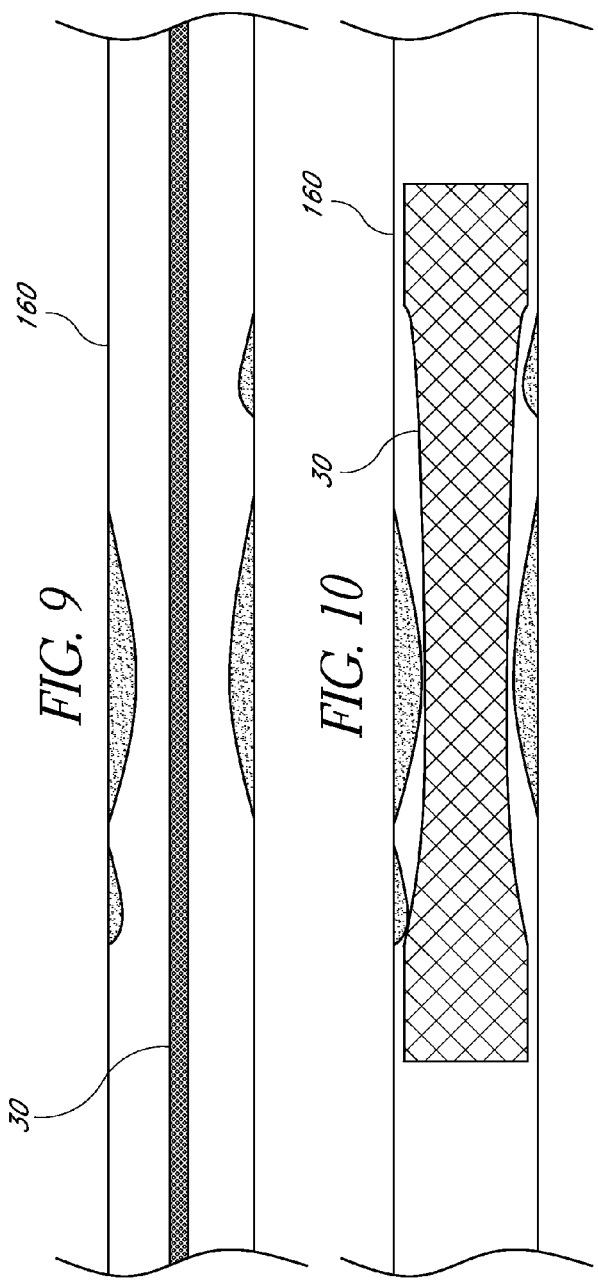
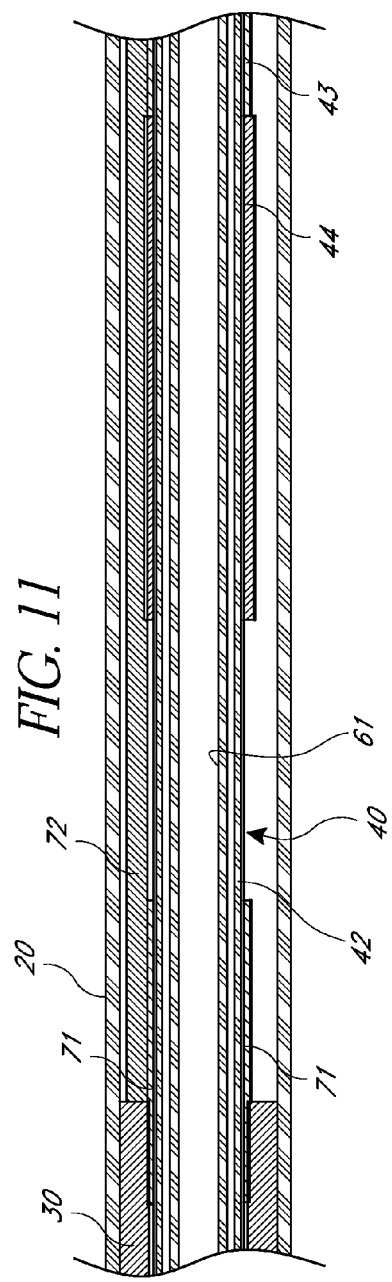

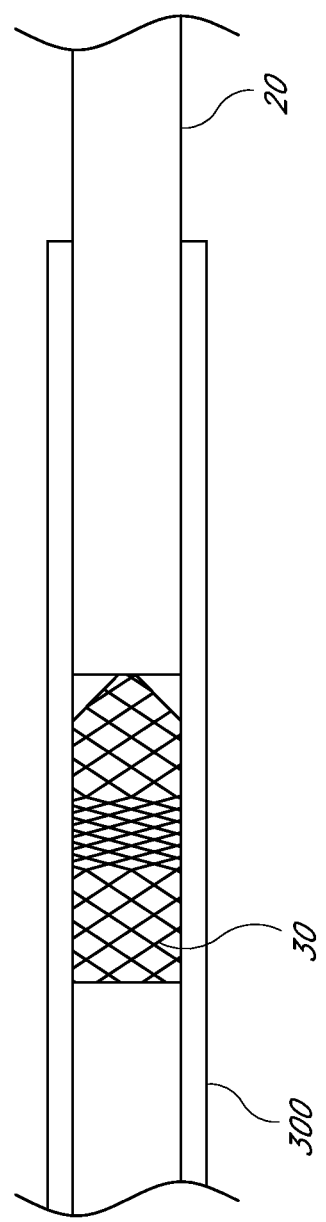

STENT DELIVERY SYSTEM WITH PUSHER ASSEMBLY

RELATED APPLICATIONS

This application claims priority benefit under 35 U.S.C. §119(e) of U.S. Provisional Patent Application No. 61/349,104, filed May 27, 2010, and U.S. Provisional Patent Application No. 61/433,184, filed Jan. 14, 2011, each of which is incorporated herein by reference in its entirety.

BACKGROUND

The present application generally relates to devices and methods for delivering a stent in a body vessel or in a non-body structure such as a polymer tube used for testing or demonstration.

Body vessels or certain non-body structures such as polymer tubes may be at least partially occluded. A stent can be inserted across a lesion or obstruction in order to restore patency to the vessel. Stents can also be used for other functions, such as trapping embolic material, increasing fluid flow, and the like.

SUMMARY

In certain embodiments, a system for delivering a stent comprises a stent, a stent delivery catheter, and a handle. The stent has a radially reduced configuration and a radially expanded configuration. The stent has a proximal end, a distal end, and length between the proximal end and the distal end. The stent comprises a plurality of openings along the length. The stent delivery catheter comprises an elongate outer tubular member, an elongate inner tubular member, and a stent-engaging member. The outer tubular member has a proximal end and a distal end. The stent is contained in the radially reduced configuration within the distal end of the outer tubular member. The elongate inner tubular member has a proximal end and a distal end. The inner tubular member extends within the outer tubular member. The inner tubular member at least partially defines a guidewire lumen. The stent-engaging member is coupled to the distal end of the elongate inner tubular member. The stent-engaging member comprises a ratchet having a shovel shape and a curved distal end. The stent-engaging member at least partially defines the guidewire lumen. The stent-engaging member is configured to engage the openings of the stent when distally advanced relative to the elongate outer tubular member to cause the stent to be moved distally out of the elongate outer tubular member, and is configured to slide past the openings of the stent when proximally retracted relative to the elongate outer tubular member. The handle is at the proximal end of the outer tubular member and the proximal end of the inner tubular member. The handle is adapted to control relative movement of the outer tubular member and the inner tubular member. In some embodiments, the stent-engaging member comprises a flex slot. In some embodiments, the stent-engaging member comprises nickel-titanium alloy. In some embodiments, the ratchet is configured to engage an intersection between filaments of a woven stent. In some embodiments, the ratchet is configured to engage a first intersection between filaments on a first side of a woven stent and a second intersection between filaments on a second side of the woven stent, the second side opposite to the first side. In some embodiments, the stent-engaging member comprises a stem and the ratchet is mechanically coupled to the stem. In some embodiments, the stem has a concave proximal end. In some embodiments, the ratchet is mechanically coupled to the stem by a plurality of longitudinally-spaced arcuate welds. In some embodiments, the ratchet is mechanically coupled to the stem by a plurality of spot welds. In some embodiments, the stent delivery catheter comprises a tubular connector coupling the inner tubular member and the stent-engaging member. In some embodiments, the stent delivery catheter comprises a tube positioned inward of the stent-engaging member and extending from proximate to the distal end of the inner tubular member to distal to the distal end of the stent-engaging member. In some embodiments, the tube comprises nylon. In some embodiments, the system further comprises an atraumatic tip mechanically coupled to the tube. In some embodiments, an outer diameter of the atraumatic tip is at least as large as an inner diameter of the elongate outer member. In some embodiments, the atraumatic tip comprises a generally conical distal end and a generally cylindrical proximal end comprising at least one aperture in fluid communication with an inner surface of the outer tubular member.

In certain embodiments, a pusher assembly for a stent delivery device comprises a distal end of an elongate inner member, a stent-engaging member having a proximal end and a distal end, and a connector mechanically coupling the distal end of the inner member and the proximal end of the stent-engaging member. The proximal end of the stent-engaging member is proximate to the distal end of the inner member. The stent-engaging member comprises a portion that radially outwardly extends towards the distal end of the stent-engaging member. The stent-engaging member is configured to move a stent when distally advanced and configured to not move a stent when proximally retracted. In some embodiments, the portion has a shovel shape having a curved distal end. In some embodiments, the portion has a shovel shape having a substantially flat distal end. In some embodiments, the stent-engaging member comprises a flex slot. In some embodiments, the stent-engaging member comprises nickel-titanium alloy. In some embodiments, the portion is configured to engage an intersection between filaments of a woven stent. In some embodiments, the portion is configured to engage a first intersection between filaments on a first side of a woven stent and a second intersection between filaments on a second side of the woven stent, the second side opposite to the first side. In some embodiments, the stent-engaging member comprises a stem and a ratchet mechanically coupled to the stem, the ratchet comprising the portion. In some embodiments, the stem has a concave proximal end. In some embodiments, the ratchet is mechanically coupled to the stem by a plurality of longitudinally-spaced arcuate welds. In some embodiments, the ratchet is mechanically coupled to the stem by a plurality of spot welds. In some embodiments, the inner member comprises an inner layer, a middle layer, and an outer layer, and the distal end of the inner member comprises the inner layer and the middle layer. In some embodiments, the inner member comprises an inner layer, a middle layer, and an outer layer, and the distal end of the inner member does not comprise the outer layer. In some embodiments, the connector comprises a tubular member radially outward of the distal end of the inner member and radially outward of the proximal end of the stent-engaging member. In some embodiments, the outer layer of the inner member has an outer diameter and the tubular member has an outer surface having an outer diameter substantially equal to the outer diameter of the outer layer of the inner member. In some embodiments, the middle layer of the inner member comprises a braid. In some embodiments, the braid comprises stainless steel. In some embodiments, the inner layer comprises nylon. In some embodiments, the outer layer comprises nylon. In some embodiments, the pusher assembly further comprises a tube positioned inward of the stent-engaging member and extending from proximate to the distal end of the inner member to distal to the distal end of the stent-engaging member. In some embodiments, the tube comprises nylon. In some embodiments, the inner member at least partially defines a guidewire lumen and the tube at least partially defines the guidewire lumen.

In certain embodiments, a stent delivery device comprises an elongate outer member at least partially defining an outer member lumen, an elongate inner member coaxially positioned within the outer member lumen, and a pusher assembly as described in the previous paragraph. In some embodiments, the pusher assembly further comprises a tube positioned inward of the stent-engaging member and extending from proximate to the distal end of the inner member to distal to the distal end of the stent-engaging member. In some embodiments, the tube comprises nylon. In some embodiments, the inner member at least partially defines a guidewire lumen and the tube at least partially defines the guidewire lumen. In some embodiments, the stent delivery device further comprises an atraumatic tip mechanically coupled to the tube. In some embodiments, the inner member at least partially defines a guidewire lumen, the tube at least partially defines the guidewire lumen, and the atraumatic tip at least partially defines the guidewire lumen. In some embodiments, an outer diameter of the atraumatic tip is at least as large as an inner diameter of the elongate outer member. In some embodiments, the atraumatic tip comprises a generally conical distal end and a generally cylindrical proximal end comprising at least one aperture in fluid communication with the outer member lumen. In some embodiments, the stent delivery device further comprises a handle stationarily coupled to the outer member and movably coupled to the inner member. The handle comprises a switch. Actuation of the switch causes movement of the stent-engaging member.

In certain embodiments, a tip for a catheter comprises a proximal end, a distal end, a lumen between the proximal end and the distal end, a generally conical portion proximate to the distal end, and a generally cylindrical portion proximate to the proximal end. The generally cylindrical portion has an outside surface and comprises at least one aperture configured to allow fluid communication between the proximal end and the outside surface.

In certain embodiments, a stent delivery device comprises an elongate outer member at least partially defining an outer member lumen, an elongate inner member having a proximal end and a distal end, and a tip as described in the previous paragraph mechanically coupled to the distal end of the inner member. The inner member is coaxially positioned within the outer member lumen. The at least one aperture of the tip is in fluid communication with the outer member lumen. In some embodiments, the stent delivery device further comprises the pusher assembly described three paragraphs prior. In some embodiments, the pusher assembly further comprises a tube positioned inward of the stent-engaging member and extending from proximate to the distal end of the inner member to distal to the distal end of the stent-engaging member. In some embodiments, the tube comprises nylon. In some embodiments, the inner member at least partially defines a guidewire lumen and the tube at least partially defines the guidewire lumen. In some embodiments, the tip is mechanically coupled to the tube.

In certain embodiments, a method of manufacturing a pusher assembly comprises mechanically coupling a distal end of an elongate inner member to a proximal end of a stent-engaging member using a connector. The stent-engaging member comprises a portion that radially expands towards a distal end of the stent-engaging member. The stent-engaging member is configured to move a stent when distally advanced and configured to not move a stent when proximally retracted. In some embodiments, mechanically coupling comprises heat shrinking the connector around the distal end of the elongate inner member and around the proximal end of the stent-engaging member. In some embodiments, the method further comprises removing a layer from the distal end of the elongate inner member. In some embodiments, forming the stent-engaging member comprising cutting, deforming, and heat setting a hypotube. In some embodiments, cutting the hypotube comprises forming a flex slot. In some embodiments, the stent-engaging member comprises a ratchet and a stem and the method further comprises welding the ratchet to the stem.

In certain embodiments, a system for delivering a stent comprises a stent, a stent delivery catheter, and a handle. The stent has a radially reduced configuration and a radially expanded configuration. The stent has a proximal end, a distal end, and length between the proximal end and the distal end. The stent comprises a plurality of openings along the length. The stent delivery catheter comprises an elongate outer tubular member, an elongate inner tubular member, and a stent-engaging member. The outer tubular member has a proximal end and a distal end. The stent is contained in the radially reduced configuration within the distal end of the outer tubular member. The elongate inner tubular member has a proximal end and a distal end. The inner tubular member extends within the outer tubular member. The inner tubular member at least partially defines a guidewire lumen. The stent-engaging member is configured to engage the openings of the stent when distally advanced relative to the elongate outer tubular member to cause the stent to be moved distally out of the elongate outer tubular member, and is configured to slide past the openings of the stent when proximally retracted relative to the elongate outer tubular member. The stent-engaging member comprises a ratchet and a stem. The ratchet has a proximal end and a shovel-shaped distal end. The stem is inward of the ratchet and is coupled to the ratchet. The stem has a proximal end and a distal end. The proximal end of the stem extends proximal to the proximal end of the ratchet. The proximal end of the ratchet is at least partially inside the distal end of the elongate inner tubular member. The distal end of the stem extends distal to the distal end of the ratchet. The handle is at the proximal end of the outer tubular member and the proximal end of the inner tubular member. The handle is adapted to control relative movement of the outer tubular member and the inner tubular member. In some embodiments, the ratchet is configured to engage an intersection between filaments of a woven stent. In some embodiments, the stem comprises a helical cutout. In some embodiments, the stem comprises a plurality of apertures. In some embodiments, the ratchet has a flat distal end. In some embodiments, the ratchet has a flared distal end. In some embodiments, the system further comprises an atraumatic tip mechanically coupled to the stem. In some embodiments, the atraumatic tip comprises a generally conical distal end and a generally cylindrical proximal end comprising at least one aperture in fluid communication with an inner surface of the outer tubular member.

In certain embodiments, a pusher assembly for a stent delivery device comprises a distal end of an elongate inner member and a stent engaging member. The stent-engaging member has a proximal end and a distal end. The proximal end of the stent-engaging member is at least partially inside the distal end of the elongate inner member. The stent-engaging member comprises a portion that radially outwardly extends towards the distal end of the stent-engaging member.

The stent-engaging member is configured to move a stent when distally advanced and configured to not move a stent when proximally retracted. In some embodiments, the stent-engaging member has a first internal diameter, the elongate inner member has a second internal diameter proximal to the proximal end of the stent-enganging member, and the first internal diameter is substantially equal to the second internal diameter. In some embodiments, the portion has a shovel shape having a curved distal end. In some embodiments, the portion has a shovel shape having a flat distal end. In some embodiments, the portion has a shovel shape having a flared distal end. In some embodiments, the stent-engaging member comprises nickel-titanium alloy. In some embodiments, the portion is configured to engage an intersection between filaments of a woven stent. In some embodiments, the stent-engaging member comprises a stem and a ratchet mechanically coupled to the stem, the ratchet comprising the portion. In some embodiments, the proximal end of the stent-engaging member comprises the stem. In some embodiments, the ratchet is mechanically coupled to the stem by a plurality of spot welds. In some embodiments, the proximal end of the stent-engaging member comprises an aperture, the elongate inner member comprises an inner layer, and the inner layer of the elongate inner member at least partially fills the aperture. In some embodiments, the aperture comprises a plurality of holes. In some embodiments, the distal end of the stent-engaging member comprises a cutout and wherein the pusher assembly further comprises a tube positioned around the distal end of the stent-engaging member and at least partially filling the cutout. In some embodiments, the cutout comprises a plurality of helical slots. In certain embodiments, a stent delivery device comprises an elongate outer member at least partially defining an outer member lumen, an elongate inner member coaxially positioned within the outer member lumen, and the pusher assembly. In some embodiments, the stent delivery device further comprises an atraumatic tip mechanically coupled to the stent-engaging member. In some embodiments, the elongate inner member at least partially defines a guidewire lumen, the stent-engaging member at least partially defines the guidewire lumen, and the atraumatic tip at least partially defines the guidewire lumen. In some embodiments, the atraumatic tip comprises a generally conical distal end and a generally cylindrical proximal end comprising at least one aperture in fluid communication with the outer member lumen.

In certain embodiments, a method of manufacturing a pusher assembly comprises mechanically coupling a proximal end of a stent-engaging member at least partially inside a flared distal end of an elongate inner member. The stent-engaging member comprises a portion that radially expands towards a distal end of the stent-engaging member. The stent-engaging member is configured to move a stent when distally advanced and configured to not move a stent when proximally retracted. In some embodiments, mechanically coupling comprises heat shrinking the flared distal end of the elongate inner member around the proximal end of the stent-engaging member. In some embodiments, the method further comprises forming the flared distal end of the elongate inner member. In some embodiments, forming the stent-engaging member comprising cutting, deforming, and heat setting a hypotube. In some embodiments, the stent-engaging member comprises a ratchet and a stem and wherein the method further comprises welding the ratchet to the stem.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the invention.

FIG. 2C illustrates another example embodiment of a proximal portion of the stent delivery device encircled by the line 2 in FIG. 1A;

FIG. 3D is a top elevational and partial cross-sectional view of the proximal portion of the stent delivery device illustrated in FIG. 2A;

FIG. 3E illustrates an example embodiment of a portion of the proximal portion encircled by the line 3E in FIG. 3D;

FIG. 7A illustrates an example embodiment of a stent-engaging portion;

FIG. 7B illustrates another example embodiment of a stent-engaging portion;

FIG. 7C illustrates another example embodiment of a stent-engaging portion;

FIGS. 7F and 7G illustrate another example embodiment of a stent-engaging portion;

FIGS. 9 and 10 schematically depict an example embodiment of deploying a stent in a vessel;

FIG. 11 illustrates an example embodiment of an intermediate portion of the stent delivery device encircled by the line 2 in FIG. 1;

FIG. 15C schematically depicts still another example embodiment of deploying a stent in a vessel.

DETAILED DESCRIPTION

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

Certain aspects of the delivery systems described herein are described in U.S. patent application Ser. No. 11/876,764, published as U.S. Patent Pub. No. 2008/0097572, which is incorporated herein by reference in its entirety.

Figure 1A:
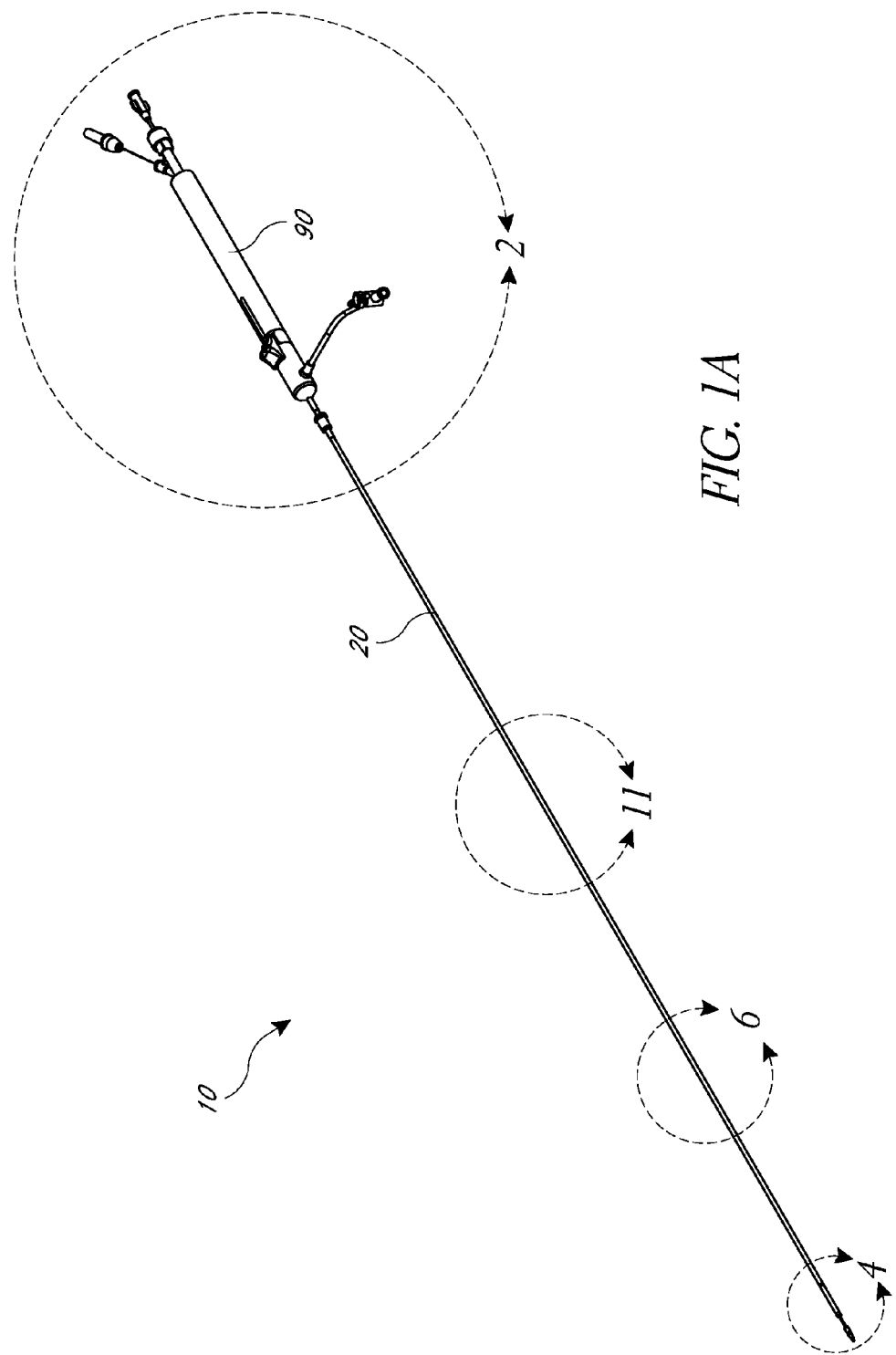
FIG. 1A illustrates an example embodiment of a stent delivery device.

FIG. 1A illustrates an example embodiment of a stent delivery device 10. The stent delivery device 10 has a proximal portion 2, one or more intermediate portions 11, 6, and a distal portion 4, each of which is described in more detail herein. The stent delivery device 10 comprises a device body or handle 90 and an outer sheath or outer member 20. In certain embodiments, the outer diameter of the outer sheath 20 is 7 French (0.092 inches; 2.3 mm). In certain embodiments, the outer diameter of the outer sheath 20 is 6 French (0.079 inches; 2.0 mm). Other diameters of the outer sheath 20 are also possible.

Figure 1B:
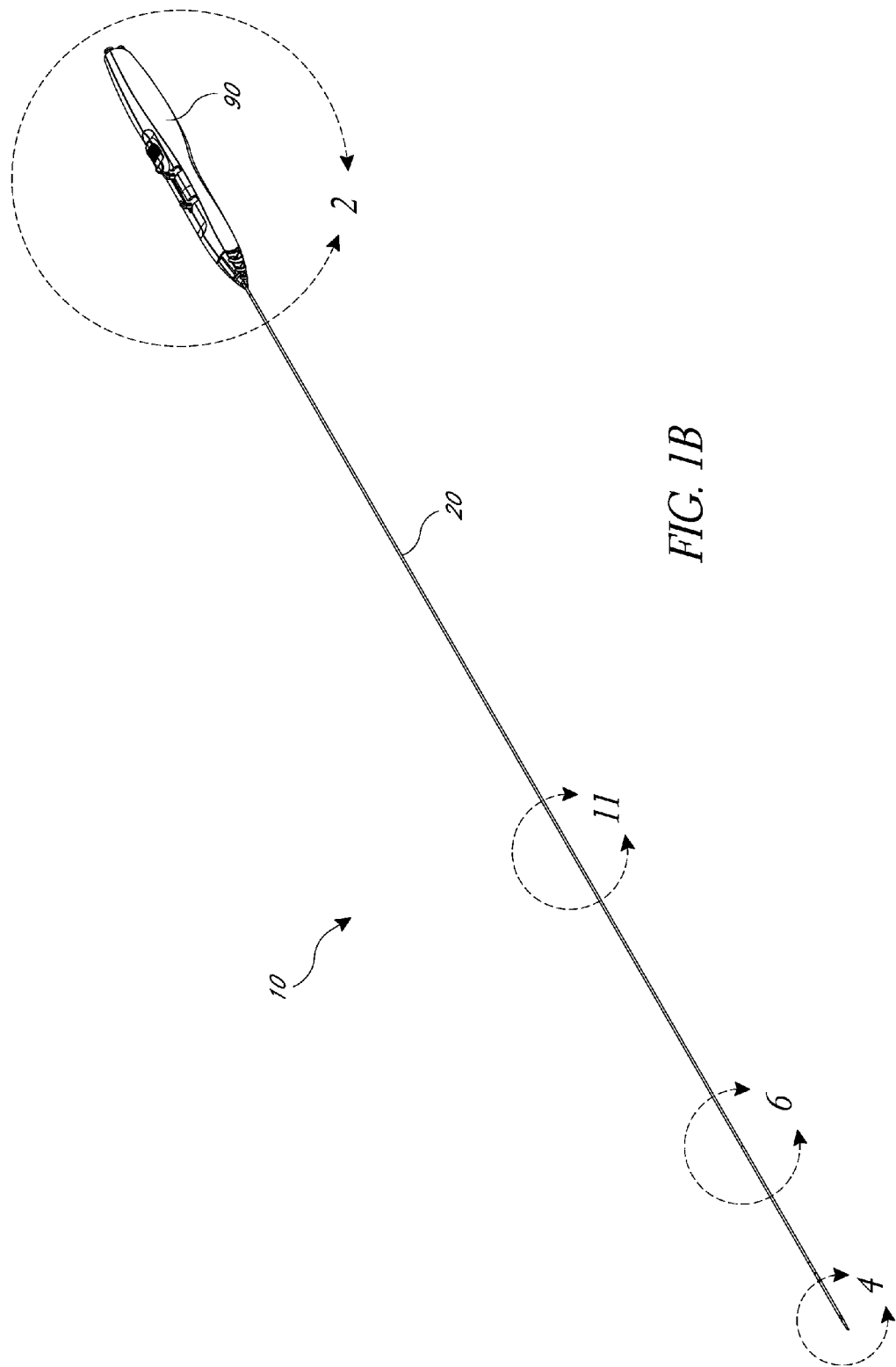
FIG. 1B illustrates another example embodiment of a stent delivery device.

FIG. 1B illustrates another example embodiment of a stent delivery device 10. The stent delivery device 10 has a proximal portion 2, one or more intermediate portions 11, 6, and a distal portion 4, each of which is described in more detail herein. The stent delivery device 10 comprises a device body or handle 90 and an outer sheath or outer member 20. In certain embodiments, the outer diameter of the outer sheath 20 is 7 French (0.092 inches; 2.3 mm). In certain embodiments, the outer diameter of the outer sheath 20 is 6 French (0.079 inches; 2.0 mm). Other diameters of the outer sheath 20 are also possible.

Figures 2A, 2B:
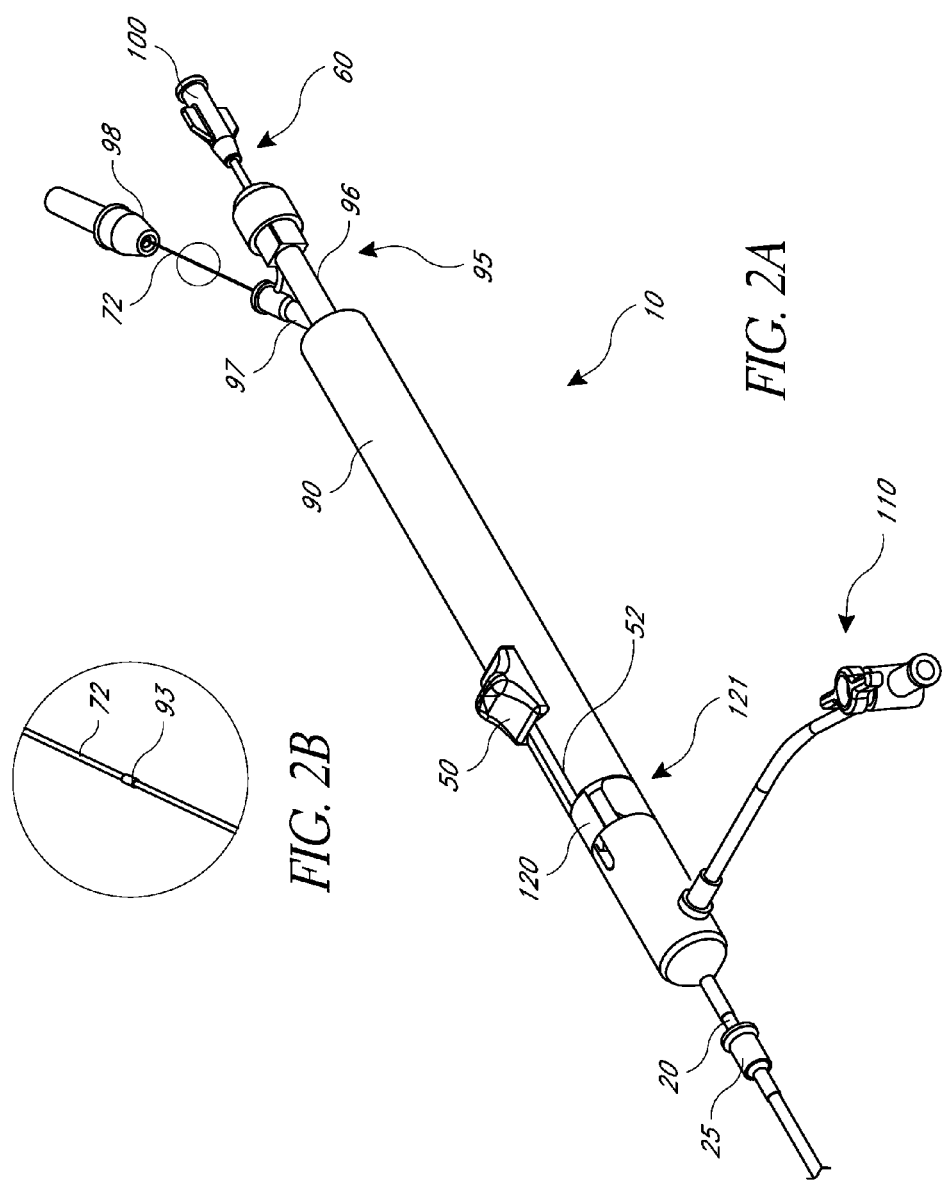
FIG. 2A illustrates an example embodiment of a proximal portion of the stent delivery device encircled by the line 2 in FIG. 1A.
FIG. 2B illustrates an example embodiment of a portion of the proximal portion encircled by the line in FIG. 2A.
Figure 2E:
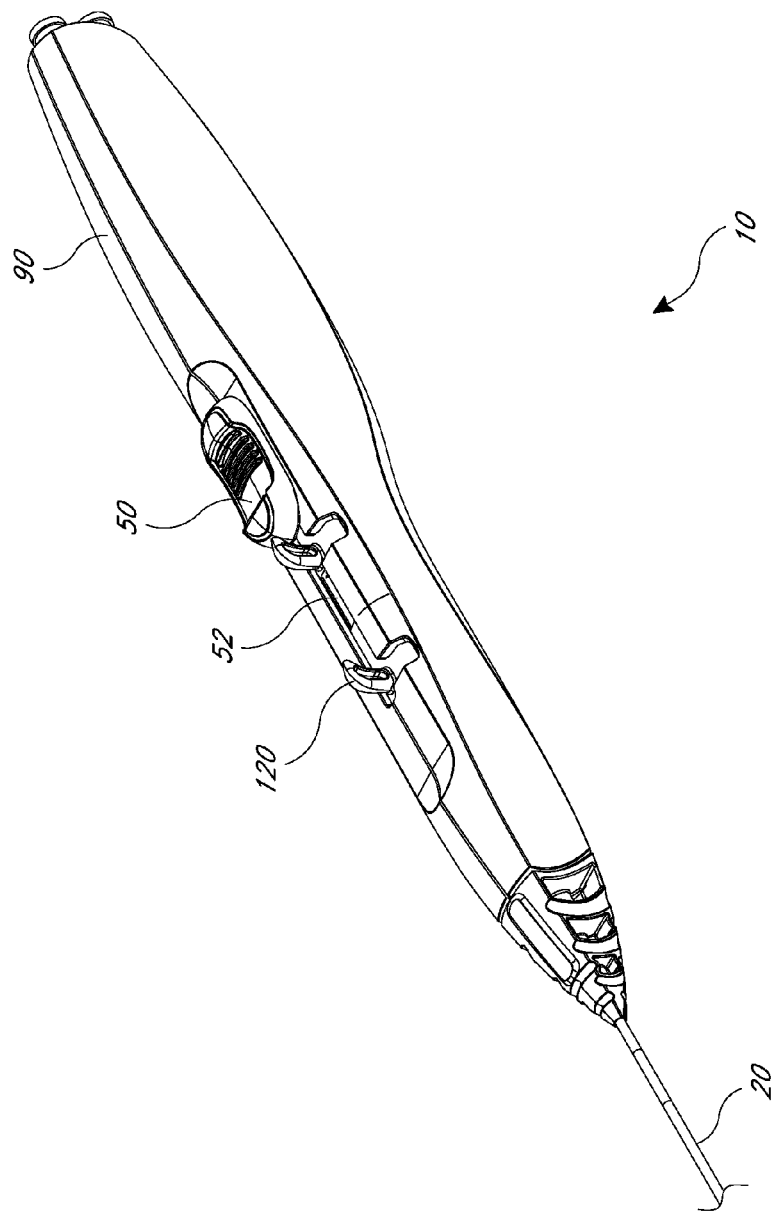
FIG. 2E illustrates an example embodiment of a proximal portion of the stent delivery device encircled by line 2 in FIG. 1B.
Figure 3A:
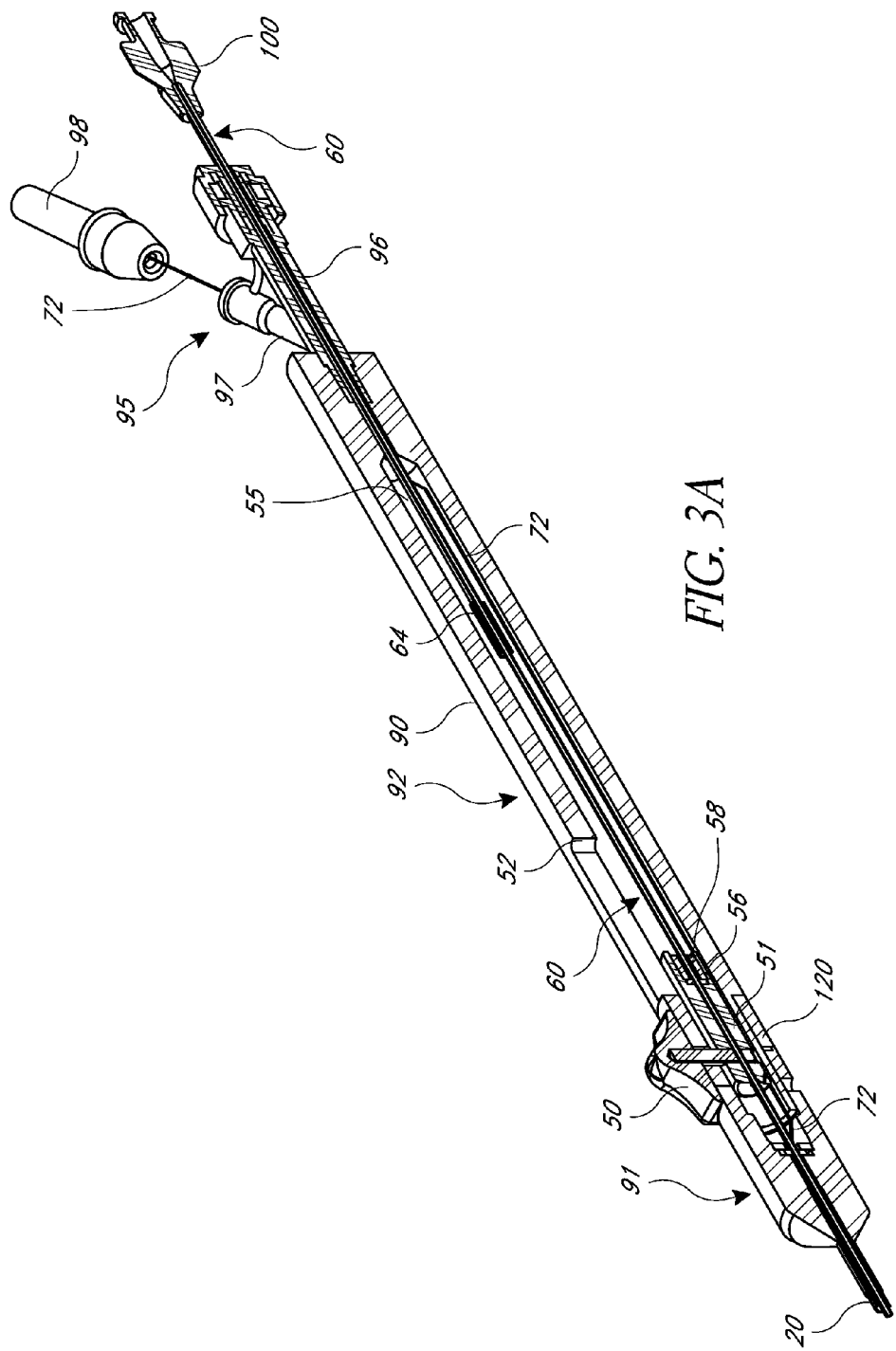
FIG. 3A is a cross-sectional view of the proximal portion of the stent delivery device illustrated in FIG. 2A.

An example embodiment of a proximal portion of the stent delivery device 10 is illustrated in perspective in FIG. 2A and in cross-section in FIG. 3A. Another example embodiment of a proximal portion of the stent delivery device 10 is illustrated in perspective in FIG. 2E and in cross-section in FIG. 3F. The stent delivery device 10 comprises user-actuatable element or switch 50 that is coupled to (and, in the embodiment illustrated in FIGS. 2A, 2E, 3A and 3F, mounted so as to be longitudinally slidable with respect to) the device body or handle 90. The switch 50 is also coupled to an element 40 (FIG. 3C), which in the embodiment illustrated in FIGS. 2A, 2E, 3A and 3F has a passageway and is configured to fit within the outer sheath 20. The switch 50 is slidably mounted on the device body 90 and coupled to the element 40 via a block 51. In some embodiments, the block 51 may include a biasing element (e.g., a spring) that biases the switch 50 toward the position shown in FIG. 3A or 3F. In some embodiments, the block 51 does not include a biasing element.

The switch 50, block 51, and element 40 of the device 10 are movable in the proximal and distal directions (which are along the longitudinal axis (not shown) of the device 10), and are generally constrained in other directions. Thus, proximal movement of the switch 50 (towards the proximal side 92) results in proximal movement of the element 40, and distal movement of the switch 50 (towards the distal side 91) results in distal movement of the element 40. In some embodiments, the distance that the switch 50 moves (either proximally or distally) translates into movement of the element 40 by the same distance. In some embodiments, the distance that the switch 50 moves (either proximally or distally) translates into movement of the element 40 by a different distance (e.g., by being geared up or down). As explained in greater detail herein, the element 40 is coupled to a stent-engaging element 45, which engages and drives a loaded stent 30 distally from the outer sheath 20 during at least a portion of the time that the switch 50 is operated distally.

Figure 2D:
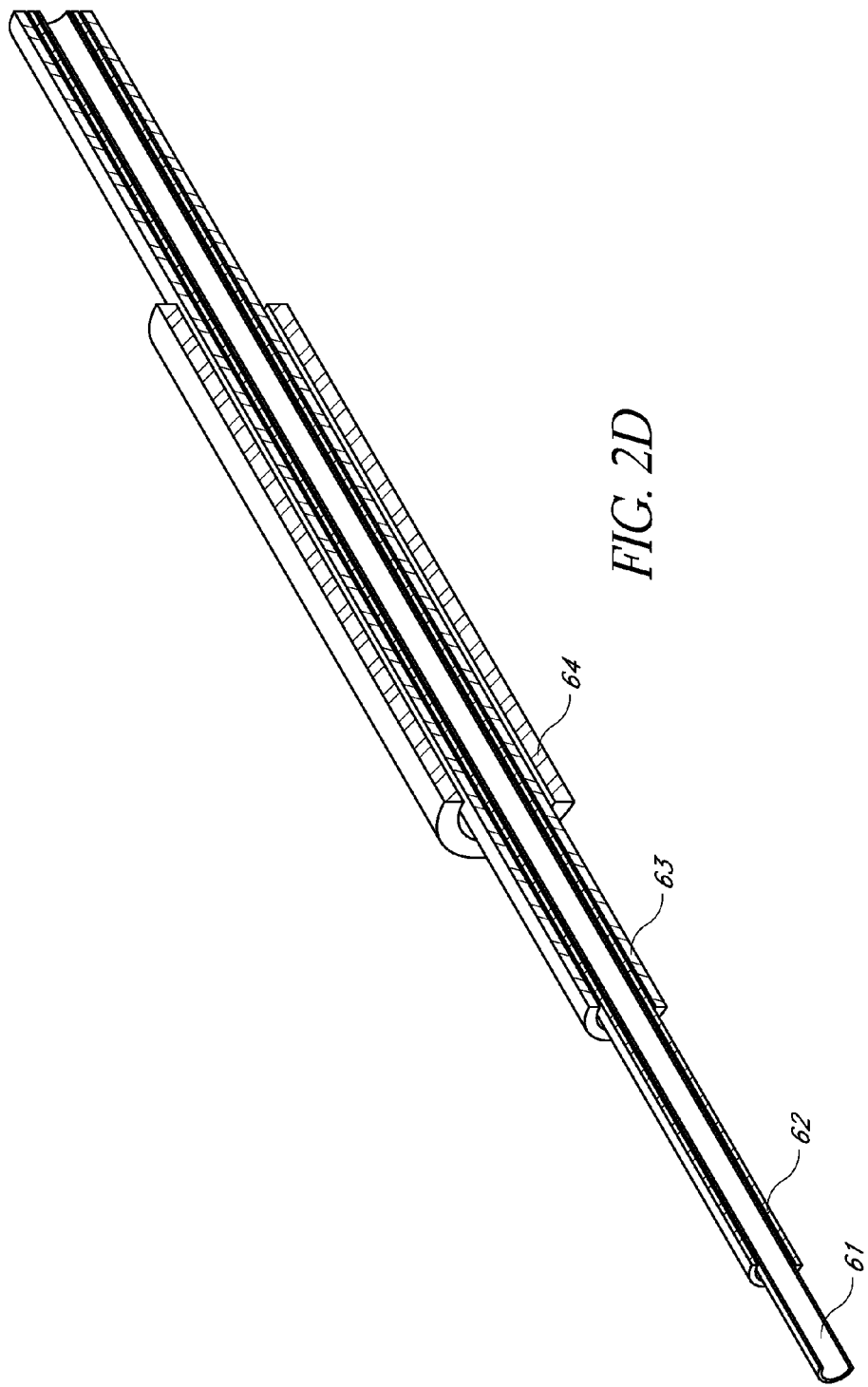
FIG. 2D illustrates an example embodiment of an inner member.
Figure 4A:
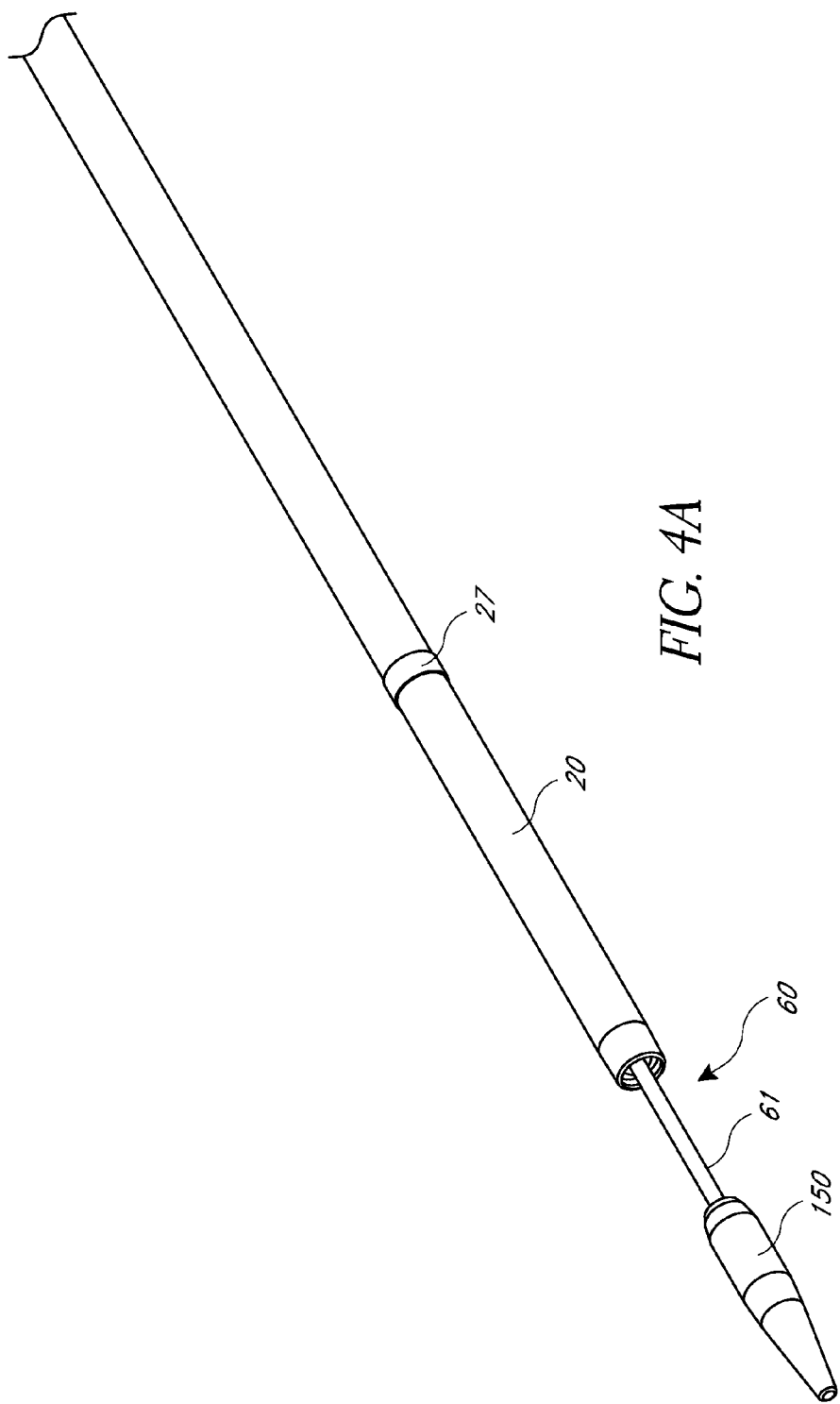
FIG. 4A illustrates an example embodiment of a distal portion of the stent delivery device encircled by the line 4 in FIG. 1.

The outer sheath 20 extends distally from device body 90. The device 10 can also include inner member 60, a portion of which is located within (e.g., coaxially positioned within) the outer sheath 20. As illustrated in, for example, FIG. 4A, the inner member 60 (and, in certain embodiments such as illustrated in FIG. 2D, an inner sleeve 61) is coupled at its distal end to an atraumatic tip or nose cone 150. The inner member 60, which is not constrained axially by the outer sheath 20 (e.g., because the inner diameter of the outer sheath 20 is sufficiently different from the outer diameter of the inner member 60 that they do not necessarily touch), facilitates motion of the nose cone 150 relative to the outer sheath 20. The inner member 60 at least partially defines a guidewire lumen through which a guidewire (e.g., having a diameter of 0.018 inches (approx. 0.46 mm)) may be passed. The nose cone 150 at least partially defines the guidewire lumen through which a guidewire (e.g., having a diameter of 0.018 inches (approx. 0.46 mm)) may be passed.

A radiopaque marker 27 may be placed at any suitable location along the outer sheath 20 to provide a means for aiding deployment of a stent 30. For example, the distance from the distal end of the outer sheath 20 and the marker 27 may be the nominal length of the stent 30 being delivered in its deployed state.

Figure 4B:
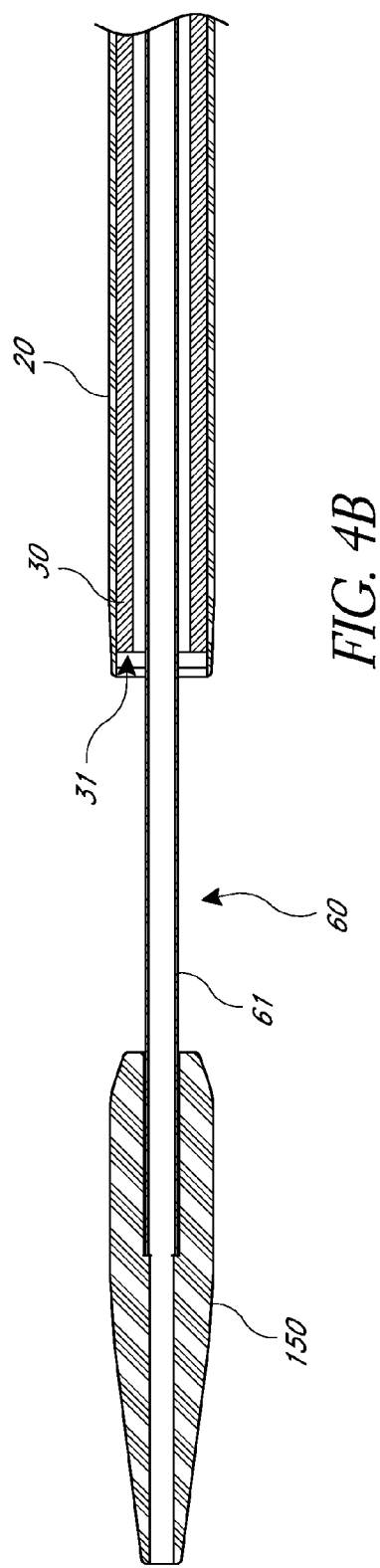
FIG. 4B is a cross-sectional view of the distal portion of the stent delivery device illustrated in FIG. 4A.

FIG. 4B illustrates the distal end 31 of the stent 30 within the outer sheath 20. In some embodiments, neither the element 40 nor the stent-engaging member 45 is attached to inner member 60. In certain such embodiments, the element 40 may be moved proximally and over the inner member 60 while the inner member 60 is stationary, and the stent-engaging member 45 may be moved proximally and distally over the inner member 60 while the inner member 60 is stationary.

Referring to FIGS. 2A, 2C, 2E, 3A, and 3F, the allowable proximal-distal travel of the switch 50 is constrained by the length of a slot 52 in the device body 90, as well the position of one or more stoppers 120. The first position 121 of the stopper 120 shown in FIGS. 2A and 2E limits the distal travel of the switch 50 to less than the full length of the slot 52. In some embodiments, the first position 121 corresponds to a distal-most position of the switch 50 in which the stent-engaging member 45 remains within the outer sheath 20. This corresponds to an example configuration for advancement of the stent 30. The stopper 120 is preferably biased to the first position 121 with, e.g., a spring. In FIGS. 2C and 3A, the stopper 120 has been rotated to a second position 122 that allows the switch 50 to slide past the stopper 120.

FIG. 2D is a cross-sectional view of a sub-assembly of an example embodiment of the device 10 that includes an example embodiment of the inner member 60 in the form of an inner sleeve 61 that extends the length of the inner member 60 and that is configured to accept a guidewire (not shown). In some embodiments, the inner member 60 includes an intermediate sleeve 62 that may be secured at its distal end or any other suitable location to the inner sleeve 61 in any suitable fashion, such as by Loctite® 4014 adhesive. The intermediate sleeve 62 (e.g., comprising a hypotube) may also extend to the proximal end of the inner member 60. In some embodiments, the inner member 60 includes an outer sleeve 63 (e.g., comprising a hypotube) connected at its distal end or any other suitable location to the intermediate sleeve 62 in any suitable manner (e.g., soldering). The outer sleeve 63 may also extend to the proximal end of the inner member 60. In some embodiments, the inner member 60 includes a travel-limiting sleeve 64 connected at its distal end or any other suitable location to the outer sleeve 63 in any suitable manner (e.g., soldering). The sleeve 64 may be configured to restrict the travel of the inner member 60 with respect to the device body 90. The sleeve 64 can be configured to interfere (e.g., due to its size) with the proximal opening of a cavity 55 of the device body 90 (e.g., as illustrated in FIG. 3A). The sleeve 64 can be configured to interfere distally with the block 51 (e.g., if a Luer fitting 100 does not first interfere with the Y-adapter 95).

Figure 3B:
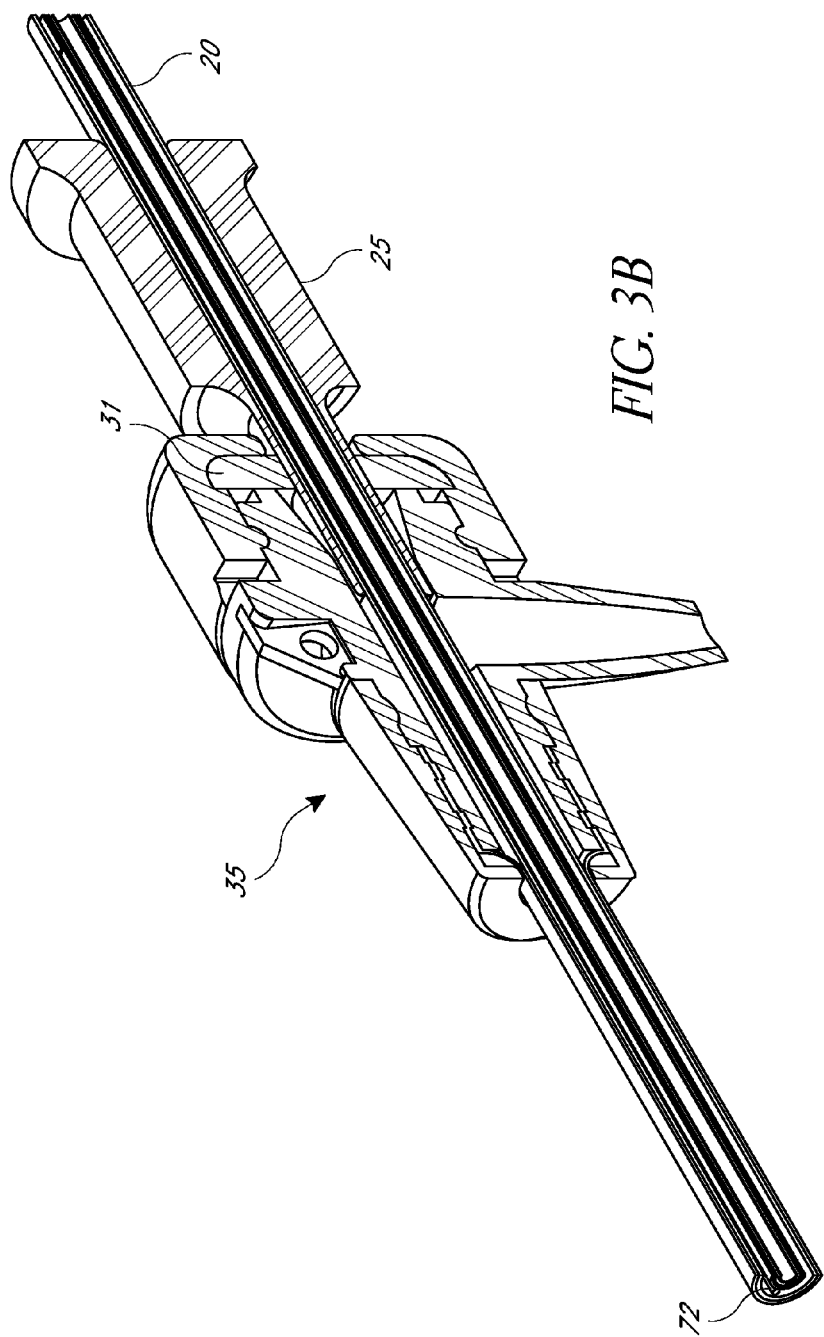
FIG. 3B is a cross-sectional view of an example embodiment of a portion of the proximal portion of the stent delivery device illustrated in FIG. 2A.

FIG. 3B is an enlarged, cross-sectional view, showing the interaction between the element 25 and a seal 31 of the hemostasis valve of the introducer 35. In certain embodiments, the device 10 includes an element 25 that is coupled (e.g., slidably coupled) to the outer sheath 20. In some embodiments, the element 25 is configured to slide relatively freely along the outer surface of the outer sheath 20. In certain such embodiments, the element 25 is configured to interface with a hemostasis valve of an introducer 35. The element 25 be configured to fit at least partially inside the introducer 35 and to interface with the hemostasis valve such that fluid does not flow back toward the handle 90 of the device 10, but still allows the outer sheath 20 of the device to slide relatively freely within the element 25 and the introducer 35. The element 25 can reduce the friction between the outer sheath 20 of the device 10 and an introducer 35 through which the outer sheath 20 of the device 10 is inserted, while maintaining a substantial fluid seal between the outer sheath 20 and the exterior of the patient.

Figure 3C:
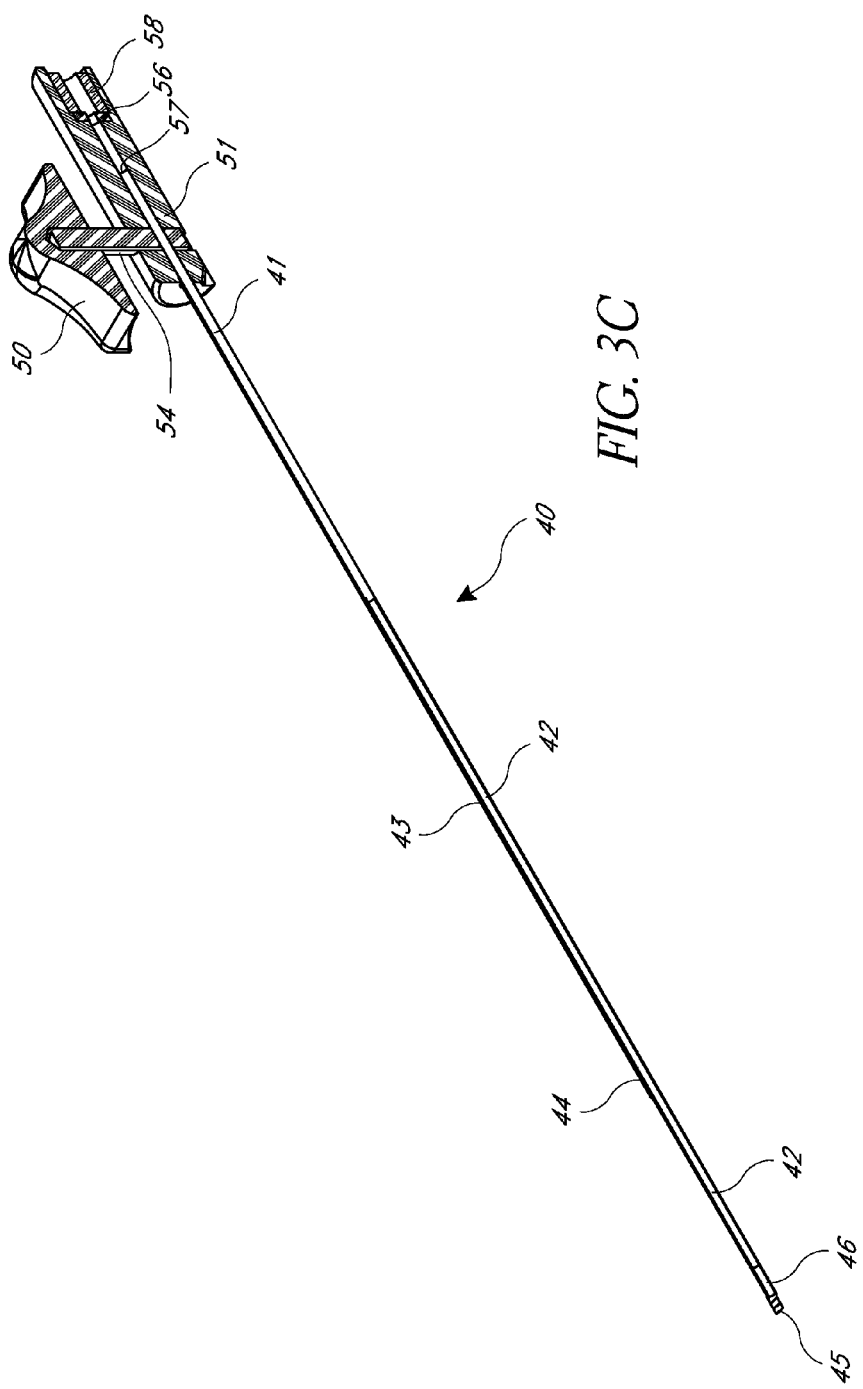
FIG. 3C is a cross-sectional view of an example embodiment of portions of the stent delivery device illustrated in FIG. 1.
Figure 3F:
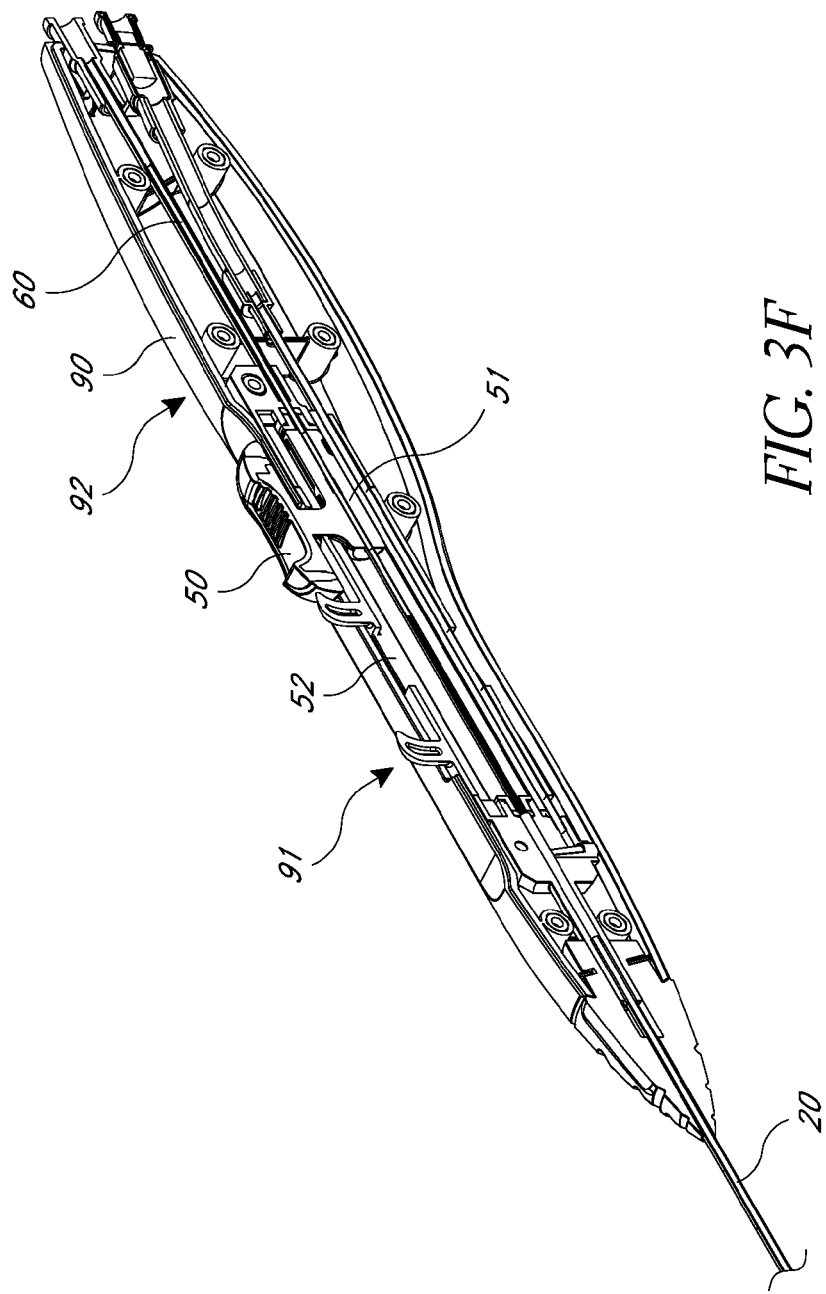
FIG. 3F is a cross-sectional view of an example embodiment of a portion of the proximal portion of the stent delivery device illustrated in FIG. 2E.

FIG. 3C is a cross-sectional view of a sub-assembly of an example embodiment of the device 10 that includes an example embodiment of the element 40 comprising a proximal hypotube 41 secured in any suitable fashion to block 51, such as by a press fit that terminates at a shoulder 57 or with a suitable adhesive, such as one of the Loctite® adhesives (e.g., 4014, 4305, 3321, etc.). The block 51 is secured to the switch 50 through a pin 54, which can be bonded to the switch 50 and press fit or bonded to the block 51. The element 40 may also include an intermediate tube 42 that is connected at its proximal end to a proximal hypotube 41 in any suitable manner, such as through Loctite® 4305, and at its distal end to a support tube or stem 46 (that is in turn connected to stent-engaging member 45). In some embodiments, the element 40 includes a support tube 43 positioned over an intermediate tube 42 and abuts the distal end of the proximal hypotube 41.

In certain embodiments, a support tube 43 is connected at any suitable location to the intermediate tube 42 (e.g., using any suitable adhesive). The support tube 43 may be configured to increase the rigidity of the intermediate tube 42.

The element 40 may also include a resheathing stop 44 that is threaded over the intermediate tube 42 and that abuts the distal end of the support tube 43. The resheathing stop 44 may be connected at any suitable location to intermediate tube 42 using any suitable adhesive. The resheathing stop 44 may be configured to prevent proximal movement of a stent 30 enclosed by outer sheath 20 if the stent 30 is re-sheathed during the delivery process. The sub-assembly illustrated in FIG. 3C also includes a seal 56 (e.g., comprising silicone) designed to reduce (e.g., prevent) the backflow of fluid around the outside of the inner member 60, and an outer hypotube in certain embodiments of inner member 60, and that is held in place by a retainer 58 (e.g., comprising stainless steel).

Figure 6:
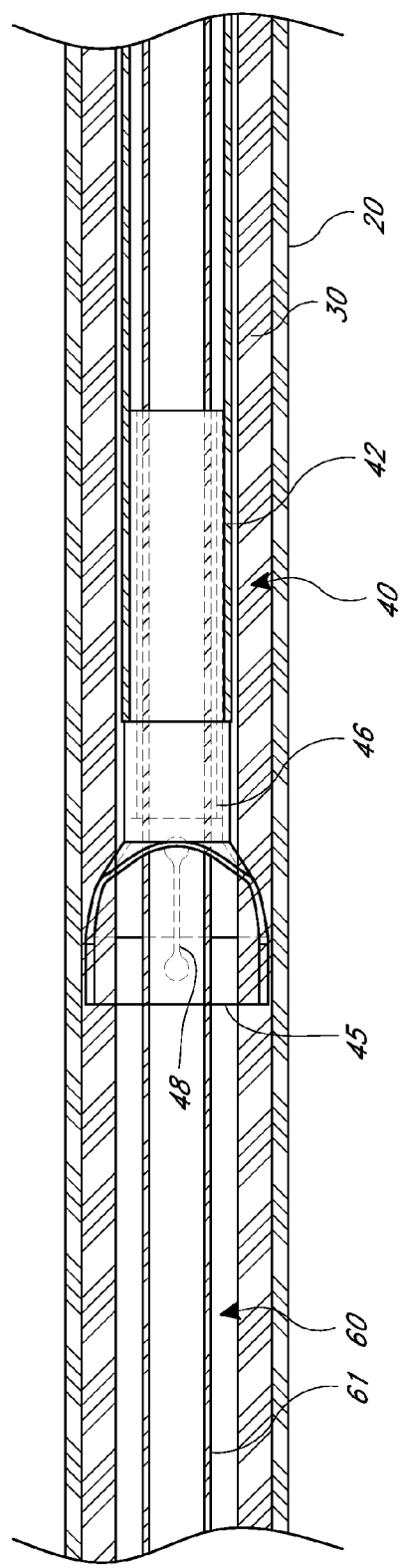
FIG. 6 illustrates an example embodiment of an intermediate portion of the stent delivery device encircled by the line 6 in FIG. 1.

FIG. 6 illustrates an element 40 extending such that a portion of it is located within the outer sheath 20. In some embodiments, the element 40 is hollow and its passageway accommodates a portion of inner member 60 being located within it. Some embodiments of the element 40 may be non-hollow.

Figure 5A:
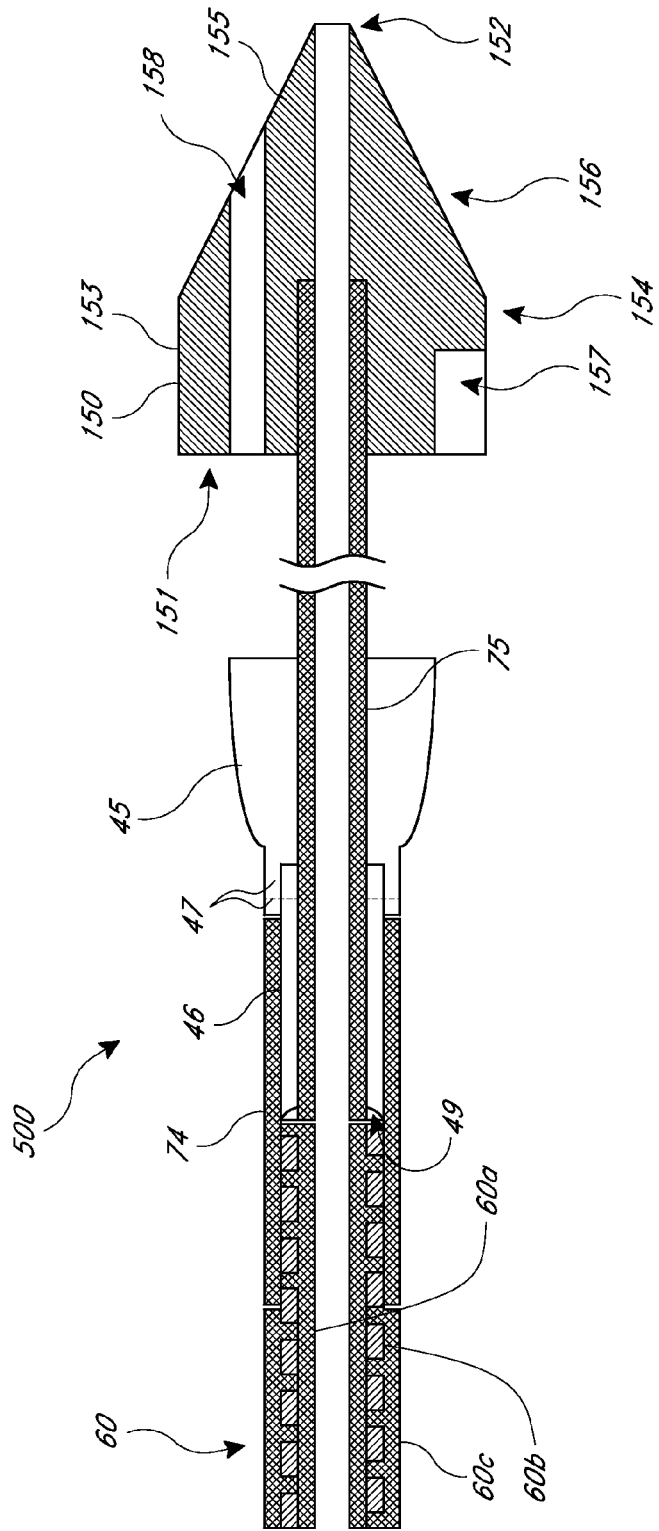
FIG. 5A is a cross-sectional view of an example embodiment of a pusher assembly.

FIG. 5A schematically illustrates an example embodiment of a pusher assembly or ratchet assembly 500. The pusher assembly 500 includes the distal end of the inner member 60, a stent-engaging member 45, and a connector 74. The proximal end of the stent-engaging member 45 is proximate to the distal end of the inner member 60. The connector 74 mechanically couples the distal end of the inner member 60 to the proximal end of the stent-engaging member 45.

In certain embodiments, the inner member 60 comprises three layers: (1) an inner layer 60*a* (e.g., comprising nylon); (2) a middle layer 60*b* (e.g., comprising braided stainless steel ribbons); and (3) an outer layer 60*c* (e.g., comprising nylon). In some embodiments, the distal end of the inner member 60 comprises the inner layer 60*a* and the middle layer 60*b*. In certain such embodiments, the outer layer 60*c* is removed (e.g., milled, stripped, etched) from the distal end of the inner member 60.

FIGS. 7A-7G illustrate example embodiments of a stent-engaging member 45. The stent-engaging member 45 includes a portion that radially outwardly extends towards the distal end of the stent-engaging member 45. In the embodiments illustrated in FIGS. 7A, 7B, 7F, and 7G, the stent-engaging member 45 includes a portion that has a shovel or scoop shape having a curved distal end. In the embodiment illustrated in FIGS. 7C and 7D, the stent-engaging member 45 includes a portion that has a shovel or scoop shape having a flat distal end. In some embodiments, the stent-engaging member 45 may be formed into shape by cutting (e.g., laser cutting), deforming, and heat setting a hypotube (e.g., comprising a nickel-titanium alloy). For example, FIGS. 7A-7D, 7F, and 7G depict a generally cylindrical handle portion and a cut, deformed, and heat set shovel-shaped or scoop-shaped portion that radially outwardly extends towards the distal end of the stent-engaging member 45.

Figure 7D:
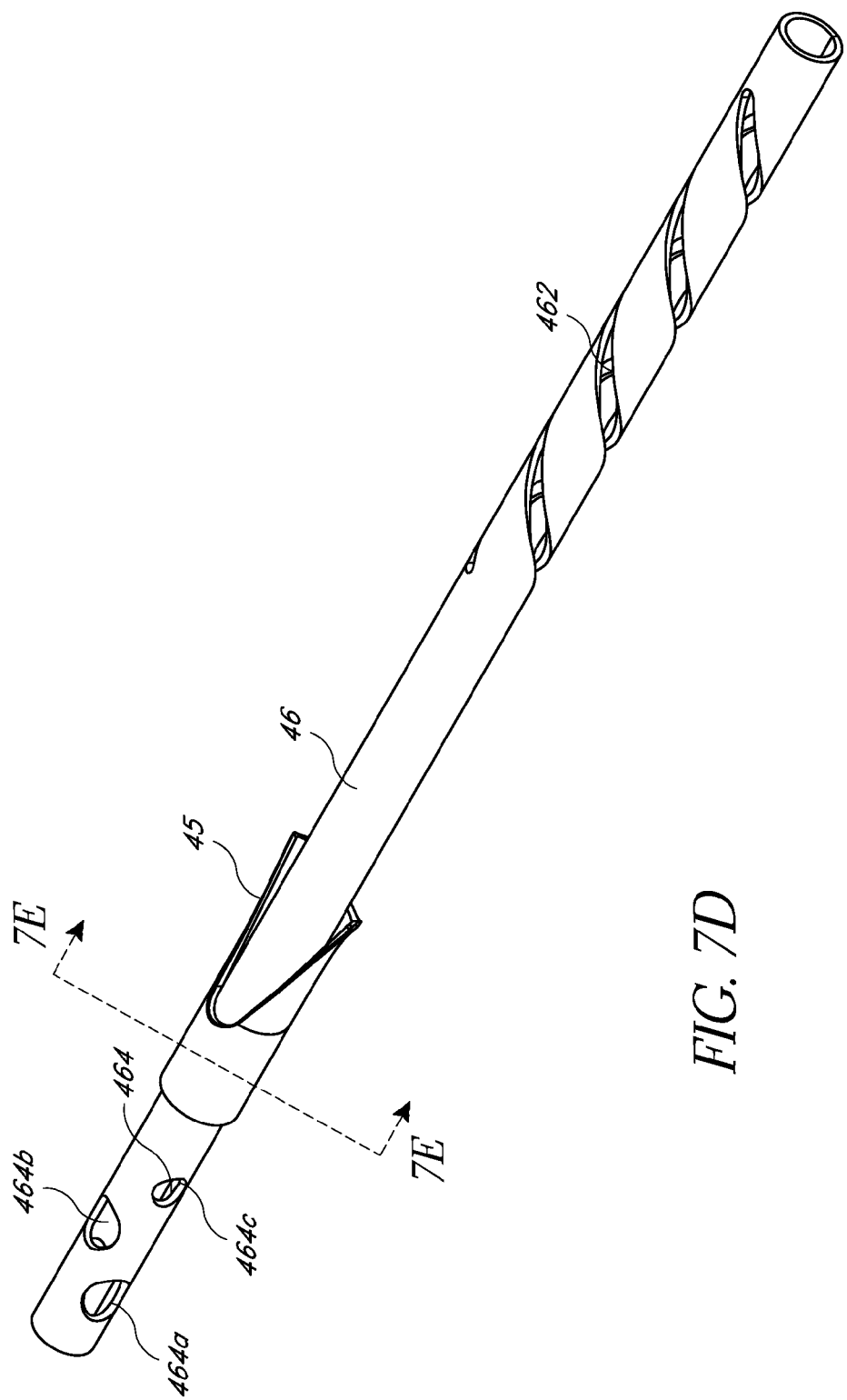
FIG. 7D illustrates another example embodiment of a stent-engaging portion.
Figure 7E:
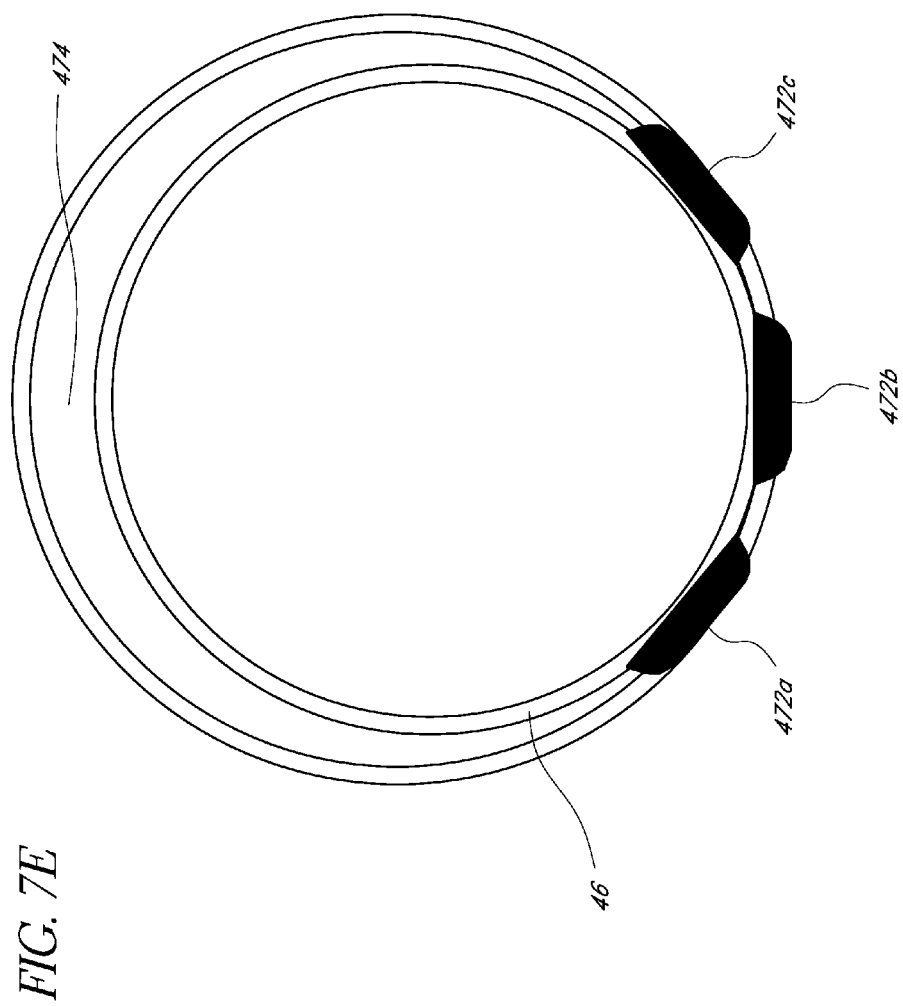
FIG. 7E illustrates an example cross-sectional view of the stent-engaging portion of FIG. 7E along the line 7E-7E.

FIG. 7B illustrates an embodiment of a stent-engaging member 45 comprising a flex slot 48 configured to alleviate fatigue stress fractures and the like and to allow the stent-engaging member 45 to more easily deform inwardly as the stent-engaging member slides proximally within the lumen of a stent 30. In some embodiments, the flex slot 48 has a dumbbell or dog bone shape. In some embodiments, the flex slot 48 is formed during cutting a hypotube. Other shapes of flex slots are also possible. Combinations of flex slots with other stent-engaging members 45 (e.g., the stent-engaging members 45 illustrated in FIGS. 7A, 7C, 7D, 7F, and 7G) are also possible.

In some embodiments, the stent-engaging member 45 comprises a stem 46 and a ratchet mechanically coupled to the stem 46. The stem 46 may comprise a hypotube (e.g., comprising a nickel-titanium alloy) having a smaller outer diameter than the diameter of the ratchet. Referring again to FIGS. 5A and 5B, the stem 46 may have a concave or scalloped proximal surface 49 that can reduce stress when the stent-engaging member 45 is mechanically coupled to the distal end of the inner member 60. In some embodiments, the outer diameter of the stem 46 is substantially similar to the inner diameter of the ratchet. In some embodiments, the outer diameter of the stem 46 is substantially equal to the outer diameter of the middle layer 60b of the inner member 60.

In some embodiments, the stem 46 comprises a portion configured to enhance bonding with a polymer. FIG. 7A illustrates an example embodiment of a stent-engaging member 45 comprising stem 46 comprising a cutout 460. In some embodiments, the cutout 460 is laser cut. In some embodiments, the cutout 460 may be deformed and heat set after cutting (e.g., to inwardly bias projections in the cutout 460). Other shapes of cutouts are also possible. Combinations of stems 46 with a cutout 460 with other shapes (e.g., the shapes illustrated in FIGS. 7B-7D, 7F, and 7G) are also possible.

FIG. 7D illustrates an example embodiment of a stent-engaging member 45 comprising a stem 46 comprising a plurality of apertures 464. In some embodiments, the apertures 464 are laser cut. In some embodiments, the plurality of apertures 464 comprises three through-holes or six individual holes. In certain embodiments, the plurality of apertures 464 comprises a first through-hole 464a, a second through-hole 464b, and a third through-hole 464c. The first through-hole 464a and the second through-hole 464b are circumferentially aligned and longitudinally spaced. The third through-hole 464c is rotated about 90° circumferentially from the first through-hole 464a and the second through-hole 464b. The third through-hole 464c is longitudinally between the first through-hole 464a and the second through-hole 464b. The third through-hole 464c may include portions that longitudinally overlap with potions of the first through-hole 464a and/or the second through-hole 464b. Other numbers of apertures 464 and orientations of apertures 464 are also possible (e.g., apertures that are not through-holes, apertures that are circumferentially offset by about 30°, about 45°, about 60°, about 90°, about 120°, about 135°, about 150°, about 180°, and ranges therebetween, apertures that are longitudinally offset, etc.).

In some embodiments, combinations of cutouts 460 and apertures 464 may be used and/or substituted for each other. For example, the stem 46 of the stent-engaging member 45 illustrated in FIG. 7A or 7B may comprise the plurality of apertures 464 illustrated in FIG. 7D. For another example, the stem 46 of the stent-engaging member 45 illustrated in FIG. 7D may comprise the cutout 460 illustrated in FIG. 7A.

In some embodiments, the stem 46 extends through the ratchet, for example to a length beyond the distal end of the ratchet. For example, FIG. 7D illustrates an example embodiment of a stent-engaging member 45 comprising a stem 46 extending through the ratchet to a length beyond the distal end of the shaped portion of ratchet.

In some embodiments, the stem 46 comprises a laser cut 462 proximate to the distal end, for example configured to increase the flexibility of the stem 46. In some embodiments, the laser cut 462 comprises one or more helices. For example, the laser cut 462 may comprise a first helix winding in a first direction and starting a first circumferential position and a second helix also winding in the first direction but starting in a second circumferential position (e.g., about 180° from the first circumferential position).

In some embodiments, the stem 46 is mechanically coupled to the ratchet by two longitudinally-spaced arcuate welds (e.g., laser welds). For example, FIGS. 5A and 7A illustrate two longitudinally-spaced arcuate (e.g., fully circumferential) welds 47 coupling the ratchet to the stem 46. In some embodiments, the arcuate welds begin at about the same circumferential position. In some embodiments, the stem 46 is mechanically coupled to the ratchet by a plurality of arcuately-spaced spot welds (e.g., laser welds). For example, FIG. 7E, which is a cross-section taken along the line 7E-7E in FIG. 7D, illustrates three arcuately-spaced spot welds 472a, 472b, 472c coupling the ratchet to the stem 46. Other numbers of spot welds are also possible (e.g., five or less, three or less, 1, etc.). In some embodiments, the welds 472a, 472b, 472c are spaced by about 30°, about 45°, about 60°, about 75°, about 90°, about 120°, and ranges therebetween, in which the angles may be measured between lines connecting the welds 472a, 472b, 472c and a common spot (e.g., the center of the stem 46, the center of the ratchet, or elsewhere). For example, in the embodiment illustrated in FIG. 7E, the weld 472a is spaced from the weld 472c by about 90°, and the weld 472b is spaced from the welds 472a, 472c by about 45°.

When a first weld is made (e.g., the weld 472b), the stem 46 is pulled off-center of the ratchet at the point of the weld 472b. This pulling can create a gap 474 between the ratchet and the stem 46 at the opposite side. In an arcuate weld, the connection between the ratchet and the stem 46 can become worse as the weld approaches the largest distance of the gap 474, perhaps even to the extent that portions of the weld may have no coupling effect. A plurality of spot welds may produce at least as much coupling effect as an arcuate weld, may reduce processing time, and may produce a more robust coupling. In the embodiment depicted in FIG. 7E, the welds 472a, 472b, 472c each have a coupling effect between the ratchet and the stem 46. In embodiments in which the ratchet has a side with more material (e.g., the shovel or scoop portion of the ratchets illustrated in FIGS. 7A-7D), the spot welds 472a, 472b, 472c may be made on that side to provide additional room for error (e.g., longitudinal welding error). In certain embodiments, the gap 474 may be at least partially filled (e.g., by a polymer).

Figure 7G:
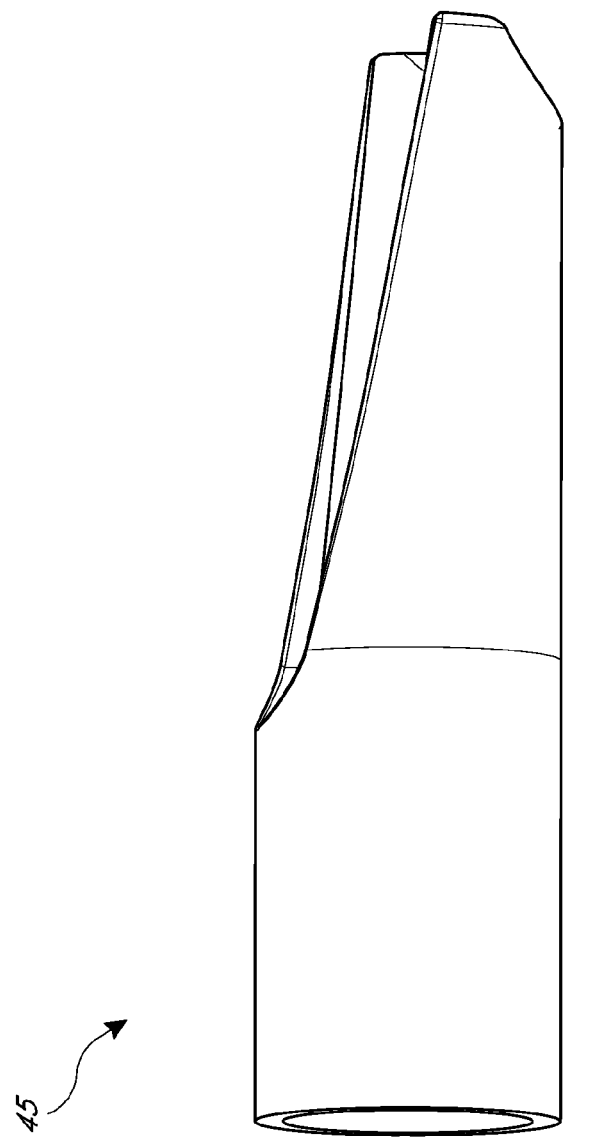

FIGS. 7F and 7G illustrate another example embodiment of a stent-engaging member 45. The stent-engaging member 45 includes a portion that radially outwardly extends towards the distal end of the stent-engaging member 45. In the embodiment illustrated in FIG. 7D, the stent-engaging member 45 includes a portion that has a shovel or scoop shape having a curved distal end and distally and/or outwardly flared tips 452. In some embodiments, the stent-engaging member 45 may be formed into shape by cutting (e.g., laser cutting), deforming, and heat setting a hypotube (e.g., comprising a nickel-titanium alloy). FIGS. 7F and 7G depict a generally cylindrical handle portion and a cut, deformed, and heat set flared-tip shovel-shaped or scoop-shaped portion that radially outwardly extends towards the distal end of the stent-engaging member 45.

FIG. 5A illustrates an example embodiment in which the proximal end of the stent-engaging member 45 is mechanically coupled to the distal end of the inner member 60 at a slightly spaced butt joint. A connector 74 (e.g., comprising a tubular member (e.g., comprising nylon)) is heat shrunk (e.g., by being radially inwardly compressed by a heat shrink sleeve) around the distal end of the inner member 60 and around the proximal end of the stent-engaging member 60. In some embodiments, portions of the connector 74 may seep into the gap between the inner member 60 and the stent-engaging member 45. In certain embodiments, the distal end of the inner member may be modified prior to the mechanical coupling (e.g., by removing the outer layer 60c).

In some embodiments, the outer diameter of the connector 74 is substantially equal to the outer diameter of the inner member 60. In some embodiments, the inner diameter of the connector 74 is substantially equal to the outer diameter of the middle layer 60b of the inner member 60. When both conditions are satisfied, the proximal section of the connector 74 may effectively take the place of a removed outer layer 60c.

In some embodiments, the outer diameter of the connector 74 is substantially equal to the outer diameter of a portion of the stent-engaging member 45 that does not radially outwardly extend towards the distal end of the stent-engaging member 45 (e.g., the cylindrical portion of a hypotube described herein). In some embodiments, the inner diameter of the connector 74 is substantially equal to the outer diameter of a stem 46. When both conditions are satisfied, the distal section of the connector 74 may provide a substantially seamless surface between the connector 74 and the stent-engaging member 45. When also combined with the conditions in the preceding paragraph, the connector 74 can provide the pusher assembly 500 with a substantially uniform outer diameter other than the portion of the stent-engaging member 45 that radially outwardly extends. This may provide a uniform appearance to the pusher assembly 500. Thus may also reduce the chances of portions of the pusher assembly 500 other than the radially outwardly extending portion of the stent-engaging member 45 interacting with a stent 30 and/or the outer sheath 20 (e.g., becoming undesirably snagged).

Figure 5B:
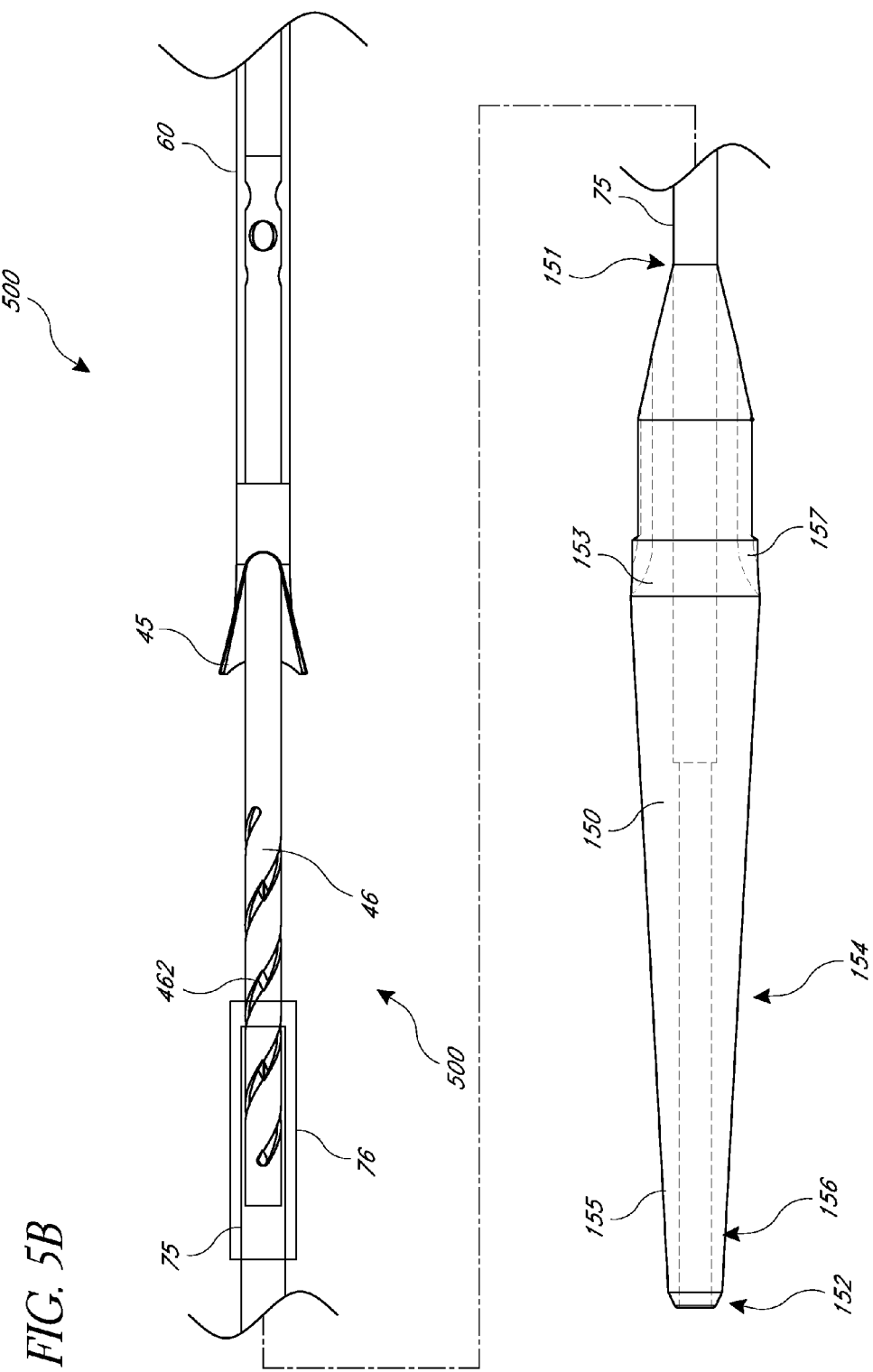
FIG. 5B is a cross-sectional view of another example embodiment of a pusher assembly.

FIG. 5B illustrates another example embodiment in which the proximal end of the stent-engaging member 45 is mechanically coupled to the distal end of the catheter shaft or inner member 60. The distal end of the inner member 60 is flared, for example using a tool having an outer diameter that is approximately the outer diameter of the proximal end of the stent-engaging member 45. The proximal end of the stent-engaging member 45 (e.g., comprising a cutout 462 or apertures 464) is placed in the flared distal end of the inner member 60. Heat shrink tubing or other means may be used to radially inwardly force the inner member 60 to collapse around the stent-engaging member 45. Portions of the inner layer of the inner member 60 extrude into the cutout 462 or apertures 464. The coupled structure has a uniform inner diameter based on the inner diameter of the inner member 60 and the inner diameter of the stent-engaging member 45. The coupled structure may advantageously have no discrete sheer plane. The coupled structure may have a slight outward flare, for example along the portion of the stent-engaging member 45 proximal to the proximal end of the ratchet. This coupling structure may advantageously simplify manufacturing by using fewer discrete pieces (e.g., not using a connector 74), not modifying the inner member 60 (e.g., not removing the layer 60c), and/or not modifying the stem 46 (e.g., not forming the scallop 49).

The stent-engaging member 45 is configured to engage a stent 30 when distally advanced and is configured to not engage a stent when proximally retracted. For example, the radially outwardly extending portion of the stent-engaging member 45 may be configured to engage one or more intersections between filaments of a woven stent (e.g., a first intersection between filaments on a first side and a second intersection between filaments on a second opposite side, as depicted by the engagement at 33 in FIG. 5D). For another example, the radially outwardly extending portion of the stent-engaging member 45 may be configured to engage one or more cutouts in a laser cut hypotube stent. For additional examples, the radially outwardly extending portion of the stent-engaging member 45 may be configured to engage one or more engageable features of other types of stents (e.g., comprising metal, plastic, combinations thereof, etc.) and the radially outwardly extending portion of the stent-engaging member 45 may be configured to engage one or more engageable features of a graft (e.g., comprising an inner stent surface), combinations thereof, and the like.

In some embodiments, the pusher assembly 500 comprises a tube 75 (e.g., comprising nylon) positioned inward of the stent-engaging member 45 and extending from proximate to the distal end of the inner member 60 to distal to the distal end of the stent-engaging member 45. For example, as illustrated in FIG. 5A, the tube 75 extends from approximately the proximal end of the stent-engaging member 45, through the stent-engaging member 45, and for some length beyond the stent engaging member 45.

In some embodiments, the pusher assembly 500 optionally comprises a second tube 76 (e.g., comprising polyimide) radially outward of the tube 75 proximate to the portion of the tube 75 within the radially outwardly extending portion of the stent-engaging member 45, for example to protect the tube 75 from being damaged by any sharp edges of the stent-engaging member 45. In certain such embodiments the second tube extends from the proximal end of the radially outwardly extending portion of the stent-engaging member 45 to the distal end of the stent-engaging member 45.

In some embodiments, an atraumatic tip 150 is mechanically coupled to the distal end of the tube 75 and is longitudinally spaced from the distal end of the stent-engaging member 45. The tip 150 has a proximal end 151 and a distal end 152. FIGS. 5A and 5B are schematic, so the longitudinal spacing of the stent-engaging member 45 and the tip 150 may not be accurately depicted (e.g., as implied by the curved pairs of lines across the tube 75). In some embodiments, the distal end of the stent-engaging member 45 is, for example, at least about 30 mm from the proximal end 151 of the tip 150. The tip 150 may comprise a generally cylindrical portion 153 proximate to the proximal end 151 and having an outside surface 154. The tip 150 may comprise a generally conical or frusto-conical portion 155 proximate to the distal end 152 and having an outside surface 156.

In some embodiments, the tip 150 comprises at least one aperture 157, 158. The aperture 157, 158 is configured to allow fluid communication from outside of the outer sheath 20 to inside the outer sheath 20. In certain such embodiments, the at least one aperture 157 is configured to allow fluid communication between the proximal end 151 and the outside surface 154 and/or the at least one aperture 158 is configured to allow fluid communication between the proximal end 151 and the outside surface 156. The at least one aperture 157 may advantageously be less prone to accumulating fluid during advancement of the distal end of the device 10. In some embodiments, the at least one aperture 157, 158 comprises a groove (e.g., a U-shaped groove) in the tip 150. In some embodiments, the at least one aperture 157, 158 comprises a second lumen in the tip 150. The at least one aperture 157, 158 may be formed, for example, during molding of the tip 150 and/or may result from removing material (e.g., via etching, drilling, etc.) from the tip 150. In some embodiments, the at least one aperture comprises two grooves 180° apart in the generally cylindrical portion 153.

The at least one aperture 157, 158 may be useful for sterilizing the device 10. For example, ethylene oxide gas may flow through the at least one aperture 157, 158 to sterilize the stent 30, the stent-engaging member 45, and other components within the lumen of the outer sheath 20. In some embodiments, the cylindrical portion 153 has an outer diameter greater than the inner diameter of the outer sheath 20 (e.g., being substantially equal to the diameter of the outer sheath 20), for example so as to substantially occlude the lumen of the outer sheath 20 during advancement of the device 10. As described herein, the lumen of the outer sheath 20 is exposed to the operational environment, for example during operation of the switch 50, and foreign material may accumulate in the lumen of the outer sheath 20. The at least one aperture 157, 158 may be useful for flushing air from the device 10 before use (e.g., allowing flushing of saline through the device 10 while the tip 150 is proximate to the outer sheath 20).

FIG. 5B illustrates another example embodiment of a coupling structure between a tip 150 and a stent-engaging member 45. As described herein, the stent-engaging member 45 may comprise a stem 46 protruding beyond the distal end of the ratchet, and the distally extending portion may comprise features such as the helices 462. In some embodiments, the tube 75 is heat shrunk (e.g., by being radially inwardly compressed by a heat shrink sleeve) around the distal end of the stem 46, and material of the tube 75 extrudes into the features 462. The pusher assembly 500 may optionally comprise a melt coupler 76 coupling the stem 46 and the tube 75.

Figure 5C:
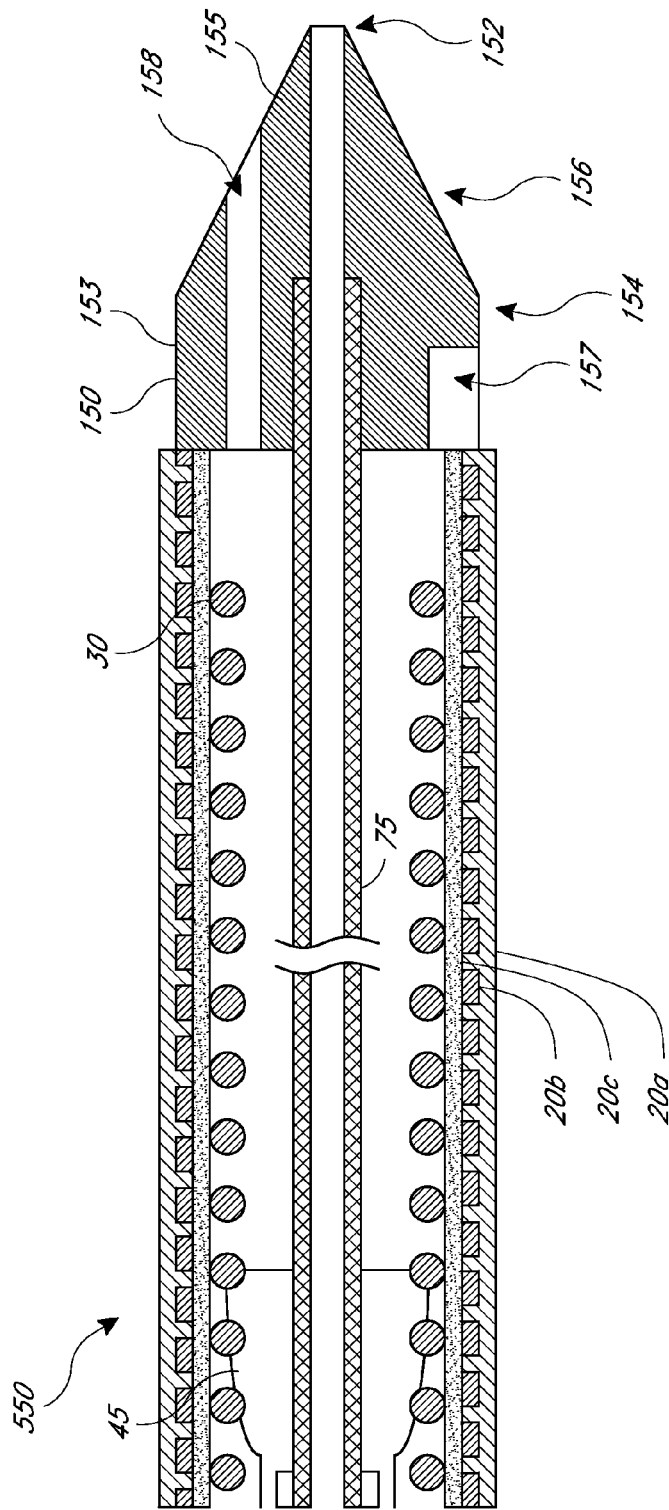
FIG. 5C is a cross-sectional view of an example embodiment of a distal portion of another example embodiment of a stent delivery device.

FIG. 5C illustrates an embodiment of a distal end 550 of a stent delivery device 10 comprising a pusher assembly 500 in which the outer sheath 20 of the device 10 comprises three layers: (1) an inner layer 20a (e.g., comprising polytetrafluoroethylene (PTFE or Teflon®)); (2) a middle layer 20b (e.g., comprising braided stainless steel ribbons); and (3) an outer layer 20c (e.g., comprising Pebax®). The outer diameter of the cylindrical portion of the tip 150 may be configured to correspond to (e.g., being aligned with the outer diameter of) one or more of the layers 20a, 20b, 20c of the outer sheath 20.

Figure 5D:
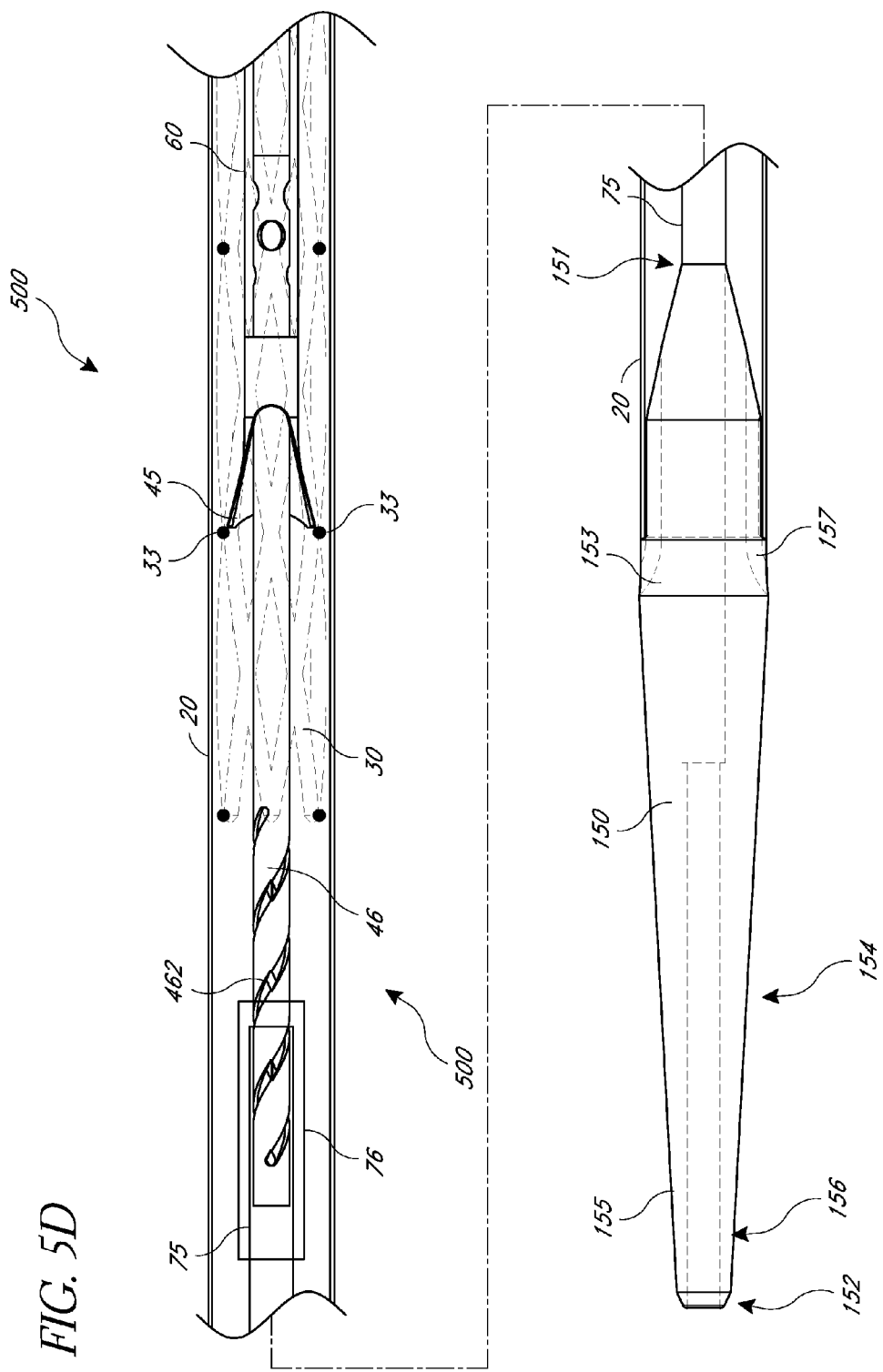
FIG. 5D is a cross-sectional view of an example embodiment of a distal portion of another example embodiment of a stent delivery device.

FIG. 5D illustrates an embodiment of a distal end of a stent delivery device 10 comprising a pusher assembly 500 in which the outer sheath 20 of the device 10 comprises three layers: (1) an inner layer 20a (e.g., comprising polytetrafluoroethylene (PTFE or Teflon®)); (2) a middle layer 20b (e.g., comprising braided stainless steel ribbons (e.g., having a different lattice density than the braided stainless steel ribbons illustrated in FIG. 5B); and (3) an outer layer 20c (e.g., comprising a first material (e.g., comprising Pebax®) and a second material different than the first material (e.g., comprising nylon)). For example, in some embodiments in which the outer layer 20c has a length of about 90 cm (or 900 mm), the proximal 70 cm (or 700 mm) may comprise a first material (e.g., comprising nylon) and the distal 20 cm (or 200 mm) may comprise a second material different than the first material (e.g., comprising Pebax®). For another example, in some embodiments in which the outer layer 20c has a length of about 120 cm (or 1,200 mm), the proximal 100 cm (or 1,000 mm) may comprise a first material (e.g., comprising nylon) and the distal 20 cm (or 200 mm) may comprise a second material different than the first material (e.g., comprising Pebax®). Other lengths and materials of the first material and the second material are also possible.

In certain embodiments, the outer layer 20c comprises one or a plurality of markers (e.g., marker bands) (not shown). In some embodiments, one or more of the markers may comprise a tungsten-infused polymer. A marker may be wide enough to provide a user information about the position of the device. In some embodiments, one or more of the markers may have a width between about 1 mm and about 2 mm (e.g., about 1.5 mm), less than about 2 mm, etc.

The outer diameter of the cylindrical portion of the tip 150 may be configured to correspond to (e.g., being aligned with the outer diameter of) one or more of the layers 20a, 20b, 20c of the outer sheath 20.

The inner member 60 at least partially defines a guidewire lumen through which a guidewire (e.g., having a diameter of 0.018 inches (approx. 0.46 mm)) may be passed. In embodiments comprising a tube 75, the tube 75 at least partially defines a guidewire lumen through which a guidewire (e.g., having a diameter of 0.018 inches (approx. 0.46 mm)) may be passed. In certain such embodiments, the inner diameter of the tube 75 is substantially equal to the inner diameter of the inner member 60 (e.g., the inner layer 60a). The nose cone 150 at least partially defines the guidewire lumen through which a guidewire (e.g., having a diameter of 0.018 inches (approx. 0.46 mm)) may be passed. The pusher assembly 500 thus includes a guidewire lumen through which a guidewire (e.g., having a diameter of 0.018 inches (approx. 0.46 mm)) may be passed.

The proximal end of the outer sheath 20 is stationarily coupled to the handle 90 and the proximal end of the inner member 60 is coupled to the switch 50. The switch 50 can slide along a handle path having two different longitudinal lengths: (1) a first length in which the stent-engaging member 45 cannot exit the distal end of the outer sheath 20, and (2) a second length in which the stent-engaging member 45 can exit the distal end of the outer sheath 20 (e.g., after removal of the stop 120). A user can push and pull the switch 50 back and forth relative to the handle 90 to distally extend and proximally retract the stent-engaging member (coupled to the distal end of the inner member 60, as described herein) relative to the outer sheath 20, which is stationary with respect to the handle 90.

During distal advancement of the switch 50, the stent-engaging member 45 engages an inner surface of the stent 30 at position 33 (e.g., "catching" on an intersection between braided filaments, as illustrated in FIGS. 5C-5F), thereby distally pushing the stent 30 out of the outer sheath 20.

Figure 5E:
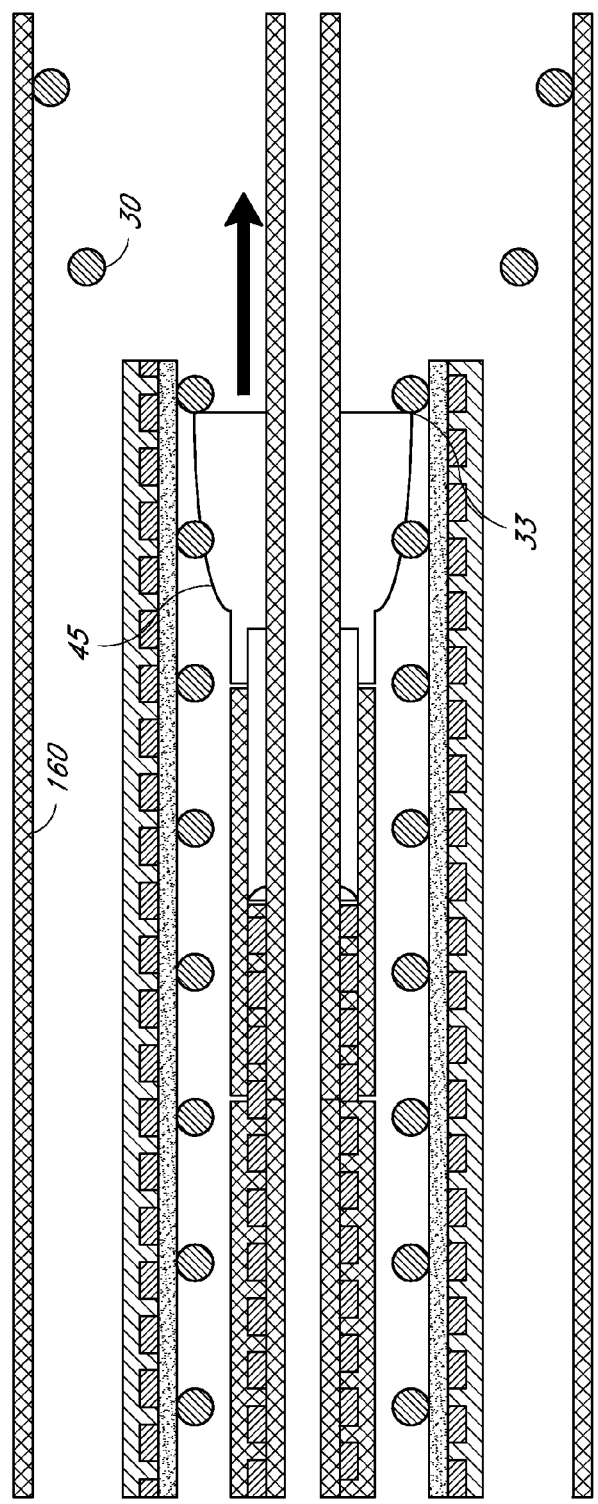
FIG. 5E is a cross-sectional view of the stent delivery device of FIG. 5A having a pusher assembly in a distally advanced position.
Figure 5F:
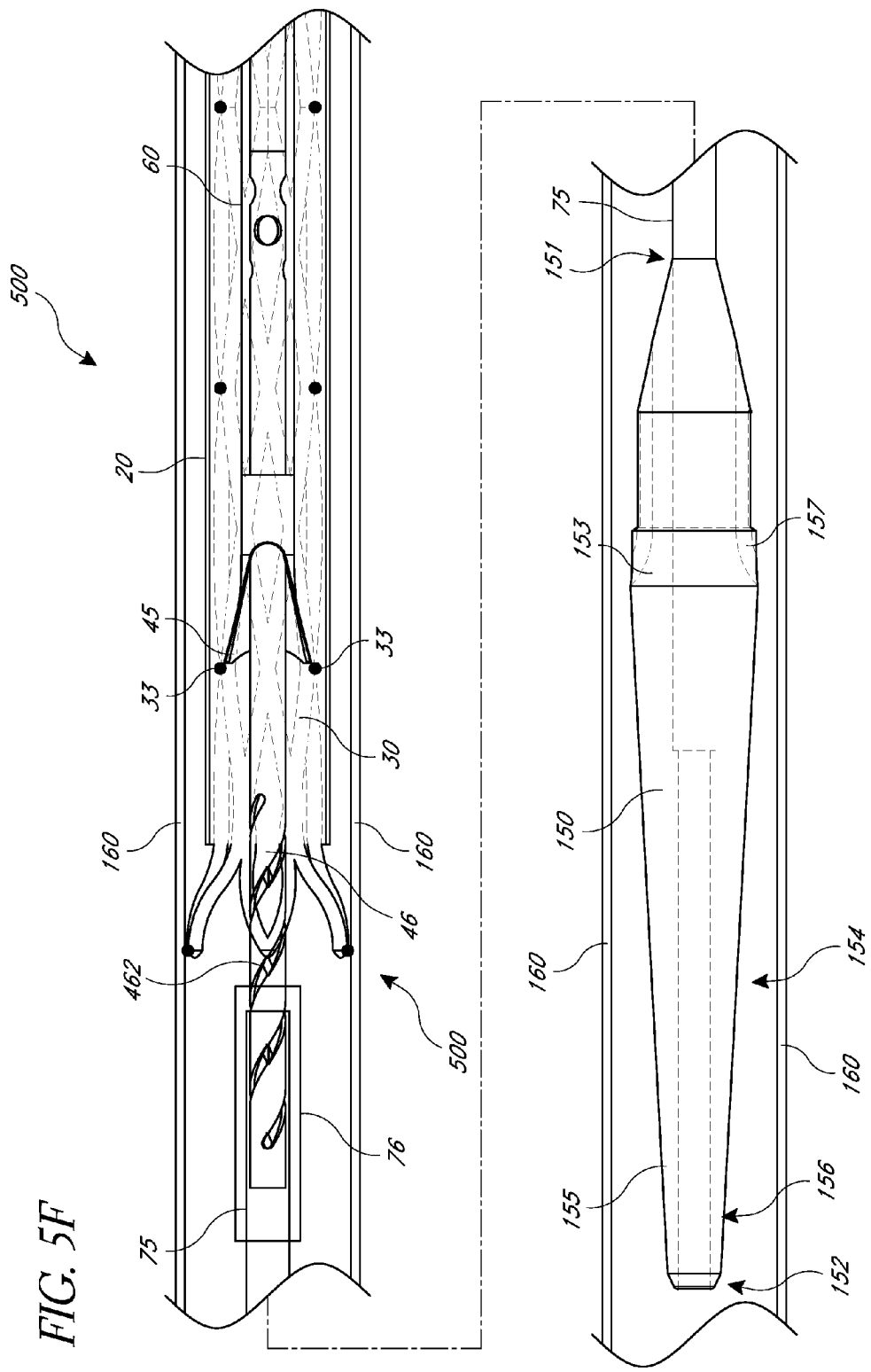
FIG. 5F is a cross-sectional view of the stent delivery device of FIG. 5B having a pusher assembly in a distally advanced position.

During proximal retraction of the switch 50, the stent-engaging member 45 does not engage the stent 30 because the stent-engaging member 45 radially inwardly flexes and noncatchingly slides along the inner surface of the stent 30. The stent 30 is deployed by moving the switch 50 back and forth, each forward moving pushing a portion of the stent 30 out of the outer sheath 20. FIGS. 5E and 5F each illustrates a stent 30 being deployed in a vessel, duct, or tube 160. Expansion of the stent 30 and engagement of the stent 30 with the vessel, duct, or tube wall 160 may cause the outer sheath 20 to move proximally, but the user does not perform any function to withdraw or to pull back the outer sheath 20. Once the stent 30 has been deployed, the device 10 is withdrawn from the vessel, duct, or tube 160.

FIG. 6 illustrates an embodiment in which the element 40 (e.g., comprising the inner member 60) is mechanically coupled to a stent-engaging member 45. In the embodiment illustrated in FIG. 6, the intermediate tube 42 of the element 40 is connected to the support tube 46, which is connected to the stent-engaging member 45. The stent-engaging member 45 is positioned at least partially within the lumen of a stent 30. As the element 40 moves distally in response to distal movement of the switch 50, the stent-engaging member 45 engages the stent 30, advancing the stent 30 along the outer sheath 20. Proximal motion of the stent-engaging member 45 results in no motion of the stent 30. Repeated reciprocating distal and proximal motion of the element 40 in this manner results in advancement of the stent 30 until it exits the outer sheath 20. Skilled artisans will appreciate that the illustrated embodiment of device 10 is configured such that a user can advance the stent 30 distally out of the outer sheath 20 through multiple engagements of the stent 30 by the stent-engaging member 45, where each engagement: occurs proximal to the distal end of the stent 30, drives the stent 30 distally without a concomitant withdrawal of the outer sheath 20, and is separated from any subsequent engagement by a period of not driving the stent 30 distally; and that the user's proximal-most point of contact with the device 10 that causes each engagement (which occurs at the switch 50) is located at or distal of the proximal end of device body 90. The stent-engaging member 45 may include a flex slot 48 provided with rounded, dumbbell-shaped ends that help alleviate fatigue stress fractures and the like and that allow the stent-engaging member 45 to fold inwardly as it slides proximally within the lumen of the stent 30.

The performance of stent-engaging member 45 may be achieved by appropriate shape selection, as depicted in FIGS. 7A and 7B. Alternate embodiments may employ stent-engaging elements 45 that flex, are hinged, or otherwise change shape to achieve stent advancement. The configuration of the stent-engaging member 45 may be chosen to best suit the type of stent 30 to be deployed. When the stent 30 is a woven, self-expanding stent, such as the kind disclosed in U.S. Pat. No. 7,018,401, which is incorporated herein by reference in its entirety, the stent-engaging member 45 may be configured (a) to engage wire intersections on opposing sides of the stent 30 when driving the stent 30 distally, and (b) to deform inwardly (e.g., due at least partially to a flex slot 48) and to slide proximally within the lumen of the stent 30. When the stent 30 is a laser-cut hypotube stent, the stent-engaging member 45 may be configured (a) to engage cut portions of the stent 30 when driving the stent 30 distally, and (b) to deform inwardly and to slide proximally within the lumen of the stent 30.

Figure 8:
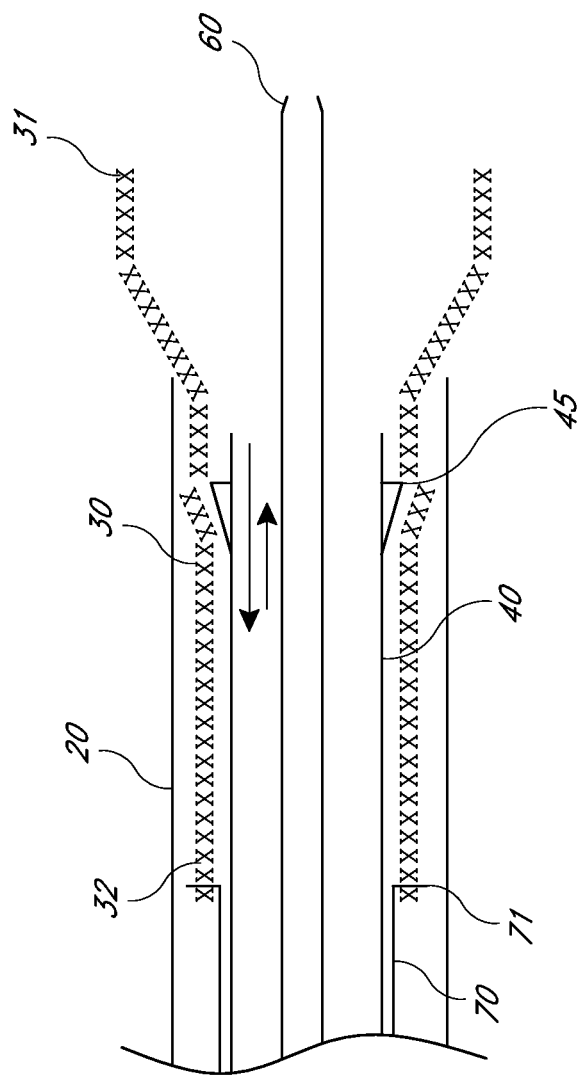
FIG. 8 schematically depicts an example embodiment of a stent-advancement process.

FIG. 8 provides a schematic depiction of a process for advancing and deploying a stent 30. The distal end 31 of the stent 30 has exited the outer sheath 20 and has expanded (e.g., to the size of the vessel or tube or as constrained by its expanded outer diameter). The element 40 moves proximally and distally, as indicated by the arrows. As the stent-engaging member 45 travels distally, it engages the stent 30 (e.g., cut portions of a laser-cut hypotube stent or the intersection between filaments of a woven stent), and distally advances the stent 30, thus driving the stent 30 out of the outer sheath 20. When the stent-engaging member 45 travels proximally, no advancement of the stent 30 occurs due to the shape of stent-engaging member 45. Instead, the configuration of stent-engaging member 45 enables it to bend or flex inwardly as it moves over and encounters portions (e.g., wire portions) of the stent 30 during the proximal movement of the switch 50 without disturbing the axial position of the stent 30 relative to the outer sheath 20. In some embodiments, advancement of the stent 30 is achieved without a mechanized concomitant withdrawal of the outer sheath 20 and without motion of the outer sheath 20 relative to the device body 90 (aside from incidental motion caused by patient's body movements, vibrations, etc.).

FIGS. 9 and 10 illustrate schematically deployment of a stent 30 in a body vessel 160. FIG. 9 depicts the stent 30 in a constrained, or elongated, configuration. This is an example of a configuration of the stent 30 when it is within the outer sheath 20 of the device 10 (e.g., as illustrated in FIG. 5B). FIG. 10 shows the stent 30 in an expanded state in the body vessel 160, which is one state a self-expanding stent 30 may take when it exits the outer sheath 20.

Figure 12A:
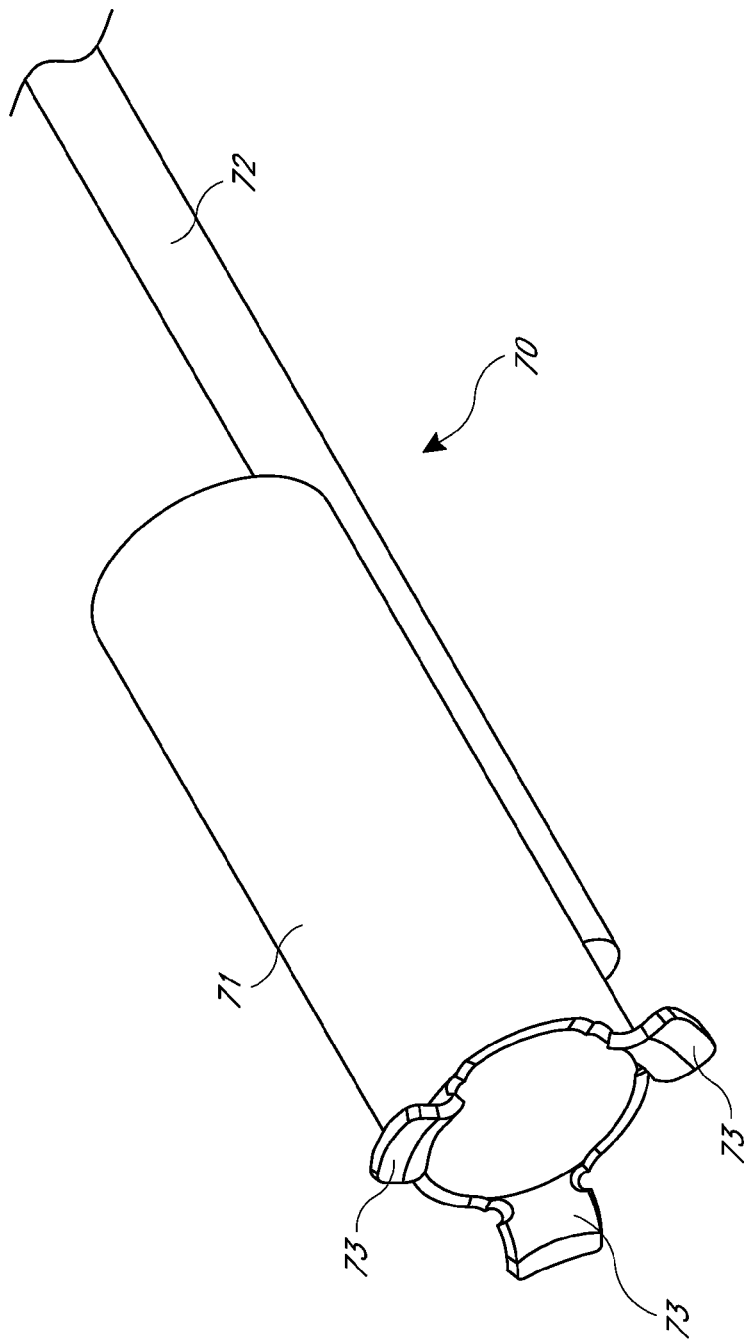
FIG. 12A illustrates an example embodiment of a stent-retention element.

In some embodiments, the device 10 includes a stent-retention element 70 configured to allow an operator to re-sheath the stent 30 during the advancement and/or deployment process, provided that the stent 30 has not been advanced completely out of the outer sheath 20. Referring to FIGS. 11 and 12A, the device 10 includes a stent-retention element 70 coupled to the proximal end 32 of the stent 30. Contact between the distal portion 71 of the stent-retention element 70 and the stent 30 exists as long as the proximal end 32 of the stent 30 is within the outer sheath 20, even during proximal movement of the stent-engaging member 45. When the proximal end 32 of the stent 30 is advanced outside of the outer sheath 20, the stent 30 expands to a radius larger than the greatest width (taken in the radial direction shown in the figures) of the distal portion 71 of the stent-retention element 70. As a result, contact between the stent 30 and the stent-retention element 70 ceases, and deployment of the stent 30 is irreversible. Accordingly, the stent-retention element 70 is operable to withdraw the stent 30 proximally back into the outer sheath 20 (through action by an operator) provided that a proximal portion of the stent 30 (specifically, the proximal portion coupled to the stent-retention element 70) remains disposed within the outer sheath 20.

The proximal portion 72 of the stent-retention element 70 may comprise a cable or similar device that facilitates withdrawal of the stent 30 proximally back into the outer sheath 20 and that may be characterized as a stent-retention line, provided that a proximal portion of the stent 30 is disposed within the outer sheath 20. The distal portion 71 of the stent-retention element 70 may comprise a piece of tubing (e.g., a hypotube) including a plurality of radially-projecting prongs 73 configured to engage openings in the stent 30 (e.g., windows between filaments, cut portions of a hypotube). The tubing of the stent-retention element 70 may be coupled in any suitable fashion (e.g., soldering) to the proximal portion 72 of the stent-retention element 70.

Figure 12B:
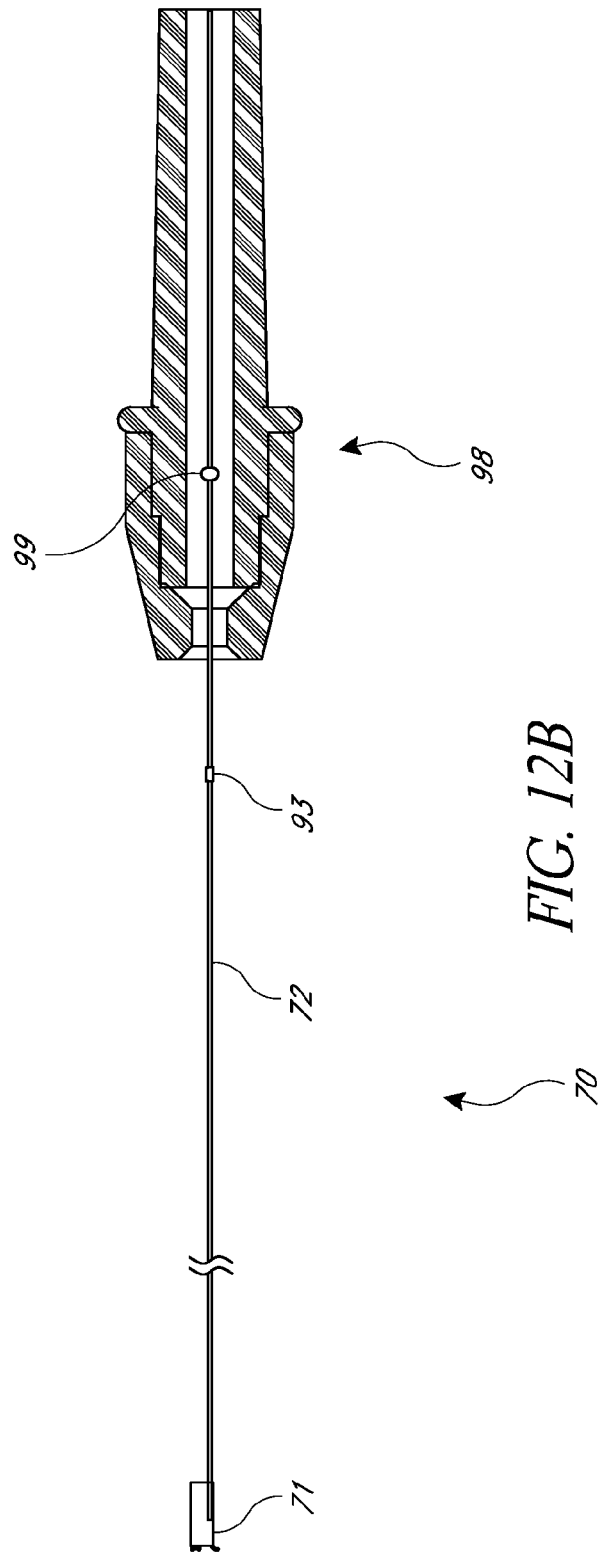
FIG. 12B illustrates another example embodiment of a stent-retention element.

As shown in FIGS. 1A and 2A, a Y-adapter 95 may be coupled to the proximal portion of device body 90. The inner member 60 may be placed through a straight arm 96 and the proximal portion 72 may be placed through an angled arm 97 of the Y-adapter 95. As shown in FIG. 2B, a stent-retention element position marker 93 may be coupled to the line 72 and may be positioned along the line 72 to the relative position of a stent 30 that is coupled to the stent-retention element 70. For example, the marker 93 (e.g., comprising a piece of heat shrink tubing), may be positioned along the line 72 such that when the lien 72 extends into the perimeter of the angled arm 97, the stent 30 will completely exit the outer sheath 20. In this way, an operator has a visual indicator that conveys how far the stent 30 has exited the outer sheath 20. FIGS. 1A and 2A also show that the stent-retention element 70 may include a finger element 98 coupled to the line 72 in any suitable manner (e.g., though Loctite® adhesive), to provide a user with something to hold to enable manipulation of the stent-retention element 70. FIG. 12B illustrates an embodiment of a stent-retention element 70 in which the finger element 98 is in cross-section, and depicts an example connection location 99 (e.g., comprising adhesive) between the line 72 and the finger element 98 (which may have inner and outer components that are threaded together).

In some embodiments, the device 10 comprises a side port 110 (coupled to device body 90) and a Luer fitting 100 (coupled to the proximal end 62 of the inner member 60), for example to allow flushing of the outer sheath 20 and the inner member 60, respectively. The flushing may be with saline and may occur prior to a procedure (e.g., thorough the at least one apertures 157, 158 as described herein). Some embodiments of the devices described herein may include designs for flushing the outer sheath 20 and/or the inner member 60, or may be configured to not allow for flushing of the outer sheath 20 and/or the inner member 60. FIG. 3D is a top view of the device 10 and identifies a cutaway detail near the distal end of the device body 90 that is shown in greater detail in FIG. 3E.

Referring to FIG. 2C, the second position 122 of the stopper 120 allows the switch 50 to travel distally the full length of the slot 52. The distal-most position of the switch 50 in the slot 52 (e.g., with the stopper 120 in the second position 120) corresponds to a position in which the stent-engaging member 45 is outside or distal to the distal end of the outer sheath 20, and therefore in a region where the stent 30 will be driven out of the outer sheath 20 and in its expanded state. A stent 30 in this position that is de-coupled from the distal portion 71 of the stent-retention element 70 can no longer be withdrawn back into the outer sheath 20. Furthermore, a stent 30 in an expanded condition has radial clearance over the stent-engaging member 45. Alternate embodiments of the devices disclosed herein may employ other designs to limit the travel of the switch 50, or have no adjustable travel-limiting feature.

Figure 13:
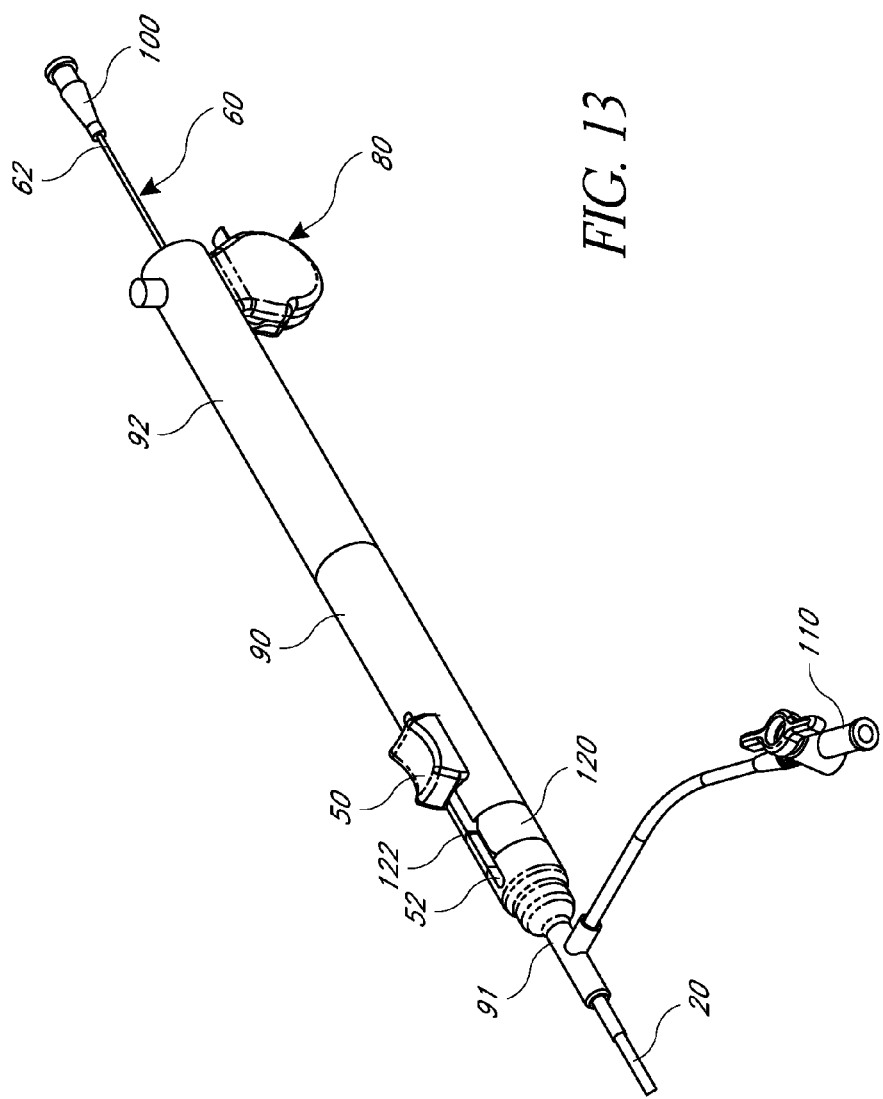
FIG. 13 illustrates another example embodiment of a proximal portion of the stent delivery device encircled by the line 2 in FIG. 1.
Figure 14:
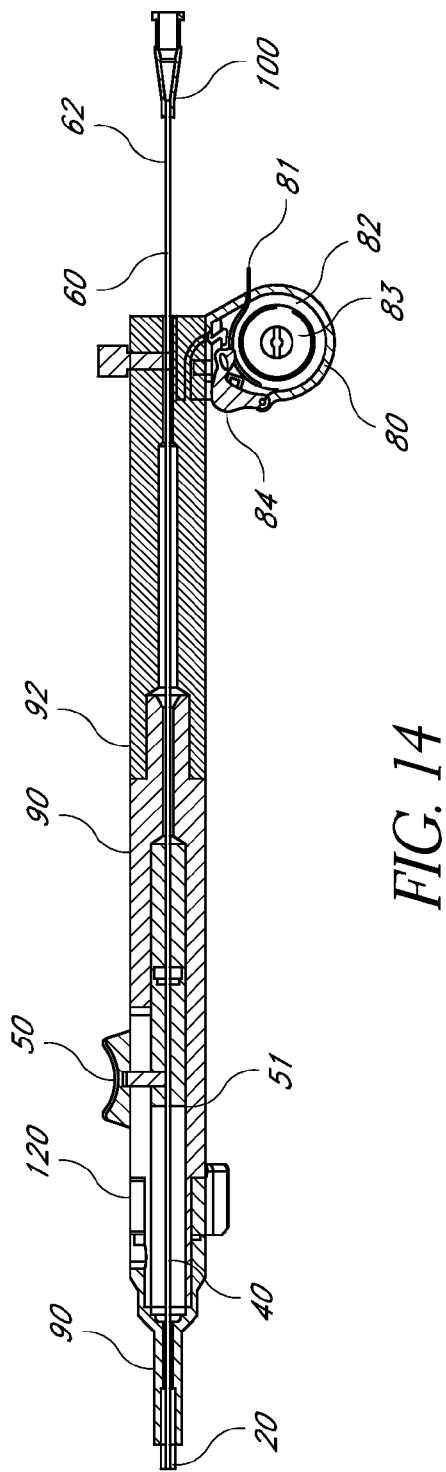
FIG. 14 is a cross-sectional view of the proximal portion of the stent delivery device illustrated in FIG. 13.

FIGS. 13 and 14 depict another example embodiment of devices 10 that include a capture device 80 coupled to the proximal portion 72 of the stent-retention element 70. The capture device 80 serves to release appropriate amounts of the proximal portion 72 as the stent-engaging member 45 advances the stent 30. The capture device 80 includes a stop that serves to halt distal advancement of the stent 30 prior to full deployment of the stent 30 from the outer sheath 20. The stop (which can be a piece of tubing, such as hypotube, that is coupled at an appropriate location to the proximal portion 72) provides operator feedback at the point where further advancement would result in deployment of the stent 30 (thus, the stop can be used as an indicator of the location at which withdrawal of the stent 30 will no longer be possible). Here, the operator may choose to withdraw the stent 30 into the outer sheath 20 for repositioning by pulling proximally on the stent-retention element 70, or proceed with deployment of the stent 30 by depressing a deployment stop lever 81 (which allows the stop to bypass the deployment stop lever and permits continued distal advancement of the stent-retention element 70) and continuing with advancement via the switch 50.

If the operator chooses to withdraw the stent 30 back into the outer sheath 20 for repositioning, the operator can actuate retention pull a lever 84, which, in the depicted embodiment, de-couples the capture device 80 from the device body 90 and allows the operator to proceed with drawing back the stent 30 by proximally pulling the proximal portion 72 of the stent-retention element 70. After withdrawal of the stent 30 back into outer the sheath 20, the retention pulley 82 and the spring 83 of the capture device 80 operate to accumulate excess slack of the stent-retention element 70. In this embodiment, the proximal portion 72 of the stent-retention element 70 may be threaded through a portion of device body 90 that is not centrally disposed within the device body 90. Alternate embodiments of the devices disclosed herein may include capture devices that are configured differently from the capture device 80, such as automated capture devices. Furthermore, the capture device 80 may be coupled to the angled arm 97 in the embodiment of the device 10 shown in FIG. 1A, in place of the finger element 98.

The devices 10 described herein may be disposable and packaged in a bag, pouch, box, or other suitable container, after having been sterilized using any suitable technique, such as sterilization using ethylene oxide gas. There may be a small gap between the distal end of the outer sheath 20 and the proximal end of the nose cone 150 to allow for the sterilizing gas to flow throughout the device 10. The container may include instructions for using the device 10 that are printed on the container or included inside the container. After the device 10 is removed from the container, saline may be used to flush the outer sheath 20 and its contents and the inner member 20 (e.g., through the side port 110). The gap between the nose cone 150 and the outer sheath 20 can then be closed by pulling proximally on the inner member 60 to which the nose cone 150 is coupled. If the procedure involves stenting a blood vessel, any suitable technique for positioning the device 10 in the appropriate location may be used (e.g., the Seldinger technique). The nose cone 150 of the device 10, which may be any suitable flexible atraumatic tip, may be radiopaque and may represent a distal-most marker for the device 10. Another radiopaque marker made from any suitable material (e.g., a platinum or platinum-alloy band) may be coupled to a portion of the device 10 that is proximal to the nose cone 150, such as to the outer sheath 20 (as discussed above), the element 40, or the inner member 60, to create a proximal-most marker for the device 10. These two markers may be used by the operator to position the device 10 relative to the site of interest to enable accurate deployment of the stent 30.

A stent (e.g., the stent 30) may be distally driven out of a sheath (e.g., the outer sheath 20) and into a tubular structure 160 using the device 10. In some embodiments, the tubular structure 160 is animal tissue (such as a human blood vessel). In other embodiments, the tubular structure 160 is not animal tissue and comprises a polymer structure that can be used to test a given device technique or to demonstrate a stent advancement to one or more persons, such as a doctor considering using the device 10 or a stent advancement technique in his or her practice.

Figure 15A:
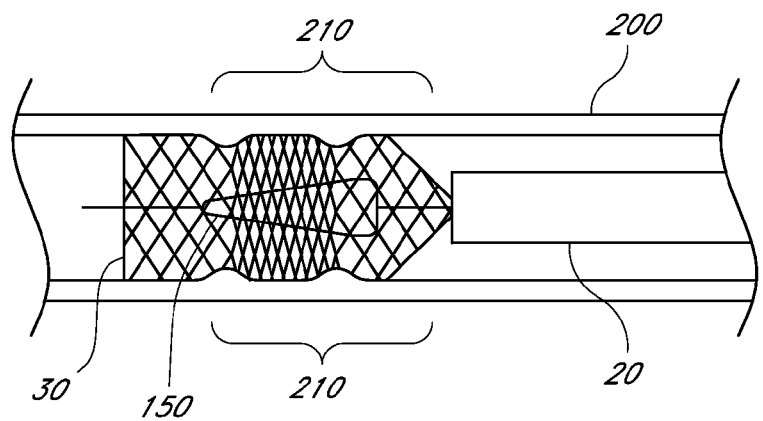
FIG. 15A schematically depicts another example embodiment of deploying a stent in a vessel.
Figure 15B:
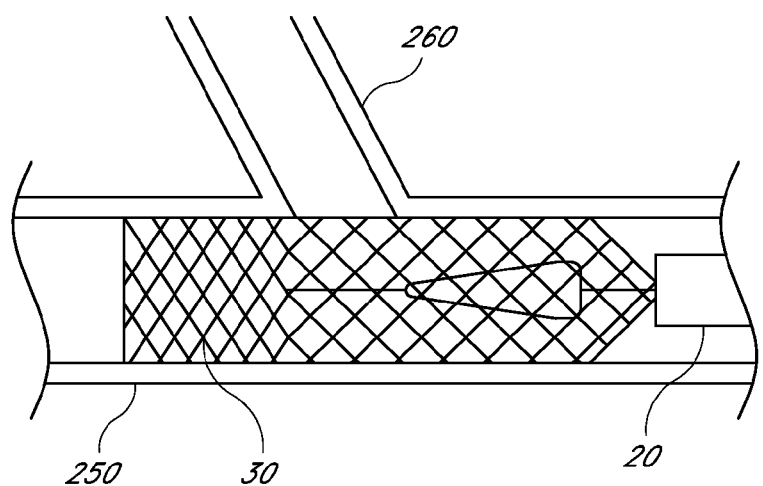
FIG. 15B schematically depicts yet another example embodiment of deploying a stent in a vessel.

Some methods include distally driving a stent (e.g., the stent 30) out of a sheath (e.g., outer sheath 20) and into a tubular structure 160 by repeatedly engaging the stent with a stent-engaging element (e.g., the stent-engaging member 45), where at least two of the engagements are separated by a period of non-engagement; and as the stent is distally driven out of the sheath, allowing varying of the axial density of the stent within the tubular structure 160 by varying the axial position of the sheath relative to the tubular structure 160. As the stent is driven distally out of the sheath, the remainder of the device 10 is withdrawn proximally by the operator relative to the tubular structure 160 so that the deployed portion of the stent remains stationary relative to the tubular structure 160 (e.g., human tissue) into which the stent is deployed. The rate at which the remainder of the device 10 is withdrawn may be varied to vary the axial density of the stent: a slower withdrawal rate increases the axial density of the stent, whereas a faster rate decreases the axial density of the stent. Increasing the axial density of the stent may, for example, provide greater hoop strength at a location where a greater hoop strength may be needed to maintain patency of the tubular structure 160, such as along a stenosed region 210 of an artery 200, for example as shown in FIG. 15A. Decreasing the axial density of the stent in may, for example, be at a location where fluid flow into or out of a section of the stent from the side is anticipated or desired, or may be at the location of penetration of a second stent, either of which may be true at an anatomical side branch 260 of a vessel 250, for example as shown in FIG. 15B.

Some embodiments of stent advancement methods include distally driving a stent (e.g., the stent 30) out of a sheath (e.g., the outer sheath 20) and into a tubular structure 160 by repeatedly engaging the stent between its distal and proximal ends with a stent-engaging element (e.g., the stent-engaging member 45), where at least two of the engagements are separated by a period of non-engagement; and optionally engaging the stent at its proximal end with a stent-retention element (e.g., the stent-retention element 70) that is positioned within the sheath.

In some embodiments, engagements that drive the stent distally from the sheath may be achieved using a device that is configured to not mechanically concomitantly withdraw the sheath as the stent is driven distally, such as the versions of the devices 10 described herein. The tubular structure 160 in those embodiments can be an anatomical tubular structure, such as a vessel or duct, or a tubular structure that is not animal tissue, such as a polymer tube 300, for example as illustrated in FIG. 15C. Regardless of the type of tubular structure 160, in some embodiments, the method may also include engaging the stent at its proximal end with a stent-retention element (e.g., the stent-retention element 70) that is positioned within the sheath. The stent-retention element may include a stent-retention line (e.g., the line 72), and the method may also include, after the stent is partially-driven out of the sheath, withdrawing the stent back into the sheath by moving the stent-retention line. An operator may accomplish driving of the stent by moving a user-actuatable element (e.g., the switch 50) with the operator's thumb. If the stent is woven, a stent-engaging element may engage on or more wire intersections of the stent and move distally during the engagements that drive the stent, and the stent-engaging element may slide proximally within the lumen of the stent during the period of non-engagement.

Some of the methods described herein are methods of instructing another or others on how to advance a stent out of sheath and into a tubular structure. In some embodiments, the method includes instructing a person on how to use a stent delivery device (e.g., the device 10) that includes a sheath (e.g., the outer sheath 20) and a stent (e.g., the stent 30) disposed in the sheath. The instructing may include demonstrating the following steps to the person: distally driving the stent out of the sheath and into a tubular structure by repeatedly engaging the stent with a stent-engaging element (e.g., the stent-engaging member 45), where at least two of the engagements are separated by a period of non-engagement; and, as the stent is distally driven out of the sheath, optionally varying the axial density of the stent within the tubular structure by varying the axial position of the sheath relative to the tubular structure.

In some embodiments, the method includes instructing a person on how to use a stent delivery device (e.g., the device 10) that includes a sheath (e.g., the outer sheath 20) and a stent (e.g., the stent 30) disposed in the sheath. The instructing may include demonstrating the following steps to the person: distally driving the stent out of the sheath and into a tubular structure by repeatedly engaging the stent with a stent-engaging element (e.g., the stent-engaging member 45), where at least two of the engagements are separated by a period of non-engagement; and, optionally, engaging the stent at its proximal end with a stent-retention element (e.g., the stent-retention element 70) that is positioned within the sheath.

Figure 16:
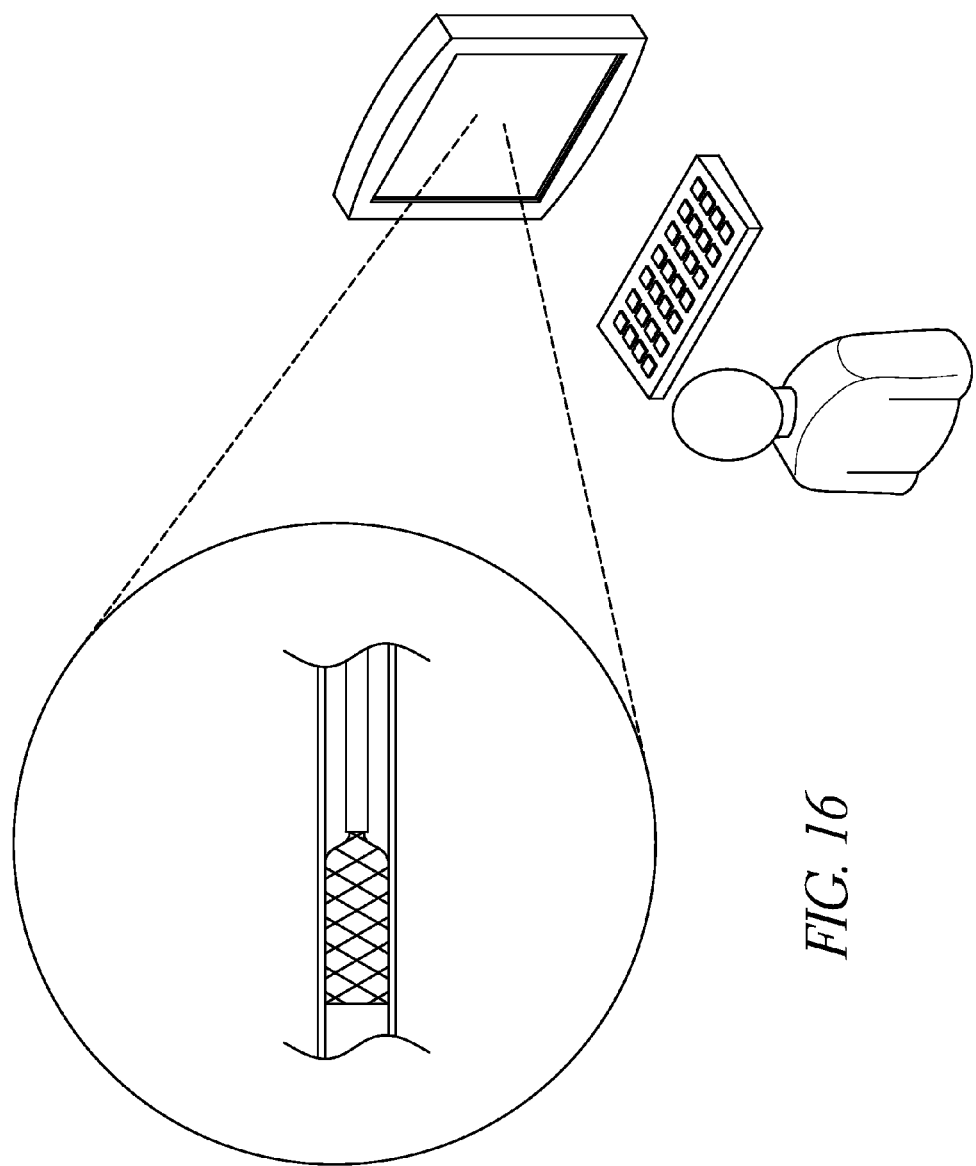
FIG. 16 illustrates an example embodiment of a computer system.

In some embodiments, the instruction methods may be accomplished by a live demonstration in the presence of the person or by a recorded or simulated demonstration that is played for the person. An example of a recorded demonstration is one that was carried out by a person and captured on camera. An example of a simulated demonstration is one that did not actually occur, and that instead was generated using a computer system and a graphics program. In the case of a recorded or simulated demonstration, the demonstration may exist in any suitable form—such as on DVD or in any suitable video file (such as 0.3 gp, .avi, .dvx, .flv, .mkv, .mov, .mpg, .qt, .rm, .swf, .vob, .wmv, etc.)—and the instructing may be accomplished by playing the demonstration for the viewer using any suitable computer system. The viewer or viewers may cause the demonstration to play. For example, the viewer may access the recorded or simulated demonstration file using the internet, or any suitable computer system that provides the viewer with access to the file, for example as illustrated in FIG. 16.

In some embodiments, the method involves delivery of a stent into an anatomical structure, and in which the device used to accomplish the method is in a desired location within a patient to start the stent advancement, the movement (e.g., the ratcheting movement) of the stent-engagement element can begin such that the distal end of the stent (which can also be provided with one or more radio opaque markers to enable easier viewing of its position during the procedure) exits the sheath of the device, but not to such an extent that it expands to contact the anatomical structure. If the distal end of the stent is proximal of where the operator wants it, and a stent-retention element is used, the stent-retention element can be pulled proximally to resheath the stent and reposition the device; if the stent is distal of where the operator wants it, the entire device can be withdrawn proximally and the deployment process continued.

The features of the devices described herein can be made from commercially-available, medical-grade materials. For example, the nose cone 150 may comprise a polyether block amide (such as Pebax® resin, available from Arkema Inc, Philadelphia, Pa.). A distal portion of inner member 60 (such as inner sleeve 61) may comprise polyimide and coupled to a more proximal portion comprising stainless steel hypotube (such as 304 or 316L stainless steel). The Luer fitting 100 coupled to the inner member 60 (e.g., outer sleeve 63) may comprise polycarbonate. The outer sheath 20 may comprise a braided polyether block amide (e.g., comprising a braided Pebax® resin). The device body 90, switch 50, block 51, and stopper 120 may comprise acrylonitrile butadiene styrene (ABS) plastic, polycarbonate, Delrin® acetal resin (available from DuPont), and the like. The stopper 120 may be coupled to a stainless steel spring that biases it as described above. The element 40 may comprise a shaft comprising polyimide (or, a series of shafts comprise from polyimide or a hypotube comprising nickel-titanium alloy), and the stent-engaging member 45 may include or be coupled to a stem 46 (e.g., comprising a hypotube comprising nickel-titanium alloy) coupled to the polyimide shaft with a suitable adhesive (e.g., Loctite® adhesive, which includes cyanoacrylates) and a piece of hypotube (e.g., comprising nickel-titanium alloy) fashioned in the desired shape and welded (e.g., laser welded) to the stem 46. The stent-retention element 70 may include an intertwined stainless steel wire (used as proximal portion 72) that is covered with a material such as nylon, fluorinated ethylene propylene (FEP) tubing, or polyester (PET) tubing, and the distal portion 71 may comprise a hypotube (e.g., comprising stainless steel). Furthermore, steps may be taken to reduce the friction between the parts that contact or may contact either other during use of the present devices, such as contact between the stent and the outer sheath.

The devices described herein may be used to deliver self-expending stents that are woven, including stents woven from multiple strands, such as wires. Some examples of weaving techniques that may be used include those in U.S. Pat. Nos. 6,792,979 and 7,048,014, which are each incorporated herein by reference in its entirety. The strands of a woven stent may terminate in strand ends (e.g., wire ends) that are then joined together using small segments of material, such as nitinol hypotube, when the stent strands are wires made from nitinol. The stent may be passivated through any suitable technique in order to remove the oxide layer from the stent surface that can be formed during any heat treating and annealing, thus improving the surface finish and corrosion resistance of the stent material. Suitable stent creation techniques for stents that may be used with the present devices (including the strand crossings that may be engaged by stent-engaging member 45) are set forth in U.S. patent application Ser. No. 11/876,666, published as U.S. Patent Pub. No. 2008/0290076, which is incorporated herein by reference in its entirety.

It will be appreciated that the devices and methods described herein are not intended to be limited to the particular forms disclosed. Rather, they cover all modifications, equivalents, and alternatives falling within the scope of the example embodiments. For example, while the embodiments of the devices shown in the figures included a stent-engaging element 45 and a switch 50 that move the same distances in response to operator input, other embodiments could include gears or other mechanisms that create a ratio between the distance that the switch 50 moves and the resulting distance that the stent-engaging element 45 moves that is not 1:1 (such that the reciprocating element distance can be greater or less than the distance of the switch 50). For another example, devices may lack features such as a flush port 110 and/or a stent-retention element 70. Furthermore, still other embodiments may employ other structures for achieving periodic engagement of a stent 30 in order to advance it distally, such as a through a squeeze-trigger mechanism similar to the one shown in U.S. Pat. No. 5,968,052 or in U.S. Pat. No. 6,514,261, each of which is incorporated herein by reference in its entirety, or through a stent-engaging element that rotates rather than translates and that possesses a cam portion configured to engage the stent during part of a given rotation and not engage the stent during another part of that rotation. Moreover, still other embodiments may employ other forms of reciprocating movement of a stent-engaging element (such as the stent-engaging member 45), such as through another form of operator input like a rotational user-actuatable input (rather than a longitudinal translation input) coupled to the stent-engaging element via a cam.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

What is claimed is:

1. A pusher assembly for a stent delivery device, the pusher assembly comprising:
   a distal end of an elongate inner member; and
   a stent-engaging member having a proximal end and a distal end, the proximal end of the stent-engaging member being at least partially inside the distal end of the elongate inner member, the stent-engaging member comprising a portion that radially outwardly extends towards the distal end of the stent-engaging member, the stent-engaging member configured to move a stent when distally advanced and configured to not move a stent when proximally retracted, wherein the proximal end of the stent-engaging member comprises an aperture, wherein the elongate inner member comprises an inner layer, and wherein an inner surface of the inner layer of the elongate inner member at least partially fills the aperture such that a portion of the inner layer extends inward of an outer surface of the proximal end of the stent-engaging member;
   wherein the stent-engaging member comprises a stem and a ratchet mechanically coupled to the stem by a plurality of spot welds on a first side of the ratchet, and the ratchet spaced from the stem by a pap on a second side of the ratchet opposite the first side of the ratchet.

2. The pusher assembly of claim 1, wherein the stent-engaging member has a first internal diameter, wherein the elongate inner member has a second internal diameter proximal to the proximal end of the stent-engaging member, and wherein the first internal diameter is substantially equal to the second internal diameter.

3. The pusher assembly of claim 1, wherein the portion has a shovel shape having a flat distal end.

4. The pusher assembly of claim 1, wherein the portion has a shovel shape having a flared distal end.

5. The pusher assembly of claim 1, wherein the ratchet comprising the portion.

6. The pusher assembly of claim 1, wherein the proximal end of the stent-engaging member comprises the stem.

7. The pusher assembly of claim 1, wherein the aperture comprises a plurality of holes.

8. The pusher assembly of claim 1, wherein the distal end of the stent-engaging member comprises a cutout and wherein the pusher assembly further comprises a tube positioned around the distal end of the stent-engaging member and at least partially filling the cutout.

9. The pusher assembly of claim 8, wherein the cutout comprises a plurality of helical slots.

10. The pusher assembly of claim 1, wherein the elongate inner member at least partially defines a guidewire lumen, and wherein the stent-engaging member at least partially defines the guidewire lumen.

11. A pusher assembly for a stent delivery device, the pusher assembly comprising:
  a distal end of an elongate inner member; and
  a stent-engaging member having a proximal end and a distal end, at least a portion of the stent-engaging member being radially inward of an inner layer of the elongate inner member, the stent-engaging member comprising a portion that radially outwardly extends towards the distal end of the stent-engaging member, the stent-engaging member configured to move a stent when distally advanced and configured to not move a stent when proximally retracted, wherein the elongate inner member at least partially defines a guidewire lumen, and wherein the stent-engaging member at least partially defines the guidewire lumen, the guidewire lumen having an open distal end through which a guidewire may be passed;
  wherein the stent-engaging member comprises a stem and a ratchet mechanically coupled to the stem by a plurality of spot welds on a first side of the ratchet, and the ratchet spaced from the stem by a pap on a second side of the ratchet opposite the first side of the ratchet.

12. The pusher assembly of claim 11, wherein the stent-engaging member has a first internal diameter, wherein the elongate inner member has a second internal diameter proximal to the proximal end of the stent-engaging member, and wherein the first internal diameter is substantially equal to the second internal diameter.

13. The pusher assembly of claim 11, wherein the portion has a shovel shape having a flat distal end.

14. The pusher assembly of claim 11, wherein the portion has a shovel shape having a flared distal end.

15. The pusher assembly of claim 11, wherein the ratchet comprising the portion.

16. The pusher assembly of claim 11, wherein the proximal end of the stent-engaging member comprises the stem.

17. The pusher assembly of claim 11, wherein the distal end of the stent-engaging member comprises a cutout and wherein the pusher assembly further comprises a tube positioned around the distal end of the stent-engaging member and at least partially filling the cutout.

18. The pusher assembly of claim 17, wherein the cutout comprises a plurality of helical slots.

19. A pusher assembly for a stent delivery device, the pusher assembly comprising:
  a distal end of an elongate inner member; and
  a stent-engaging member having a proximal end and a distal end, the proximal end of the stent-engaging member being at least partially inside the distal end of the elongate inner member, the stent-engaging member comprising a portion that radially outwardly extends towards the distal end of the stent-engaging member, the stent-engaging member configured to move a stent when distally advanced and configured to not move a stent when proximally retracted, wherein the stent-engaging member comprises a stem and a ratchet, the stem radially inward of the ratchet, the ratchet mechanically coupled to the stem by a plurality of spaced spot welds on a first side of the ratchet, the ratchet spaced from the stem by a gap on a second side of the ratchet generally opposite the first side of the ratchet, the ratchet comprising the portion.

20. The pusher assembly of claim 19, wherein the stent-engaging member has a first internal diameter, wherein the elongate inner member has a second internal diameter proximal to the proximal end of the stent-engaging member, and wherein the first internal diameter is substantially equal to the second internal diameter.

21. The pusher assembly of claim 19, wherein the portion has a shovel shape having a flat distal end.

22. The pusher assembly of claim 19, wherein the portion has a shovel shape having a flared distal end.

23. The pusher assembly of claim 19, wherein the proximal end of the stent-engaging member comprises the stem.

24. The pusher assembly of claim 19 wherein the distal end of the stent-engaging member comprises a cutout and wherein the pusher assembly further comprises a tube positioned around the distal end of the stent-engaging member and at least partially filling the cutout.

25. The pusher assembly of claim 24, wherein the cutout comprises a plurality of helical slots.

26. The pusher assembly of claim 1, wherein the portion of the stent-engaging member is configured to engage a stent during distal advancement and to flex inwardly during proximal retraction of the stent-engaging member.

27. The pusher assembly of claim 11, wherein the portion of the stent-engaging member is configured to engage a stent during distal advancement and to flex inwardly during proximal retraction of the stent-engaging member.

28. The pusher assembly of claim 19, wherein the portion of the stent-engaging member is configured to engage a stent during distal advancement and to flex inwardly during proximal retraction of the stent-engaging member.

29. The pusher assembly of claim 19, wherein the stem is generally coaxial with the ratchet.

* * * * *